US010286027B2

(12) United States Patent
Antony

(10) Patent No.: US 10,286,027 B2
(45) Date of Patent: *May 14, 2019

(54) SUSTAINED RELEASE FORMULATIONS OF CURCUMINOIDS AND METHOD OF PREPARATION THEREOF

(71) Applicant: Arjuna Natural Extracts, Ltd., Alwaye (IN)

(72) Inventor: Benny Antony, Ankamaly (IN)

(73) Assignee: ARJUNA NATURAL EXTRACTS, LTD., Alwaye (IN)

( * ) Notice: Subject to any disclaimer, the term of this patent is extended or adjusted under 35 U.S.C. 154(b) by 726 days.

This patent is subject to a terminal disclaimer.

(21) Appl. No.: 14/800,950

(22) Filed: Jul. 16, 2015

(65) Prior Publication Data
US 2016/0067300 A1 Mar. 10, 2016

Related U.S. Application Data

(60) Continuation-in-part of application No. 14/476,555, filed on Sep. 3, 2014, now Pat. No. 10,159,654, which is a division of application No. 13/645,031, filed on Oct. 4, 2012, now Pat. No. 8,859,020, application No. 14/800,950, which is a continuation-in-part of application No. 14/623,608, filed on Feb. 17, 2015, now Pat. No. 9,878,040, and a continuation-in-part of application No. 14/520,292, filed on Oct. 21, 2014, now Pat. No. 9,861,677, and a continuation-in-part of application No. 14/206,044, filed on Mar. 12, 2014, now Pat. No. 9,492,402, said application No. 13/645,031 is a continuation-in-part of application No. PCT/IN2011/000232, filed on Apr. 4, 2011, said application No. 14/623,608 is a division of application No. 13/674,249, filed on Nov. 12, 2012, now Pat. No. 8,993,013, which is a division of application No. 13/506,572, filed on Apr. 30, 2012, now Pat. No. 8,329,233, which is a division of application No. 12/926,980, filed on Dec. 21, 2010, now Pat. No. 8,197,869, which is a division of application No. 12/073,864, filed on Mar. 11, 2008, now Pat. No. 7,883,728, which is a continuation-in-part of application No. 11/635,599, filed on Dec. 8, 2006, now Pat. No. 7,736,679, said application No. 14/520,292 is a division of application No. 14/094,725, filed on Dec. 2, 2013, now Pat. No. 8,895,087, which is a division of application No. 13/385,717, filed on Mar. 5, 2012, now Pat. No. 8,623,431, which is a division of application No. 12/926,985, filed on Dec. 21, 2010, now Pat. No. 8,153,172, which is a division of application No. 12/662,740, filed on Apr. 30, 2010, now Pat. No. 7,879,373, which is a division of (Continued)

(30) Foreign Application Priority Data

Apr. 5, 2010 (IN) .............................. 950/CHE/2010
Nov. 3, 2012 (IN) ............................ 4128/CHE/2012
Jan. 17, 2013 (IN) ............................ 226/CHE/2013

(51) Int. Cl.
| | |
|---|---|
| A61K 31/12 | (2006.01) |
| A61K 9/00 | (2006.01) |
| A61K 36/9066 | (2006.01) |
| A61K 47/44 | (2017.01) |
| A61K 47/38 | (2006.01) |
| A61K 47/32 | (2006.01) |

(52) U.S. Cl.
CPC ........ *A61K 36/9066* (2013.01); *A61K 9/0053* (2013.01); *A61K 31/12* (2013.01); *A61K 47/32* (2013.01); *A61K 47/38* (2013.01); *A61K 47/44* (2013.01)

(58) Field of Classification Search
None
See application file for complete search history.

(56) References Cited

U.S. PATENT DOCUMENTS

| | | |
|---|---|---|
| 3,340,250 A | 9/1967 | Sair |
| 5,120,538 A | 6/1992 | Oei |

(Continued)

FOREIGN PATENT DOCUMENTS

| | | |
|---|---|---|
| CN | 1483405 A | 3/2004 |
| CN | 1489994 A | 4/2004 |

(Continued)

OTHER PUBLICATIONS

Anand P, et al "Bioavailability of Curcumin: Problems and Promises" Mol. Pharmaceutics, 2007 (ePub. Nov. 14, 2007), 4(6), pp. 807-818: DOI: 10.1021/mp700113r. (Year: 2007).*

Aratanechemuge, Y, Komiya, T, Moteki, H, Katsuzaki, H, Imai, K, and Hibasami, H, Selective Induction of Apoptosis by ar-Turmerone Isolated From Turmeric (*Curcuma longa* L) In Two Human Leukemia Cell Lines, But Not In Human Stomach Cancer Cell Line, International Journal of Molecular Medicine, 9:481-484 (2002).

(Continued)

*Primary Examiner* — Aaron J Kosar
(74) *Attorney, Agent, or Firm* — Jyoti C. Iyer

(57) ABSTRACT

A sustained release curcuminoid composition having a bioavailable curcumin composition and a release rate controlling excipient. The bioavailable composition of curcumin includes a curcuminoid mixture and an added essential oil of turmeric. The curcuminoid mixture includes curcumin, demethoxycurcumin and bisdemethoxycurcumin. The added essential oil of turmeric includes about 40% to about 50% of ar-turmerone. Methods of preparing sustained release compositions having a bioavailable curcumin composition and a release rate controlling excipient.

32 Claims, 33 Drawing Sheets

Related U.S. Application Data application No. 11/635,599, filed on Dec. 8, 2006, now Pat. No. 7,736,679, which is a continuation of application No. PCT/IN2005/000176, filed on May 30, 2005, said application No. 14/206,044 is a continuation-in-part of application No. 13/645,031, filed on Oct. 4, 2012, now Pat. No. 8,859,020, and a continuation-in-part of application No. 13/674,249, filed on Nov. 12, 2012, now Pat. No. 8,993,013, and a continuation-in-part of application No. 14/094,725, filed on Dec. 2, 2013, now Pat. No. 8,895,087, application No. 14/800,950, which is a continuation of application No. PCT/IN2014/000031, filed on Jan. 16, 2014, and a continuation-in-part of application No. 14/698,944, filed on Apr. 29, 2015, which is a continuation of application No. PCT/IN2013/000673, filed on Oct. 31, 2013.

(60) Provisional application No. 61/794,175, filed on Mar. 15, 2013.

(56) References Cited

U.S. PATENT DOCUMENTS

| | | | |
|---|---|---|---|
| 5,536,506 | A | 7/1996 | Majeed |
| 5,861,415 | A | 1/1999 | Majeed |
| 6,224,871 | B1 | 5/2001 | Hastings |
| 6,224,877 | B1 | 5/2001 | Gaikar |
| 6,235,287 | B1 | 5/2001 | Weidner |
| 6,245,350 | B1 | 6/2001 | Amey |
| 6,344,475 | B1 | 2/2002 | Caplan |
| 6,576,273 | B2 | 6/2003 | Madsen |
| 6,592,896 | B2 | 7/2003 | Rosenbloom |
| 6,827,951 | B2 | 12/2004 | Newmark |
| 6,942,881 | B2 | 9/2005 | Madsen |
| 6,982,099 | B2 | 1/2006 | Newmark |
| 6,991,814 | B2 | 1/2006 | Ray |
| 7,037,524 | B2 | 5/2006 | Gow |
| 7,041,321 | B2 | 5/2006 | Newmark |
| 7,067,159 | B2 | 6/2006 | Newmark |
| 7,070,816 | B2 | 7/2006 | Newmark |
| 7,736,679 | B2 * | 6/2010 | Antony .............. A61K 36/9066 424/756 |
| 7,879,373 | B2 * | 2/2011 | Antony .............. A61K 36/9066 424/756 |
| 7,883,728 | B2 * | 2/2011 | Antony .............. A61K 36/9066 424/725 |
| 8,153,172 | B2 * | 4/2012 | Antony .............. A61K 36/9066 424/756 |
| 8,197,869 | B2 * | 6/2012 | Antony .............. A61K 36/9066 424/725 |
| 8,329,233 | B2 * | 12/2012 | Antony .............. A61K 36/9066 424/443 |
| 8,623,431 | B2 * | 1/2014 | Antony .............. A61K 36/9066 424/756 |
| 8,859,020 | B2 * | 10/2014 | Antony .............. A61K 36/9066 424/725 |
| 8,895,087 | B2 * | 11/2014 | Antony .............. A61K 36/9066 424/756 |
| 8,993,013 | B2 * | 3/2015 | Antony .............. A61K 36/9066 424/725 |
| 9,492,402 | B2 * | 11/2016 | Antony .................. A61K 31/12 |
| 9,861,677 | B2 * | 1/2018 | Antony .............. A61K 36/9066 |
| 9,878,040 | B2 * | 1/2018 | Antony .................. A61K 47/08 |
| 2002/0136786 | A1 | 9/2002 | Newmark |
| 2004/0247664 | A1 | 12/2004 | Dreja |
| 2005/0123632 | A1 | 6/2005 | Chen |
| 2006/0051438 | A1 | 3/2006 | Ray |

FOREIGN PATENT DOCUMENTS

| | | |
|---|---|---|
| CN | 1491089 A | 4/2004 |
| CN | 1548121 A | 11/2004 |
| EP | 1465646 A1 | 10/2004 |
| IN | 457/RQ/CHE/2003 | 7/2005 |
| IN | 200430 | 5/2006 |
| JP | 2000-228966 A | 8/2000 |
| JP | 2004524304 A | 8/2004 |
| JP | 2004331539 A | 11/2004 |
| WO | WO 2000/059523 A1 | 10/2000 |
| WO | WO 2001/000201 A1 | 1/2001 |
| WO | WO 2002/032444 A1 | 4/2002 |
| WO | WO 02074295 A1 | 9/2002 |
| WO | WO 03/049753 A1 | 6/2003 |
| WO | WO 03/075685 A1 | 9/2003 |

OTHER PUBLICATIONS

Jayaprakasha, GK, Jena, BS, Negi, PS, and Sakariah, KK, Evaluation of Antioxidant Activities and Antimutagenicity of Turmeric Oil: A Byproduct from Curcumin Production, Biosciences, 57(9/10):828-835 (2002).

Kelloff, GJ, Crowell, JA, Hawk ET, Steele, VE, Lubet, RA, Boone, CW, Covey JM, Doody, LA, Omenn, GS, Greenwald, P, Hong, WK, Parkinson, DR, Bagheri, D, Baxter, GT, Blunden, M, Doeltz, MK, Eisenhauer, KM, Johnson, K, Knapp, GG, Longfellow, DG, Malone, WF, Nayfield, SG, Seifried, HE, SWALL, LM, and Sigman, CC, Strategy and Planning for Chemopreventive Drug Development: Clinical Development Plans II, Journal of Cellular Biochemistry, 26S: 54-71 (1996).

Rao, CV, Rivenson, A, Simi, B, and Reddy, BS, Chemoprevention of Colon Carcinogenesis by Dietary Curcumin, a Naturally Occuring Plant Phenolic Compound, Cancer Research, 55:259-266 (1995).

Subramanian, M, Sreejayan, Rao, MNA, Devasagayam, TPA, and Singh, BB, Diminution of Singlet Oxygen-Induced DNA Damage by Curcumin and Related Antioxidants, Mutation Research, 311:249-255 (1994).

Tennesen, HH, and Greenhill, JV, Studies on Curcumin and Curcuminoids, XXII: Curcumin as a Reducing Agent and as a Radical Scavenger, International Journal of Pharmaceutics, 87:79-87 (1992).

Reddy, ACP, and Lokesh, BR, Studies on the Inhibitory Effects of Curcumin and Eugenol on the Formation of Reactive Oxygen Species and The Oxidation of Ferrous Iron, Molecular and Cellular Biochemistry, 137:1-8 (1994).

Donatus, IA, Sardjoko, and Vermeulen, NPE, Cytotoxic and Cytoprotective Activities of Curcumin, Biochemical Pharmacology, 39(12):1869-1875 (1990).

Sharma, SC, Mukhtar, H, Sharma, SK, Murti, CRK, Lipid Peroxide Formation in Experimental Inflammation, Biochemical Pharmacology, 21:1210-1214 (1972).

Liu, J-Y, Lin, S-J, and Lin, J-K, Inhibitory Effects of Curcumin on Protein Kinase C Activity Induced by 12-O-tetradecanoyl-Phorbol-13-Acetate in NIH 3T3 Cells, Carcinogenesis, 14(5):857-861 (1993).

Huang, T-S, Lee, S-C, and Lin, J-K, Suppression of c-Jun/ AP-1 Activation by an inhibitor of Tumor Promotion in Mouse Fibroblast Cells, Proc. Natl. Acad. Sci. U.S.A., 88:5292-5296 (1991).

Huang, M-T, Lysz, T, Ferraro, T, and Conney, AH, Inhibitory Effects of Curcumin on Tumor Promotion and Arachidonic Acid Metabolism in Mouse Epidermis, Cancer Chemoprevention, pp. 375-391 (1992), CRC Press, Inc.

Huang, M-T, Lysz, T, Ferraro, T, Abidi, TF, Laskin, JD, and Conney, AH, Inhibitory Effects of Curcumin on In Vitro Lipoxygenase and Cyclooxygenase Activities in Mouse Epidermis, Cancer Research, 51:813-819 (1991).

Plummer, SM, Holloway, KA, Manson, MM, Munks, RJL, Kaptein, A, Farrow, S, and Howells, L, Inhibition of Cyclo-Oxygenase 2 Expression in Colon Cells by the Chemopreventive Agent Curcumin Involves Inhibition of NF-KB Activation Via The NIK/IKK Signalling Complex, Oncogene, 18:6013-6020 (1999).

Funk, CD, Funk, LB, Kennedy, ME, Pong, AS, and Fitzgerald, GA, Human Platelet/ Erythroleukemia Cell Prostaglandin G/H Synthase: cDNA Cloning, Expression, and Gene Chromosomal Assignment, FASEB Journal, 5:2304-2312 (1991).

(56) References Cited

OTHER PUBLICATIONS

Subbaramaiah, K, Telang, N, Ramonetti, JT, Araki, R, Devito, B, Weksler, BB, and Dannenberg, AJ, Transcription of Cyclooxygenase-2 Is Enhanced in Transformed Mammary Epithelial Cells, Cancer Research, 56:4424-4429 (1996).
Dubois, RN, Awad, J, Morrow, J, Roberts, LJ, and Bishop, PR, Regulation of Eicosanoid Production and Mitogenesis in Rat Intestinal Epithelial Cells by Transforming Growth Factor -α and Phorbol Ester, J. Clin. Invest., 93:493-498 (1994).
Kelley, DJ, Mestre, JR, Subbaramaiah, K, Sacks, PG, Schantz, SP, Tanabe, T, Inoue, H, Ramonetti, JT, and Dannenberg, AJ, Benzo[a]pyrene Up-Regulates Cyclooxygenase-2 Gene Expression in Oral Epithelial Cells, Carcinogenesis, 18(4):795-799 (1997).
Huang, M-T, Smart, RC, Wong, C-Q, and Conney, AH, Inhibitory Effect of Curcumin, Chlorogenic Acid, Caffeic Acid, and Ferulic Acid on Tumor Promotion in Mouse Skin by 12-O-Tetradecanoylphorbol-B-13-Acetate, Cancer Research, 48:5941-5946 (1988).
Asai, A and Miyazawa, T, Occurence of Orally Administered Curcuminoid as Glucuronide and Glucuronide/Sulfate Conjugates in Rat Plasma, Life Sciences, 67:2785-2793 (2000).
Ravindranath, V, and Chandrasekhara, N, In Vitro Studies on The Intestinal Absorption of Curcumin in Rats, Toxicology, 20:251-257 (1981).
Limtrakul, P, Lipigorngoson, S, Namwong, O, Apisariyakul, A, and Dunn, FW, Inhibitory Effect of Dietary Curcumin on Skin Carcinogenesis in Mice, Cancer Letters, 116:197-203 (1997).
Inano, H, and Onoda, M, Prevention of Radiation-Induced Mammary Tumors, Int. J. Radiation Oncology Biol. Phys., 52(1):212-223 (2002).
Inano, H, and Onoda, M, Radioprotective Action of Curcumin Extracted From Curcuma Longa Linn: Inhibitory Effect on Formation of Urinary 8-Hydroxy-2'-Deoxyguanosine, Tumorigenesis, But Not Mortality, Induced by γ-Ray Irradiation, Int. J. Radiation Oncology Biol. Phys., 53(3):735-743 (2002).
Shoba, G, Joy, D, Joseph, T, Majeed, M, Rajendran, R, and Srinivas, PSSR, Influence of Piperine on the Pharmacokinetics of Curcumin in Animals and Human Volunteers, Planta Medica, 64:353-356 (1998).
Began, G, Sudharshan, E, Sankar, KU, and Rao, AGA, Interaction of Curcumin With Phosphatidylcholine: A Spectrofluorometric Study, J. Agric. Food Chem, 47:4992-4997 (1999).
Lantz, RC, Chen, GJ, Solyom, AM, Jolad, SD, and Timmermann, BN, The Effect of Turmeric Extracts on Inflammatory Mediator Production, Phytomedicine 12:445-452 (2005).
Nishiyama, T, Mae, T, Kishida, H, Tsukagawa, M, Mimaki, Y, Kuroda, M, Sashida, Y, Takahashi, K, Kawada, T, Nakagawa, K, and Kitahara, M, Curcuminoids and Sesquiterpenoids in Turmeric (*Curcuma longa* L) Suppress an Increase in Blood Glucose Level in Type 2 Diabetic KK-A$^y$ mice, J. Agric. Food Chem, 53:959-963 (2005).
Li, L, Braiteh, FS, and Kurzrock, R, Liposome-Encapsulated Curcumin, In Vitro and In Vivo Effects on Proliferation, Apoptosis, Signaling, and Angiogenesis, Cancer, 104(6):1322-1331 (2005).
Kumar, V, Lewis, SA, Mutalik, S, Shenoy, DB, Venkatesh and Udupa, N, Biodegradable Microspheres of Curcumin For Treatment of Inflammation, Indian J Physical Pharmacol, 46(2): 209-217 (2002).
Ammon, HPT, and Wahl, MA, Pharmacology of Curcuma Longa, Planta Med, 57:1-7, (1991).
Ravindranath, V, and Chandrasekhara, N, Absorption and Tissue Distribution of Curcumin in Rats, Toxicology, 16: 259-265 (1980).
Wahlstrom, B and Blennow, G, A Study on the Fate of Curcumin in the Rat, Acta Pharmacol. et Toxicol., 43:86-92 (1978).
Monograph, *Curcuma longa* (Turmeric), Alternative Medicine Review, vol. 6 (Supplement): S62-S66 (2001).
Piyachaturawat, P, Glinsukon, T, and Toskulkao, C, Acute and Subacute Toxicity of Piperine in Mice, Rats and Hamsters, Toxicology Letters, 16:351-359 (1983).
Matsuo, T, Toyota, A, Kanamori, H, Nakamura, K, Katsuki, S, Sekita, S, and Satake, M, Constituents of Representative Curcuma and Estimation of *Curcuma* Species in Health Foods, Bulletin of the Hiroshima Prefectural Institute of Public Health and Environment, 10:7-13 (2002), Japan Science and Technology Agency.
Kawamori, T, Lubet, R, Steele, VE, Kelloff, GJ, Kaskey, RB, Rao, CV, and Reddy, BS, Chemopreventive Effect of Curcumin, A Naturally Occuring Anti-Inflammatory Agent, During the Promotion/Progression Stages of Colon Cancer, Cancer Res., 59:597-601 (1999), American Association for Cancer Research.
Mahmoud, NN, Carothers, AM, Grunberger, D, Bilinski, RT, Churchill, MR, Martucci, C, Newmark, HL, and Bertagnolli, MM, Plant Phenolics Decrease Intestinal Tumors in an Animal Model of Familial Adenomatous Polyposis, Carcinogenesis, 21(5):921-927 (2000), Oxford University Press.
Zhang, F, Altorki, NK, Mestre, JR, Subbaramaiah, K, and Dannenberg, AJ, Curcumin Inhibits Cyclooxygenase-2 transcription in Bile Acid- and Phorbol Ester-Treated Human Gastrointestinal Epithelial Cells, Carcinogenesis, 20(3): 445-451 (1999), Oxford University Press.
Ireson, C, Orr, S, Jones, DJL, Verschoyle, R, Lim, C-K, Luo, J-L, Howells, L, Plummer, S, Jukes, R, Williams, M, Steward, WP, and Gescher, A, Characterization of Metabolites of the Chemopreventive Agent Curcumin in Human and Rat Hepatocytes and in the Rat in Vivo, and Evaluation of Their Ability to Inhibit Phorbol Ester-Induced Prostaglandin $E_2$ Production, Cancer Res., 61: 1058-1064 (2001), American Association for Cancer Research.
Sharma, RA, McLelland, HR, Hill, KA, Ireson CR, Euden, SA, Manson MM, Pirmohamed, M, Marnet, LJ, Gescher, AJ, and Steward, WP, Pharmacodynamic and Pharmacokinetic Study of Oral Curcuma Extract in Patients with Colorectal Cancer, Clin. Cancer Res., 7:1894-1900 (2001), American Association for Cancer Research.
Pan, M-H, Huang, T-M, and Lin, J-K, Biotransformation of Curcumin Through Reduction and Glucoronidation in Mice, Drug Metabolism and Disposition, 27(1):486-494 (1999), American Society for Pharmacology and Experimental Therapeutics.
Ireson, CR, Jones, DJL, Orr, S, Coughtrie, MWH, Boocock, DJ, Williams, ML, Farmer, PB, Steward, WP, and Gescher, AJ, Metabolism of the Cancer Chemopreventive Agent Curcumin in Human and Rat Intestine, Cancer Epidemiology, Biomarkers & Prevention, 11:105-111 (2002), American Association for Cancer Research.
Perkins, S, Verschoyle, RD, Hill, K, Parveen, I, Threadgill, MD, Sharma, RA, Williams, ML, Steward, WP, and Gescher, AJ, Chemopreventive Efficacy and Pharmacokinetics of Curcumin in the Min/+ Mouse, a Model of Familial Adenomatous Polyposis, Cancer Epidemiology, Biomarkers & Prevention, 11: 535-540 (2002), American Association for Cancer Research.
Chuang, SE, Kuo, ML, Hsu, CH, Chen, CR, Lin, JK, Lai, GM, Hsieh, CY, and Cheng, AL, Curcumin-Containing Diet Inhibits Diethylnitrosamine-Induced Murine Hepatocarcinogenesis, Carcinogenesis, 21(2):331-335 (2000), Oxford University Press.
Inano, H, Onoda, M, Inafuku, N, Kubota, M, Kamada, Y, Osawa, T, Kobayashi, H, and Wakabayashi, K, Potent Preventive Action of Curcumin on Radiation-Induced Initiation of Mammary Tumorigenesis in Rats, Carcinogenesis, 21(10): 1835-1841 (2000), Oxford University Press.
Garcea, G, Berry, DP, Jones, DJL, Singh, R, Dennison, AR, Farmer, PB, Sharma, RA, Steward, WP, and Gescher, AJ, Consumption of the Putative Chemopreventive Agent Curcumin by Cancer Patients: Assessment of Curcumin Levels in the Colorectum and their Pharmacodynamic Consequences, Cancer Epidemiology, Biomarkers & Prevention, 14(1) 120-125 (2005), American Association for Cancer Research.
Govindarajan, VS and Stahl, WH, Turmeric—Chemistry, technology, and Quality, CRC Critical Reviews in Food Science and Nutrition, 12(3):199-301 (1980).
Sharma RA, Ireson, CR, Verschoyle, RD, Hill, KA, Williams, ML, Leuratti, C, Manson, MM, Marnett, LJ, Steward, WP, and Gescher, A, Effects of Dietary Curcumin on Glutathione S-Transferase and Malondialdehyde-DNA Adducts in Rat Liver and Colon Mucosa: Relationship with Drug Levels, Clinical Cancer Research, 7:1452-1458 (2001).
Sharma, RA, Euden, SA, Platton, SL, Cooke, DN, Shafayat, A, Hewitt, HR, Marczylo, TH, Morgan, B, Hemigway, D, Plummer,

(56) References Cited

OTHER PUBLICATIONS

SM, Pirmohamed, M, Gescher, AJ and Steward, WP, Phase I Clinical Trial of Oral Curcumin: Biomarkers of Systemic Activity and Compliance, Clinical Cancer Research, vol. 10, 6847-6854 (Oct. 15, 2004).
Hong CH, Kim Y, and Lee SK, Sesquiterpenoids from the Rhizome of Curcuma Zedoaria, Arch Pharm Res., 24(5): 424-426 (2001).
G. Scapagnini, R Foresti, V. Calabrese, AM Giuffrida Stella, CJ Green, and R. Motterlini, Caffeic Acid Phenethyl Ester and Curcumin: A Novel Class of Heme Oxygenase-1 Inducers, Molecular Pharmacology, 61(3):554-561 (2002).
Supplementary European Search Report (3 pages) dated Dec. 14, 2009.
Anna Carolina CM Manzan, Toniolo FS, Bredow E, and Povh, NP, Extraction of Essential Oil and Pigments from Curcuma longa [L.] by Steam Distillation and Extraction with Volatile Solvents, Journal of Agricultural and Food Chemistry, 51:6802 6807 (2003).
Negi PS, Jayaprakasha GK, Rao LJM, and Sarkaria KK, Antibacterial Activity of Turmeric Oil: A Byproduct from Curcumin Manufacture, J. Agric. Food Chem., 47:4297-4300 (1999).
Hong CH, Noh MS, Lee WY and Lee SK, Inhibitory Effects of Natural Sesquiterpenoids Isolated from the Rhizomes of Curcuma zedoaria on Prostaglandin $E_2$ and Nitric Oxide Production, Planta Med, 68:545-547 (2002).
Craig WJ, The Golden Touch of Turmeric, Vibrant Life, 19 (3): 38-39 (2003), ProQuest Central.
Sandur SK, Pandey MK, Sung B, Ahn KS, Murakami A, Sethi G, Limtrakul P, Badmaev V and Aggarwal BB, Curcumin, Demethoxycurcumin, Bisdemethoxycurcumin, Tetrahydrocurcumin and Turmerones Differentially Regulate Anti-Inflammatory and Anti-Proliferative Responses Through a ROS-Independent Mechanism, Carcinogenesis Advance Access, originally published online on May 23, 2007, Carcinogenesis 28(8):1765-1773 (2007); doi:10.1093/carcin/bgm123.
Asche SL and Thakkar SK, Oil Extraction Increases Curcumin Availability from Turmeric Sources, FASEB Journal, 18 (4-5): Abstract 115.7 (2004).
Fujii Masami et al., Ingredient that improves bio-availability of curcumin, latest edition of Natural Food coloring material, Korin Publishing Co., Ltd., pp. 168-172 (2001).
Janaki, N and Bose, JL, An Improved Method for the Isolation of Curcumin From Turmeric, Curcuma longa, L, Journal of Indian Chemical Society, 44 (11):985-986 (1967).
Krishnamurthy, N, Mathew, AG, Nambudiri, ES, Shivashankar, S, Lewis, YS, and Natarajan, CP, Oil and Oleoresin of Turmeric, Trop. Sci., 18(1):37-45 (1976).
Huang, M-T, Lou, Y-R, Ma, W, Newmark, HL, Reuhl, KR and Conney, AH, Inhibitory Effects of Dietary Curcumin on Forestomach, Duodenal, and Colon Carcinogenesis in Mice, Cancer Research, 54:5841-5847 (1994).
Pabon, HJJ, A Synthesis of Curcumin and Related Compounds, Recueil, 83:379-386 (1964).
Xu, Y, Ku, B-S, Yao, H-Y, Lin, Y-H, Ma, X, Zhan G, Y-H, Li, X-J, Antidepressant effects of curcumin in the forced swim test and olfactory bulbectomy models of depression in rats, Pharmacology Biochemistry and Behavior, 82(1): 200-206 (2005), Elsevier, Inc.
Yu, ZF, Kong, LD, and Chen, Y, Antidepressant activity of aqueous extracts of Curcuma longa in mice, Journal of Ethnopharmacology, 83(1-2): 161-165 (2002), Elsevier Science Ireland Ltd.
Funk, JL, Oyarzo, JN, Frye, JB, Chen, G, Lantz, RC, Jolad, SD, Solyom, AM, and Timmermann, BN, Turmeric extracts containing curcuminoids prevent experimental rheumatoid arthritis, Journal of Natural Products, 69(3): 351-355 (2006), American Chemical Society and American Society of Pharmacology.
Begum, AN, Jones, MR, Lim, GP, Morihara, T, Kim, P, Heath, DD, Rock, CL, Pruitt, MA, Yang, F, Hudspeth, B, Hu, S, Faull, KF, Teter, B, Cole, GM, and Frautschy, SA, Curcumin structure-function, bioavailability, and efficacy in models of neuroinflammation and Alzheimer's disease, Journal of Pharmacology and Experimental Therapeutics, 326(1): 196-208 (2008).
Zhang, L, Fiala, M, Cashman, J, Sayre, J, Espinosa, A, Mahanian, M, Zaghi, J, Badmaev, V, Graves, MC, Bernard, G and Rosenthal, M, Curcuminoids enhance amyloid-β uptake by macrophages of Alzheimer's disease patients, Journal of Alzheimer's Disease, 10(1):1-7 (2006), IOS Press and the authors.
Eight (8) pages of Supplementary European Search Report of Sep. 10, 2013 in Application No. EP 11765176.
Hashibe, M, Sankaranarayanan, R, Thomas, G, Kuruvilla, B, Mathew, B, Somanathan, T, Parkin,DM and Zhang, ZF, Alcohol drinking, body mass index and the risk of oral Leukoplakia in an Indian population, Int. J. Cancer, 88: 129-134 (2000).
Kaur, J, Srivastava, A, Ralhan, R, Over expression of p53 protein in betel and tobacco related human oral dysplasia and squamous cell carcinoma in India, Int. J. Cancer: Aug. 1; 58(3):3405. (1994).
Sol, S, Bilimoria, KF, Bhargava, K, Mani, NJ, Shah, RA, Cytologic, histologic and clinical correlations of precancerous and cancerous oral lesions in 57,518 industrial workers of Gujarat, India, Acta Cytol. Mar.- Apr. 1977;21 (2):196-8.
Silverman, S, Bhargava, K, Smith, LW, Malaowalla, AM, Malignant transformation and natural history of oral leukoplakia in 57,518 industrial workers of Gujarat, India, Cancer.Oct.; 38(4):1790-5 (1976).
Danely,P, Slaughterm, D, Harry,W, Southwickm, D, Walter Smejkal, MD, Field Cancerization in oral stratified Squamous epithelium, Sixth Annual Cancer Symposium of the James Ewing Society, Mar. 7, 1953.
Saleheen, D, Ali, SA, Ashfaq, K, Siddiqui, AA, Agha, A and Yasinzai, MM, Latent activity of curcumin against Leishmaniasis in Vitro, Biol. Pharm. Bull. 25(3): 386-389 (2002).
Koide, T, Nose, M, Ogihara, Y, Yoshisada Yabu, Y, and Ohta, N, Leishmanicidal effect of curcumin in Vitro, Biol. Pharm. Bull. 25(1): 131-133 (2002).
Gomes,DCE, Alegrio,LV, Lima,MEF, Leon,LL,Araujo,CAC, Synthetic derivatives of curcumin and their activity against Leishmania amazonensis, Arzneim-Forsch/Drug Res.52,No. 2: 120-124 (2002).
Wu, NC, Safety and Anti-Inflammatory Activity of Curcumin: A Component of Tumeric (Curcuma longa), The Journal of Alternative and Complementary Medicine vol. 9, No. 1, pp. 161-168 (2003).
Strong, MS, I.J., Vaughan, CW, Field cancerization in the aerodigestive tract—its etiology, manifestation, and significance, J Otolaryngol, 13(1): p. 1-6 (1984).
Pandey, M, Thomas, G, Somanathan, T, Sankaranarayanan, R, Abraham, E K., Jacob, B J, and Mathew, B, Evaluation of surgical excision of non-homogeneous oral leukoplakia in a screening intervention trial, Kerala, India. Oral Oncol,. 37: p. 103-9 (2001).
Grosso C, Valentao P, Ferreres F and Andrade PB, The use of flavonoids in central nervous system disorders, Current Medicinal Chemistry, 20:1-26 (2013).
Bergman J, Midownik C, Bersudsky Y, Sokolik S, Lerner PP, Krenin A, Polakiewicz J and Lerner V, Curcumin as an Add-On to Antidepressive Treatment: A Randomized, Double-Blind, Placebo-Controlled, Pilot Clinical Study, Clinical Neuropharm, 36:73-77 (2013).
Guidance for Industry Estimating the Maximum Safe Starting Dose in Initial Clinical Trials for Therapeutics in Adult Healthy Volunteers; U.S. Department of Health and Human Services Food and Drug Administration Center for Drug Evaluation and Research (CDER) (referred to as "Guidance"), J:\!GUIDANC\5541fnlcln1.doc, pp. 1-27 (Jul. 6, 2005).
Antony, B, Benny, M, Rao, SB, Enhancing the Absorption of Curcuminoids, Spice India; 23-26 (2005).
Benny, M, Antony, B, Bioavailability of Biocurcumax™ (BCM-095™), Spice India;11-15(2006).
Antony, B, Merina, B, Iyer, VS, Judy, N, Lennertz, K, Joyal, S, A pilot cross-over study to evaluate human oral bioavailability of BCM-95® CG (Biocurcumax™), a novel bioenhanced preparation of curcumin, Indian journal of pharmaceutical sciences, 70(4):445(2008).

* cited by examiner

| | Mean blood concentration of curcuminoids (ng/gm of blood) | | | | | | | | | | | | | | | | | | | | |
|---|---|---|---|---|---|---|---|---|---|---|---|---|---|---|---|---|---|---|---|---|---|
| | Regular turmeric extract (Example 1) | | | Curcuminoids blended with essential oil of turmeric having 45% Ar-turmerone in 10:1 ratio (Example 3) | | | Curcuminoids blended with essential oil of turmeric having 45% Ar-turmerone in 12:1 ratio (Example 4) | | | Sustained release formulation of curcuminoids blended with essential oil of turmeric having 45% Ar-turmerone in 10:1 ratio coated with ethyl cellulose in 10:1 ratio (Example 5) | | | Sustained release formulation of curcuminoids blended with essential oil of turmeric having 45% Ar-turmerone in 12:1 ratio coated with ethyl cellulose in 10:1 ratio (Example 6) | | | Sustained release formulation of Regular turmeric extract coated with ethyl cellulose in 10:1 ratio (Example 7) | | |
| Time (hours) | Curcumin | DMC | BDMC | Curcumin | DMC | BDMC | Curcumin | DMC | BDMC | Curcumin | DMC | BDMC | Curcumin | DMC | BDMC | Curcumin | DMC | BDMC |
| 0 | ND | ND | ND | ND | ND | ND | ND | ND | ND | ND | ND | ND | ND | ND | ND | ND | ND | ND |
| 1 | 8.2 | ND | ND | 11.2 | ND | ND | 22.3 | ND | ND | 60.3 | 43.5 | 14.8 | 74.5 | 58.5 | 17.4 | 13.6 | ND | ND |
| 2 | 14.5 | ND | ND | 26.2 | ND | ND | 81.3 | ND | ND | 97.4 | 69.2 | 16.9 | 112.3 | 84.6 | 19.8 | 20.8 | ND | ND |
| 4 | 10.2 | ND | ND | 80.3 | ND | ND | 102.1 | ND | ND | 133.4 | 94.7 | 13.9 | 162.5 | 102.8 | 18.5 | 14.4 | ND | ND |
| 6 | 3.2 | ND | ND | 14.1 | ND | ND | 26.2 | ND | ND | 83.7 | 88.9 | 13.5 | 128.5 | 98.4 | 16.8 | 5.6 | ND | ND |
| 8 | ND | ND | ND | 7.1 | ND | ND | 11.5 | ND | ND | 78.3 | 41.2 | 11.4 | 98.6 | 73.5 | 15.2 | ND | ND | ND |
| 12 | ND | ND | ND | ND | ND | ND | ND | ND | ND | 42.9 | 52.3 | 12.1 | 92.5 | 64.6 | 13.6 | ND | ND | ND |
| 24 | ND | ND | ND | ND | ND | ND | ND | ND | ND | 56.5 | 32.1 | 3.1 | 81.2 | 52.3 | 9.8 | ND | ND | ND |
| 27 | ND | ND | ND | ND | ND | ND | ND | ND | ND | 49.6 | 30.5 | ND | 64.3 | 35.6 | ND | ND | ND | ND |
| 30 | ND | ND | ND | ND | ND | ND | ND | ND | ND | 14.2 | ND | ND | 43.3 | 18.4 | ND | ND | ND | ND |

*DMC = Demethoxy curcumin; BDMC = Bis-demethoxy curcumin; ND = Not detected

Fig. 26

| Time (hours) | Mean blood concentration of curcuminoids (ng/gm of blood) ||||||||||||||||
| | Regular turmeric extract (Example 1) ||| Curcuminoids blended with essential oil of turmeric having 45% Ar-turmerone in 10:1 ratio (Example 3) ||| Curcuminoids blended with essential oil of turmeric having 45% Ar-turmerone in 12:1 ratio (Example 4) ||| Sustained release formulation curcuminoids blended with essential oil of turmeric having 45% Ar-turmerone in 10:1 ratio coated with ethyl cellulose in 500:25 ratio (Example 8) ||| Sustained release formulation curcuminoids blended with essential oil of turmeric having 45% Ar-turmerone in 12:1 ratio coated with ethyl cellulose in 500:25 ratio (Example 9) ||| Sustained release formulation Regular turmeric extract coated with ethyl cellulose in 500:25 (Example 10) |||
| | Curcumin | DMC | BDMC | Curcumin | DMC | BDMC | Curcumin | DMC | BDMC | Curcumin | DMC | BDMC | Curcumin | DMC | BDMC | Curcumin | DMC | BDMC |
|---|---|---|---|---|---|---|---|---|---|---|---|---|---|---|---|---|---|---|
| 0 | ND | ND | ND | ND | ND | ND | ND | ND | ND | ND | ND | ND | ND | ND | ND | ND | ND | ND |
| 1 | 8.2 | ND | ND | 11.2 | ND | ND | 22.3 | ND | ND | 62.8 | 44.4 | 13.4 | 72.4 | 60.5 | 16.2 | 12.8 | ND | ND |
| 2 | 14.5 | ND | ND | 26.2 | ND | ND | 81.3 | ND | ND | 99.1 | 66.2 | 15.6 | 110.2 | 83.3 | 19.3 | 21.1 | ND | ND |
| 4 | 10.2 | ND | ND | 80.3 | ND | ND | 102.1 | ND | ND | 138.1 | 90.8 | 13.4 | 158.5 | 108.1 | 18.2 | 14.2 | ND | ND |
| 6 | 3.2 | ND | ND | 14.1 | ND | ND | 26.2 | ND | ND | 82.1 | 56.4 | 14.6 | 125.1 | 101.4 | 17.1 | 6.2 | ND | ND |
| 8 | ND | ND | ND | 7.1 | ND | ND | 11.5 | ND | ND | 83.3 | 66.6 | 9.8 | 92.6 | 78.5 | 15.6 | ND | ND | ND |
| 12 | ND | ND | ND | ND | ND | ND | ND | ND | ND | 48.4 | 39.3 | 9.8 | 88.4 | 62.6 | 12.9 | ND | ND | ND |
| 24 | ND | ND | ND | ND | ND | ND | ND | ND | ND | 67.4 | 47.2 | 3.4 | 71.4 | 54.7 | 9.4 | ND | ND | ND |
| 27 | ND | ND | ND | ND | ND | ND | ND | ND | ND | 37.3 | 31.2 | ND | 60.3 | 33.6 | ND | ND | ND | ND |
| 30 | ND | ND | ND | ND | ND | ND | ND | ND | ND | 10.6 | ND | ND | 39.4 | 20.4 | ND | ND | ND | ND |

*DMC=Demethoxycurcumin; BDMC=Bis-demethoxycurcumin; ND=Not detected

Fig. 27

| Time (hours) | Mean blood concentration of curcuminoids (ng/gm of blood) ||||||||||||||||
|---|---|---|---|---|---|---|---|---|---|---|---|---|---|---|---|---|
| | Regular turmeric extract (Example 1) ||| Curcuminoids blended with essential oil of turmeric having 45% Ar-turmerone in 10:1 ratio (Example 3) ||| Curcuminoids blended with essential oil of turmeric having 45% Ar-turmerone in 12:1 ratio (Example 4) ||| Sustained release formulation of Curcuminoids blended with essential oil of turmeric having 45% Ar-turmerone in 10:1 ratio coated with shellac in 10:1 ratio (Example 17) ||| Sustained release formulation of Curcuminoids blended with essential oil of turmeric having 45% Ar-turmerone in 12:1 ratio coated with shellac in 10:1 ratio (Example 18) ||| Sustained release formulation of regular turmeric extract coated with shellac in 10:1 ratio (Example 20) |||
| | Curcumin | DMC | BDMC | Curcumin | DMC | BDMC | Curcumin | DMC | BDMC | Curcumin | DMC | BDMC | Curcumin | DMC | BDMC | Curcumin | DMC | BDMC |
| 0 | ND | ND | ND | ND | ND | ND | ND | ND | ND | ND | ND | ND | ND | ND | ND | ND | ND | ND |
| 1 | 7.5 | ND | ND | 13.5 | ND | ND | 18.9 | ND | ND | 58.7 | 40.1 | 12.4 | 75.4 | 52.3 | 16.7 | 8.5 | ND | ND |
| 2 | 13.1 | ND | ND | 28.4 | ND | ND | 78.4 | ND | ND | 95.4 | 67.4 | 15.2 | 101.4 | 82.1 | 18.4 | 15.4 | ND | ND |
| 4 | 9.4 | ND | ND | 89.6 | ND | ND | 110.2 | ND | ND | 142.1 | 95.9 | 14.2 | 169.8 | 106.7 | 17.1 | 10.2 | ND | ND |
| 6 | ND | ND | ND | 18.6 | ND | ND | 28.7 | ND | ND | 88.7 | 79.6 | 13.7 | 119.3 | 93.4 | 15.8 | ND | ND | ND |
| 8 | ND | ND | ND | 9.5 | ND | ND | 10.4 | ND | ND | 69.4 | 55.4 | 10.2 | 101.5 | 75.8 | 14.7 | ND | ND | ND |
| 12 | ND | ND | ND | ND | ND | ND | ND | ND | ND | 50.4 | 32.3 | 9.5 | 88.6 | 61.8 | 13.1 | ND | ND | ND |
| 24 | ND | ND | ND | ND | ND | ND | ND | ND | ND | 41.2 | 25.4 | 3.1 | 74.2 | 49.6 | 8.4 | ND | ND | ND |
| 27 | ND | ND | ND | ND | ND | ND | ND | ND | ND | 32.4 | 12.3 | ND | 60.1 | 31.2 | ND | ND | ND | ND |
| 30 | ND | ND | ND | ND | ND | ND | ND | ND | ND | 10.4 | ND | ND | 39.4 | 19.4 | ND | ND | ND | ND |

*DMC = Demethoxy curcumin; BDMC = Bis-demethoxy curcumin; ND = Not detected

Fig. 28

| Time (hours) | Mean blood concentration of curcuminoids (ng/gm of blood) ||||||||||||||||
|---|---|---|---|---|---|---|---|---|---|---|---|---|---|---|---|---|
| | Regular turmeric extract (Example 1) ||| Curcuminoids blended with essential oil of turmeric having 45% Ar-turmerone in 10:1 ratio (Example 3) ||| Curcuminoids blended with essential oil of turmeric having 45% Ar-turmerone in 12:1 ratio (Example 4) ||| Sustained release formulation of Curcuminoids blended with essential oil of turmeric having 45% Ar-turmerone in 10:1 ratio coated with shellac in 14:1 ratio (Example 15) ||| Sustained release formulation of Curcuminoids blended with essential oil of turmeric having 45% Ar-turmerone in 12:1 ratio coated with shellac in 14:1 ratio (Example 16) ||| Sustained release formulation of regular turmeric extract coated with shellac in 14:1 ratio (Example 19) |||
| | Curcumin | DMC | BDMC | Curcumin | DMC | BDMC | Curcumin | DMC | BDMC | Curcumin | DMC | BDMC | Curcumin | DMC | BDMC | Curcumin | DMC | BDMC |
| 0 | ND | ND | ND | ND | ND | ND | ND | ND | ND | ND | ND | ND | ND | ND | ND | ND | ND | ND |
| 1 | 7.5 | ND | ND | 13.5 | ND | ND | 18.9 | ND | ND | 55.1 | 36.8 | 11.2 | 68.5 | 49.5 | 14.8 | 8.6 | ND | ND |
| 2 | 13.1 | ND | ND | 28.4 | ND | ND | 78.4 | ND | ND | 88.4 | 63.4 | 13.5 | 100.4 | 78.9 | 16.4 | 14.2 | ND | ND |
| 4 | 9.4 | ND | ND | 89.6 | ND | ND | 110.2 | ND | ND | 132.4 | 89.3 | 15.2 | 159.4 | 99.8 | 17.6 | 8.6 | ND | ND |
| 6 | ND | ND | ND | 18.6 | ND | ND | 28.7 | ND | ND | 74.3 | 71.2 | 12.4 | 115.4 | 81.4 | 15.1 | ND | ND | ND |
| 8 | ND | ND | ND | 9.5 | ND | ND | 10.4 | ND | ND | 61.3 | 52.1 | 9.4 | 98.6 | 69.3 | 13.9 | ND | ND | ND |
| 12 | ND | ND | ND | ND | ND | ND | ND | ND | ND | 52.3 | 35.4 | 8.5 | 80.2 | 54.2 | 12.4 | ND | ND | ND |
| 24 | ND | ND | ND | ND | ND | ND | ND | ND | ND | 40.2 | 23.2 | 2.2 | 69.3 | 40.8 | 7.4 | ND | ND | ND |
| 27 | ND | ND | ND | ND | ND | ND | ND | ND | ND | 29.6 | 8.5 | ND | 52.1 | 25.3 | ND | ND | ND | ND |
| 30 | ND | ND | ND | ND | ND | ND | ND | ND | ND | 8.1 | ND | ND | 35.2 | 17.6 | ND | ND | ND | ND |

*DMC = Demethoxy curcumin; BDMC = Bis-demethoxy curcumin; ND = Not detected

Fig. 29

| | Initial dose | 1st cross over After two weeks | 2nd cross over After four weeks | 3rd cross over After six weeks | 4th cross over After eight weeks | 5th cross over After ten weeks | 6th cross over After twelve weeks |
|---|---|---|---|---|---|---|---|
| Group 1 (R 101 to 104) | Study drug I | Study drug II | Study drug III | Study drug IV | Study drug V | Study drug VI | Study drug VII |
| Group 2 (R 105 to 108) | Study drug II | Study drug III | Study drug IV | Study drug V | Study drug VI | Study drug VII | Study drug I |
| Group 3 (R 109 to 112) | Study drug III | Study drug IV | Study drug V | Study drug VI | Study drug VII | Study drug I | Study drug II |
| Group 4 (R 113 to 116) | Study drug IV | Study drug V | Study drug VI | Study drug VII | Study drug I | Study drug II | Study drug III |
| Group 5 (R 116 to 120) | Study drug V | Study drug VI | Study drug VII | Study drug I | Study drug II | Study drug III | Study drug IV |
| Group 6 (R 121 to 124) | Study drug VI | Study drug VII | Study drug I | Study drug II | Study drug III | Study drug IV | Study drug V |
| Group 7 (R 125 to 128) | Study drug VII | Study drug I | Study drug II | Study drug III | Study drug IV | Study drug V | Study drug VI |

| Time (hours) | Regular turmeric extract (Example 1) | | | Sustained release formulation of curcuminoids blended with essential oil of turmeric having 45% Ar-turmerone in 12:1 ratio coated with ethyl cellulose in 10:1 ratio (Example 6) | | | Sustained release formulation of regular turmeric extract coated with ethyl cellulose in 10:1 ratio (Example 7) | | | Curcuminoids blended with essential oil of turmeric having 45% Ar-turmerone in 10:1 ratio (Example 3) | | | Curcuminoids blended with essential oil of turmeric having 45% Ar-turmerone in 12:1 ratio (Example 4) | | |
|---|---|---|---|---|---|---|---|---|---|---|---|---|---|---|---|
| | Curcumin | DMC | BDMC | Curcumin | DMC | BDMC | Curcumin | DMC | BDMC | Curcumin | DMC | BDMC | Curcumin | DMC | BDMC |
| 0 | ND | ND | ND | ND | ND | ND | ND | ND | ND | ND | ND | ND | ND | ND | ND |
| 0.5 | ND | ND | ND | 40.9 | 25.6 | 10.2 | ND | ND | ND | 10.3 | ND | ND | 14.5 | ND | ND |
| 1 | 3.1 | ND | ND | 75.2 | 45.6 | 18.6 | 4.1 | ND | ND | 28.6 | ND | ND | 28.9 | ND | ND |
| 2 | 10.5 | ND | ND | 120.6 | 64.2 | 21.5 | 11.2 | ND | ND | 35.9 | ND | ND | 53.6 | ND | ND |
| 3 | 6.2 | ND | ND | 131.1 | 77.1 | 23.4 | 7.1 | ND | ND | 55.6 | ND | ND | 81.2 | ND | ND |
| 4 | 3.2 | ND | ND | 167.8 | 105.3 | 26.3 | 3.7 | ND | ND | 95.6 | ND | ND | 114.5 | ND | ND |
| 6 | ND | ND | ND | 130.2 | 85.2 | 17.4 | ND | ND | ND | 20.6 | ND | ND | 24.4 | ND | ND |
| 8 | ND | ND | ND | 102.5 | 70.3 | 15.1 | ND | ND | ND | 15.3 | ND | ND | 18.4 | ND | ND |
| 10 | ND | ND | ND | 91.2 | 62.4 | 13.2 | ND | ND | ND | ND | ND | ND | ND | ND | ND |
| 12 | ND | ND | ND | 81.5 | 55.7 | 11.4 | ND | ND | ND | ND | ND | ND | ND | ND | ND |
| 16 | ND | ND | ND | 73.4 | 47.3 | 9.8 | ND | ND | ND | ND | ND | ND | ND | ND | ND |
| 20 | ND | ND | ND | 60.7 | 39.6 | 7.9 | ND | ND | ND | ND | ND | ND | ND | ND | ND |
| 24 | ND | ND | ND | 52.6 | 29.6 | 3.5 | ND | ND | ND | ND | ND | ND | ND | ND | ND |
| 28 | ND | ND | ND | 40.4 | 15.4 | 2.2 | ND | ND | ND | ND | ND | ND | ND | ND | ND |
| 32 | ND | ND | ND | 25.6 | 10.3 | ND | ND | ND | ND | ND | ND | ND | ND | ND | ND |
| 36 | ND | ND | ND | 17.7 | ND | ND | ND | ND | ND | ND | ND | ND | ND | ND | ND |
| t1/2 (hours) | 1.04 | | | 7.5 | 6.9 | 5.97 | 1.06 | | | 4.6 | | | 4.9 | | |
| AUC (ng/g) | 23.8 | | | 2508.2 | 1517.9 | 322.6 | 26.9 | | | 333.3 | | | 421.1 | | |

*DMC = Demethoxy curcumin; BDMC = Bis-demethoxy curcumin; ND = Not detected

| | Mean blood concentration of curcuminoids (ng/gm of blood) | | | | | | | | | | | | | |
|---|---|---|---|---|---|---|---|---|---|---|---|---|---|---|
| | Regular turmeric extract (Example 1) | | | Sustained release formulation of curcuminoids blended with essential oil of turmeric having 45% Ar-turmerone in 12:1 ratio coated with shellac in 10:1 ratio (Example 18) | | | Sustained release formulation of regular turmeric extract coated with shellac in 10:1 ratio (Example 20) | | | Curcuminoids blended with essential oil of turmeric having 45% Ar-turmerone in 10:1 ratio (Example 3) | | | Curcuminoids blended with essential oil of turmeric having 45% Ar-turmerone in 12:1 ratio (Example 4) | | |
| Time (hours) | Curcumin | DMC | BDMC | Curcumin | DMC | BDMC | Curcumin | DMC | BDMC | Curcumin | DMC | BDMC | Curcumin | DMC | BDMC |
| 0 | ND | ND | ND | ND | ND | ND | ND | ND | ND | ND | ND | ND | ND | ND | ND |
| 0.5 | ND | ND | ND | 35.6 | 25.3 | 12.8 | ND | ND | ND | 10.3 | ND | ND | 14.5 | ND | ND |
| 1 | 3.1 | ND | ND | 78.6 | 51.2 | 17.4 | 5.2 | ND | ND | 28.6 | ND | ND | 28.9 | ND | ND |
| 2 | 10.5 | ND | ND | 122.3 | 64.5 | 22.1 | 12.4 | ND | ND | 35.9 | ND | ND | 53.6 | ND | ND |
| 3 | 6.2 | ND | ND | 139.6 | 78.1 | 24.6 | 7.5 | ND | ND | 55.6 | ND | ND | 81.2 | ND | ND |
| 4 | 3.2 | ND | ND | 168.5 | 112.4 | 27.8 | 4 | ND | ND | 95.6 | ND | ND | 114.5 | ND | ND |
| 6 | ND | ND | ND | 132.4 | 95.3 | 17.8 | ND | ND | ND | 20.6 | ND | ND | 24.4 | ND | ND |
| 8 | ND | ND | ND | 105.4 | 74.6 | 15.4 | ND | ND | ND | 15.3 | ND | ND | 18.4 | ND | ND |
| 10 | ND | ND | ND | 90.2 | 61.5 | 13.9 | ND | ND | ND | ND | ND | ND | ND | ND | ND |
| 12 | ND | ND | ND | 85.6 | 50.2 | 10.4 | ND | ND | ND | ND | ND | ND | ND | ND | ND |
| 16 | ND | ND | ND | 78.6 | 45.7 | 9.5 | ND | ND | ND | ND | ND | ND | ND | ND | ND |
| 20 | ND | ND | ND | 65.8 | 39.6 | 7.1 | ND | ND | ND | ND | ND | ND | ND | ND | ND |
| 24 | ND | ND | ND | 55.6 | 27.8 | 4.8 | ND | ND | ND | ND | ND | ND | ND | ND | ND |
| 28 | ND | ND | ND | 46.3 | 14.7 | 3 | ND | ND | ND | ND | ND | ND | ND | ND | ND |
| 32 | ND | ND | ND | 30.2 | 10.1 | ND | ND | ND | ND | ND | ND | ND | ND | ND | ND |
| 36 | ND | ND | ND | 21.6 | ND | ND | ND | ND | ND | ND | ND | ND | ND | ND | ND |
| t1/2(hours) | 1.04 | | | 8.2 | 7.4 | 5.89 | 1.1 | | | 4.6 | | | 4.9 | | |
| AUC(ng/gm) | 23.8 | | | 2653.4 | 1560.7 | 330.8 | 29.8 | | | 333.3 | | | 421.1 | | |

*DMC = Demethoxy curcumin; BDMC = Bis-demethoxy curcumin; ND = Not detected

Fig. 32

| Time (hours) | Regular turmeric extract (Example 1) | | | Mean blood concentration of curcuminoids (ng/gm of blood) | | | | | | | | | | | |
|---|---|---|---|---|---|---|---|---|---|---|---|---|---|---|---|
| | | | | Sustained release formulation of curcuminoids blended with essential oil of turmeric having 45% Ar-turmerone prepared as per example 21 | | | Sustained release formulation of curcuminoids blended with essential oil of turmeric having 45% Ar-turmerone prepared as per example 22 | | | Curcuminoids blended with essential oil of turmeric having 45% Ar-turmerone in 10:1 ratio (Example 3) | | | Curcuminoids blended with essential oil of turmeric having 45% Ar-turmerone in 12:1 ratio (Example 4) | | |
| | Curcumin | DMC | BDMC | Curcumin | DMC | BDMC | Curcumin | DMC | BDMC | Curcumin | DMC | BDMC | Curcumin | DMC | BDMC |
| 0 | ND | ND | ND | ND | ND | 0 | 0 | 0 | 0 | ND | ND | ND | ND | ND | ND |
| 0.5 | ND | ND | ND | 19.8 | 15.2 | 10.2 | 17.3 | 13.6 | 11.3 | 11.2 | ND | ND | 13.7 | ND | ND |
| 1 | 2.5 | ND | ND | 42.5 | 38.6 | 28.6 | 39.6 | 30.2 | 24.6 | 24.7 | ND | ND | 30.5 | ND | ND |
| 2 | 11.2 | ND | ND | 75.6 | 62.3 | 39.6 | 70.2 | 55.6 | 34.7 | 39.8 | ND | ND | 48.5 | ND | ND |
| 3 | 6.1 | ND | ND | 115.3 | 100.8 | 46.8 | 110.9 | 92.3 | 39.8 | 60.5 | ND | ND | 84.9 | ND | ND |
| 4 | 3.2 | ND | ND | 145.8 | 123.5 | 53.8 | 131.2 | 114.9 | 50.9 | 90.2 | ND | ND | 115.1 | ND | ND |
| 6 | ND | ND | ND | 158.2 | 142.8 | 62.3 | 145.6 | 132.4 | 58.3 | 17.9 | ND | ND | 22.7 | ND | ND |
| 8 | ND | ND | ND | 186.4 | 162.3 | 55.8 | 169.6 | 142.3 | 51.3 | 13.2 | ND | ND | 16.9 | ND | ND |
| 10 | ND | ND | ND | 163.2 | 149.7 | 40.2 | 152.3 | 132.4 | 39.6 | ND | ND | ND | ND | ND | ND |
| 12 | ND | ND | ND | 145.6 | 130.4 | 35.6 | 140.4 | 116.8 | 31.2 | ND | ND | ND | ND | ND | ND |
| 16 | ND | ND | ND | 125.3 | 101.3 | 29.6 | 114.5 | 100.3 | 27.4 | ND | ND | ND | ND | ND | ND |
| 20 | ND | ND | ND | 115.9 | 89.6 | 23.5 | 101.3 | 82.1 | 20.3 | ND | ND | ND | ND | ND | ND |
| 24 | ND | ND | ND | 96.8 | 71.3 | 19.6 | 94.6 | 66.3 | 17.1 | ND | ND | ND | ND | ND | ND |
| 28 | ND | ND | ND | 88.7 | 59.6 | 17.5 | 89.6 | 52.1 | 15.9 | ND | ND | ND | ND | ND | ND |
| 32 | ND | ND | ND | 70.2 | 45.6 | 14.3 | 68.3 | 40.3 | 12.3 | ND | ND | ND | ND | ND | ND |
| 36 | ND | ND | ND | 55.6 | 35.4 | 10.9 | 53.6 | 30.5 | 9.1 | ND | ND | ND | ND | ND | ND |
| $t_{1/2}$ (hours) | 1.07 | | | 11.8 | 10.4 | 10.2 | 11.4 | 9.9 | 9.2 | 4.5 | | | 4.7 | | |
| AUC(ng/gm) | 23.9 | | | 4002.5 | 3226.1 | 1056.8 | 3752.8 | 2939.7 | 957.1 | 321.9 | | | 414.9 | | |

SUSTAINED RELEASE FORMULATIONS OF CURCUMINOIDS AND METHOD OF PREPARATION THEREOF

This application is a continuation of co-pending PCT Application No. PCT/IN2014/000031 filed Jan. 16, 2014, which claims priority from Indian Appl. Ser. No. 226/CHE/2013 filed Jan. 17, 2013, and a continuation-in-part of U.S. application Ser. No. 14/698,944 filed Apr. 29, 2015, which is a continuation of PCT Application Ser. No. PCT/IN2013/000673, filed Oct. 31, 2013, which claims priority from Indian Provisional application 4128/CHE/2012, filed Nov. 3, 2012, and a continuation-in-part of co-pending Ser. No. 14/206,044 filed Mar. 12, 2014, and is a continuation-in-part of co-pending U.S. application Ser. No. 14/476,555, filed Sep. 3, 2014, which is a divisional of co-pending U.S. application Ser. No. 13/645,031 filed Oct. 4, 2012, which is a continuation-in-part of PCT Application Serial No. PCT/IN2011/000232, filed Apr. 4, 2011, which claims priority of Indian Provisional Application Serial No. 950/CHE/2010, filed Apr. 5, 2010, and a continuation-in-part of co-pending U.S. application Ser. No. 14/520,292, filed Oct. 21, 2014, which is a divisional of Ser. No. 14/094,725, filed Dec. 2, 2013, which is a divisional of U.S. application Ser. No. 13/385,717, filed Mar. 5, 2012, which is a divisional of Ser. No. 12/926,985 filed Dec. 21, 2010, which is a divisional of Ser. No. 12/662,740 filed Apr. 30, 2010, which is a divisional of U.S. application Ser. No. 11/635,599 filed Dec. 8, 2006, which is a continuation of PCT Application Serial No. PCT/IN05/00176, filed May 30, 2005, and a continuation-in-part of co-pending U.S. application Ser. No. 14/623,608, filed Feb. 17, 2015, which is a divisional of Ser. No. 13/674,249, filed Nov. 12, 2012, which is a divisional of Ser. No. 13/506,572, filed Apr. 30, 2012, which is a divisional of Ser. No. 12/926,980, filed Dec. 21, 2010, which is a divisional of Ser. No. 12/073,864, filed Mar. 11, 2008, which is a continuation-in-part of Ser. No. 11/635,599, filed Dec. 8, 2006, which is a continuation of PCT Application Serial No. PCT/IN05/00176, filed May 30, 2005, and a continuation-in-part of co-pending U.S. application Ser. No. 14/206,044, filed Mar. 12, 2014, which is a continuation-in-part of U.S. application Ser. No. 13/645,031 filed Oct. 4, 2012, Ser. No. 13/674,249 filed Nov. 12, 2012, Ser. No. 14/094,725 filed Dec. 2, 2013, and claims the benefit of 61/794,175 filed Mar. 15, 2013, all of which applications are incorporated in entirety by reference.

BACKGROUND

Curcumin [1,7-bis(4-hydroxy-3-methoxyphenyl)-1,6-heptadiene-3,5-dione] is the major yellow pigment of turmeric, a commonly used spice, derived from the rhizome of the herb *Curcuma longa* Linn. In the Indian subcontinent and Southeast Asia, turmeric has traditionally been used as a treatment for inflammation, skin wounds, and tumors. In preclinical animal models, curcumin has shown cancer chemo preventive, antineoplastic and anti-inflammatory properties (Kelloff, G. I., et al, J. Cell Biochem., 1996, 265:54-71). Especially interesting is its ability to prevent the formation of carcinogen-induced intestinal premalignant lesions and malignancies in rats (Rao, C. V. et al, Cancer Res., 1995, 55:259-66; Kawamori, T. et al, Cancer Res., 1999, 59:597-601), and in the multiple neoplasia mouse (Mahmood, N. N. et al, Carcinogenesis, 2000, 31:921-27), a genetic model of the human disease familial adenomatous polyposis. Curcumin acts as a scavenger of oxygen species such as hydroxyl radical, superoxide anion and singlet oxygen (Subramanian, M. et al, Mutat. Res., 1994, 311:249-55; Tonnesen, H. H. et al, Int. J. Pharm., 1992, 87:79-87; Reddy, A. C. P. et al, Mol. Cell. Biochem., 1994, 137:1-8) and interferes with lipid peroxidation (Donatus, I. A., Biochem. Pharmacol., 1990, 39:1869-75; Sharma, S. C. et al, Biochem. Pharmacol., 1972, 21:1210-14).

Curcumin suppresses a number of key elements in cellular signal induction pathways pertinent to growth, differentiation and malignant transformations. Among signaling events inhibited by curcumin are protein kinases (Liu, J. V. et al, Carcinogenesis, 1993, 14:857-61), c-Jun/AP-1 activation (Huang, T. S. et al, Proc. Natl. Acad. Sci., 1991, 88:5292-96), prostaglandin biosynthesis (Huang, M-T. et al, In L. W. Battenberg (ed.) Cancer Chemo prevention, CRC Press, Boca Raton, 1992, pp 375-91) and activity and expression of the enzyme cyclooxygenase-2 (Huang, M. T., et al, Cancer Res., 1991, 51:813-19; Zhang, F. et al, Carcinogenesis, 1999, 20:445-51). This latter property is probably mediated by the ability of curcumin to block activation of the transcription factor NF-κB at the level of the NF-κB inducing kinase/IKKα/β signalling complex (Plummer, S. et al, Oncogene, 1999, 18:6013-20).

Despite this impressive array of beneficial bioactivities, the bioavailability of curcumin in animals and man remains low. In rodents, curcumin demonstrates poor systemic bioavailability (Ireson, C. R. et al, Cancer Res., 2001, 41:1058-64) which may be related to its inadequate absorption and fast metabolism. Curcumin bioavailability may also be poor in humans as seen from the results of a pilot study of a standardized turmeric extract in colorectal cancer patients (Sharma, R. A. et al, Clin. Cancer Res., 2001, 7:1834-1900).

Bioavailable curcumin formulation is a composition containing curcuminoid mixture and an added essential oil of turmeric, wherein the essential oil is present in an amount sufficient to cause an enhancement of bioavailability of the curcumin. The essential oil of turmeric contains turmerones principally α-turmerone and ar-turmerone. In earlier clinical trial Bioavailable curcumin formulation has shown higher bioavailability when compared with turmeric extract containing 95% total curcuminoids. Moreover, the curcumin was detected up to 8 hours in the blood of subjects administered with Bioavailable curcumin formulation as compared to only 4.5 hours in the subjects administered with turmeric extract containing 95% curcuminoids (Antony et al., Indian J Pharm Sci. 2008; 70:445-449). In a recent study by Yue et al., the effects of turmerones on curcumin transport were evaluated in human intestinal epithelial Caco-2 cells. The roles of turmerones on P-glycoprotein activities and mRNA expression were also evaluated. The authors concluded that the transport of curcumin in Caco-2 cell monolayers could be enhanced in the presence of turmerones. This study further validated our findings with Bioavailable curcumin formulation (Yue, G. L. et al, J Med Food, 2012, 15:242-252).

Controlled drug delivery systems deliver drug to the body so as to establish therapeutically effective blood levels of the active ingredient and once these blood levels are achieved they continue to maintain constant blood levels for long durations by delivering the drug to the body at the same rate as the body eliminates the drug. By avoiding peaks and troughs in blood levels associated with conventional dosage forms, controlled drug delivery systems lower the incidence of adverse effects or side effects. Very importantly controlled drug delivery systems reduce the frequency of dosing leading to convenience to the patient in terms of dosing and compliance to specified dosage regimens.

The convenience of administering a single dose of a medication which releases active ingredients over an extended period of time as opposed to the administration of a number of single doses at regular intervals has long been recognized in the pharmaceutical arts. The advantage to the patient and clinician in having consistent and blood levels of medication over an extended period of time are likewise recognized.

It is generally known that the rate at which an oral controlled drug delivery system delivers the drug into the blood is not the same as the rate at which it releases the drug into a test aqueous fluid because the gastrointestinal fluid's pH, composition and agitation intensity change with the specific location of the drug delivery system in the gastrointestinal tract i.e. from the stomach to the colon, fasted versus fed state, type and amount of food ingested, and also vary from individual to individual. In addition, the drug may not be absorbed in the same manner and propensity as we move from the stomach to the colon. Some drugs have an "absorption window" i.e. they are absorbed only from the upper parts of the gastrointestinal tract, whereas there are others whose absorption from the colon is not uniform or complete.

Ethylcellulose has become a polymer widely used in pharmaceutical film coating, especially when it is necessary to produce a modified-release dosage form. Ethylcellulose is a cellulose ether made by the reaction of ethyl chloride with alkali cellulose, as expressed by the reaction: RONa+ $C_2H_5Cl \rightarrow ROC_2H_5 + NaCl$, where R represents the cellulose radical. The structure that is most widely accepted for the cellulose molecule is a chain of β anhydroglucose units joined together by acetal linkages. These long, oxygen-linked anhydroglucose-unit chains have great strength, which is passed on to cellulose derivatives such as nitrocellulose, cellulose acetate, and ethylcellulose. The properties of flexibility and toughness in these derivatives are directly attributable to this long-chain structure.

Ethylcellulose is practically colorless, and retains this condition under a wide range of uses. Ethylcellulose is compatible with an unusually wide range of resins and plasticizers, including oils and waxes. It is soluble in a wide variety of solvents, thus making it easy to formulate this versatile material for any purpose where solvent application is desirable. Useful solvents among them are the esters, aromatic hydrocarbons, alcohols, ketones, and chlorinated solvents.

Shellac is a well-known commercial resin which originates as a secretion of an insect, *Laccifer lacca* or *Tachardia lacca*, found in Eastern countries, such as India, Pakistan and Sri Lanka. Principal components of shellac include aleuritic acid, shellolic acid and jalaric acid. Under some conditions, shellac can polymerize. However, shellac is not generally considered to be a polymer.

Shellac has been used as a coating on some foods and medications in order to improve their appearance. Examples of foods on which shellac has been applied include apples and confections. Forms of medications on which shellac has been employed as a coating include pills and tablets.

Although shellac coatings are enteric and non-toxic, shellac exhibits physical properties which make formation of such coatings problematic. For example, shellac is not water-soluble and has a melting point in the range of between about 75-80° C. Therefore, in order to minimize damage to surfaces to which it is applied, shellac typically must be dissolved in a medium before it is applied to a surface. The solvent can then be evaporated to leave a shellac coating.

Others have provided technologies for coating of tablets, pills, pellets etc using various polymers to protect the active drug in the stomach environment and to release the medicament in the intestine.

OBJECTS OF THE DISCLOSURE

An object of the disclosure is to provide a solid dosage form in the form of powder, granules, pellets, capsules, tablets or any other dosage form capable of delivering curcuminoids incorporated therein over an extended period of time.

Another object of the disclosure is to use ethyl cellulose, shellac, copolymer of ethyl acrylate and methyl methacrylate, acrylic acid copolymers, hydroxy propyl methyl cellulose (HPMC), hydroxy propyl cellulose or any other similar polymer either alone or as a mixture of them and curcuminoids blended with essential oil of turmeric having 45% Ar-turmerone to make the sustained release formulation.

Another object of the disclosure is to provide slow release of active principles (curcuminoids) from the delivery systems for extended period of time, thus allowing the gastrointestinal mucosa to absorb the drug for long duration so that significant blood level of the curcuminoids can be maintained for long duration of time.

Another object of the disclosure is to provide a sustained release curcuminoid formulation which enhances bioavailability of curcumin, demethoxycurcumin and bisdemethoxycurcumin in the blood for 36 hours and in tissues for more than 24 hours after a single dose of sustained release formulation.

Yet another object of the disclosure is to provide a sustained release curcuminoid formulation in which curcumin, demethoxycurcumin and bisdemethoxycurcumin are detected in the blood for about 24 to about 36 hours after a single dose of sustained release formulation.

Another object of the disclosure is to provide a sustained release curcuminoid formulation in which the half-life (t½) and area under the curve (AUC) of the curcumin, demethoxycurcumin and bisdemethoxycurcumin in the blood is increased after a single dose of sustained release formulation.

SUMMARY

The disclosure provides a sustained release drug delivery system for oral administration in the form of powder, granules, pellets, capsules, tablets or any other dosage form which provides sustained release of curcuminoids for extended period of time.

The disclosure also provides a composition of sustained drug delivery system which includes ethyl cellulose, shellac, copolymer of ethyl acrylate and methyl methacrylate, acrylic acid copolymers, hydroxy propyl methyl cellulose (HPMC), hydroxy propyl cellulose or any other similar polymer either alone or as a mixture of them.

The disclosure provides the ratio of active principles, i.e. Bioavailable curcumin formulation to release rate controlling polymer (for example, ethyl cellulose, shellac, copolymer of ethyl acrylate and methyl methacrylate, acrylic acid copolymers, hydroxy propyl methyl cellulose, hydroxy propyl cellulose or any other similar polymer either alone or in combination with each other) in the range of about 3:1 to about 50:1. The disclosure also provides the ratio of active principles, i.e. Bioavailable curcumin formulation or Regular turmeric extract (obtained from turmeric rhizomes by extraction with ethyl acetate) to polymer (for example, ethyl cellulose, shellac, copolymer of ethyl acrylate and methyl methacrylate, acrylic acid copolymers, hydroxy propyl methyl cellulose, hydroxy propyl cellulose or any other similar polymer either alone or in combination with each other) ranges from about 10:1 to 20:1.

The disclosure also provides a process for the making of sustained release drug delivery system which provides slow release of active constituents from the delivery system for a long time duration.

The disclosure provides a sustained release curcuminoid formulation which enhances bioavailability of curcumin, demethoxycurcumin and bisdemethoxycurcumin in the blood for 36 hours and in tissues for more than 24 hours after single dose of sustained release bioavailable curcumin formulation.

The disclosure provides a sustained release curcuminoid formulation in which curcumin, demethoxycurcumin and bisdemethoxycurcumin are detected in the blood for about 24 to about 36 hours after a single dose of sustained release bioavailable curcumin formulation.

The disclosure provide a sustained release curcuminoid formulation in which the half-life (t½) and area under the curve (AUC) of the curcumin, demethoxycurcumin and bisdemethoxycurcumin in the blood is increased after a single dose of sustained release bioavailable curcumin formulation.

BRIEF DESCRIPTION OF THE DRAWINGS

The above objectives and advantages of the disclosed teachings will become more apparent by describing in detail preferred embodiments thereof with reference to the attached drawings in which:

FIG. 26 provides Table 20(a) showing Mean blood concentration of curcumin, demethoxy curcumin and bisdemethoxy curcumin in healthy human subjects.

FIG. 27 provides Table 20(b) showing Mean blood concentration of curcumin, demethoxy curcumin and bisdemethoxy curcumin in healthy human subjects.

FIG. 28 provides Table 21(a) showing Mean blood concentration of curcumin, demethoxy curcumin and bisdemethoxy curcumin in healthy human subjects.

FIG. 29 provides Table 21(b) showing Mean blood concentration of curcumin, demethoxy curcumin and bisdemethoxy curcumin in healthy human subjects.

FIG. 30 provides Table 22 showing Cross over pattern of subjects treated with study drug.

FIG. 31 provides Table 23(a) showing Mean blood concentration, half life ($t_{1/2}$), and AUC of curcumin, demethoxy curcumin and bisdemethoxy curcumin in healthy human subjects.

FIG. 32 provides Table 23(b) showing Mean blood concentration, half life ($t_{1/2}$), and AUC of curcumin, demethoxy curcumin and bisdemethoxy curcumin in healthy human subjects.

FIG. 33 provides Table 24 showing Mean blood concentration, half life ($t_{1/2}$), and AUC of curcumin, demethoxy curcumin and bisdemethoxy curcumin in healthy human subjects.

DETAILED DESCRIPTION

Figure 1:
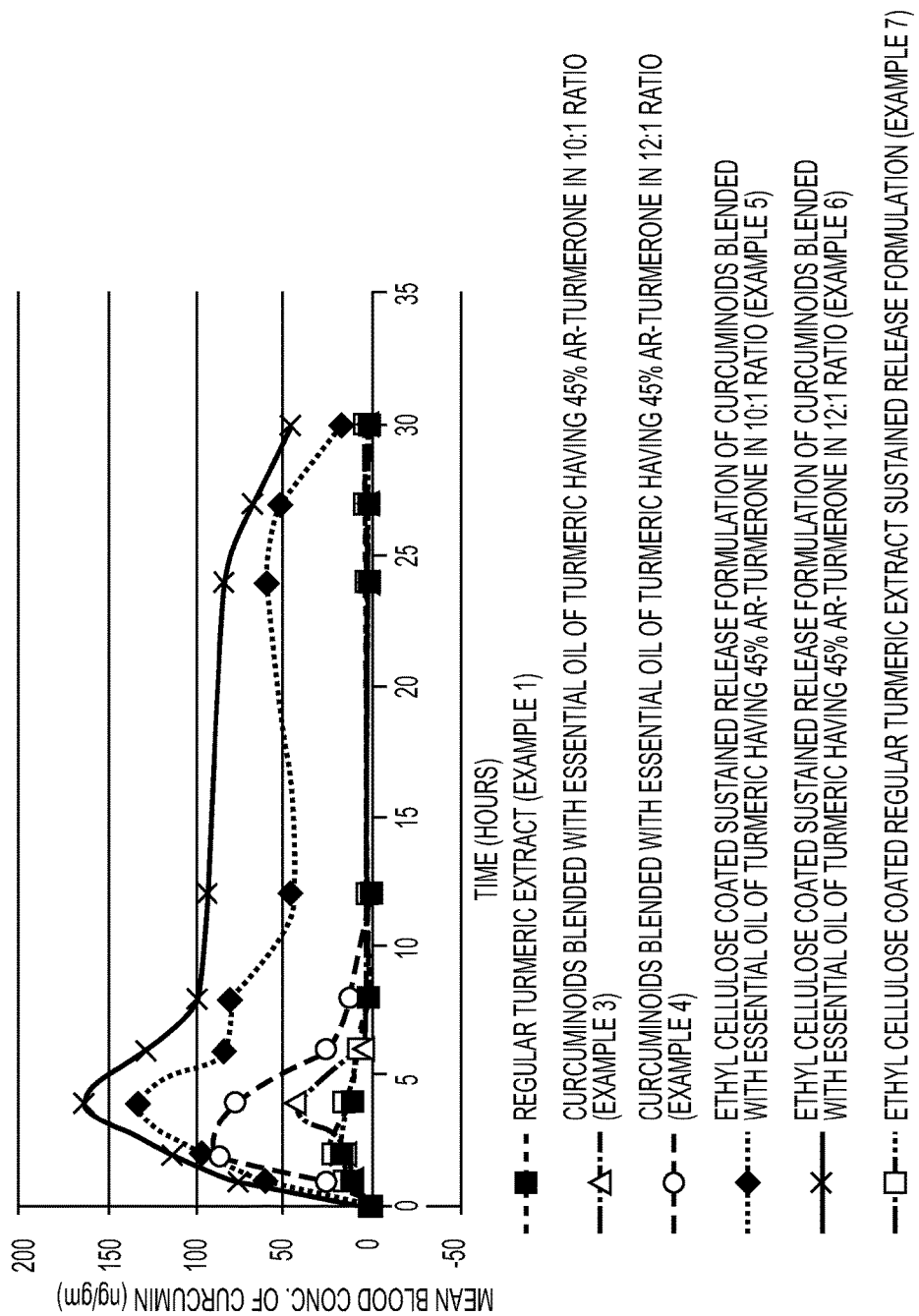
FIG. 1 provides a graph showing Mean blood concentration of curcumin (ng/gm) Vs Time in human subjects after administering sustained release curcuminoid formulation coated with ethyl cellulose in 10:1 ratio.
Figure 2:
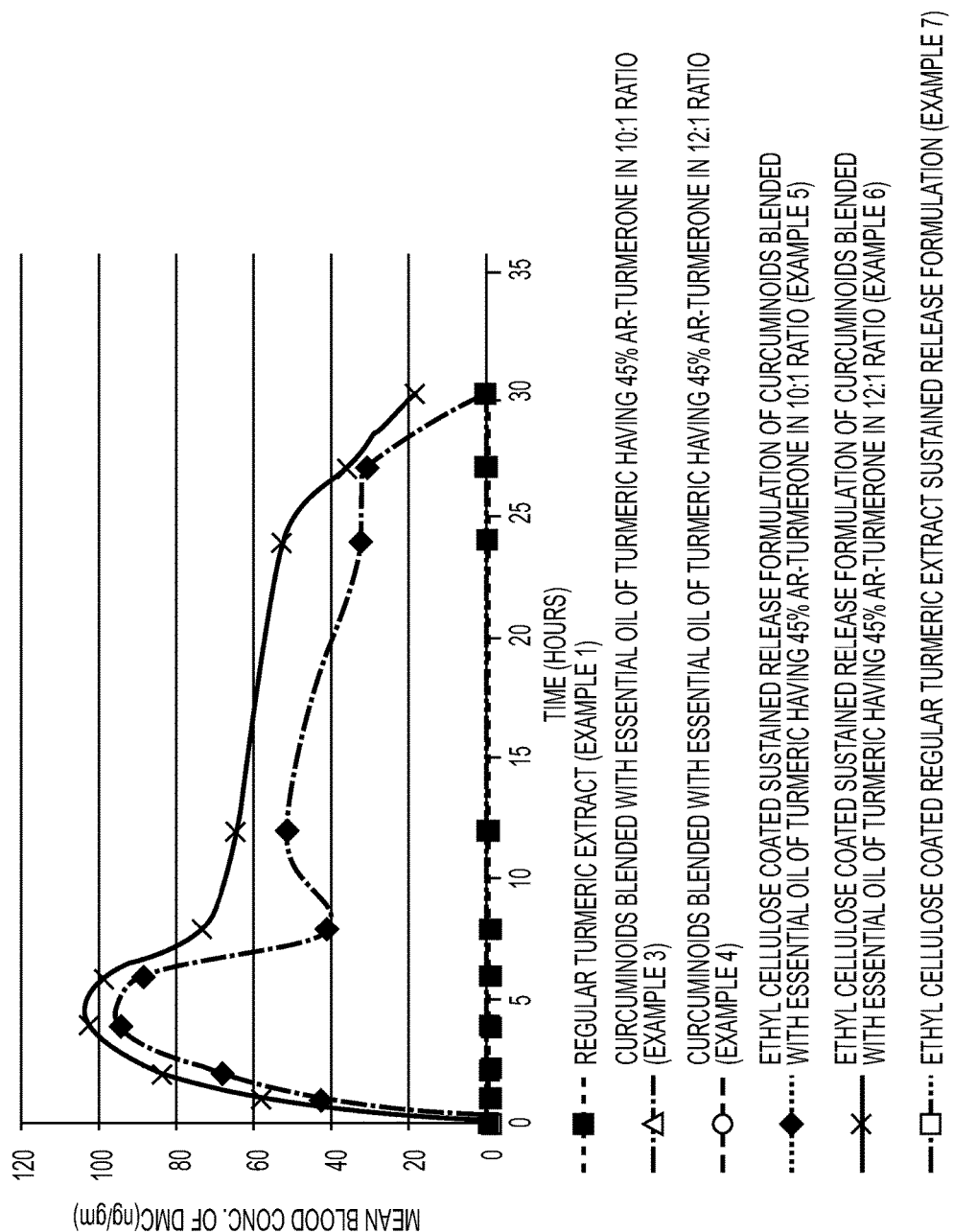
FIG. 2 provides a graph showing Mean blood concentration of demethoxy curcumin (DMC) (ng/gm) Vs Time in human subjects after administering sustained release curcuminoid formulation coated with ethyl cellulose in 10:1 ratio.
Figure 3:
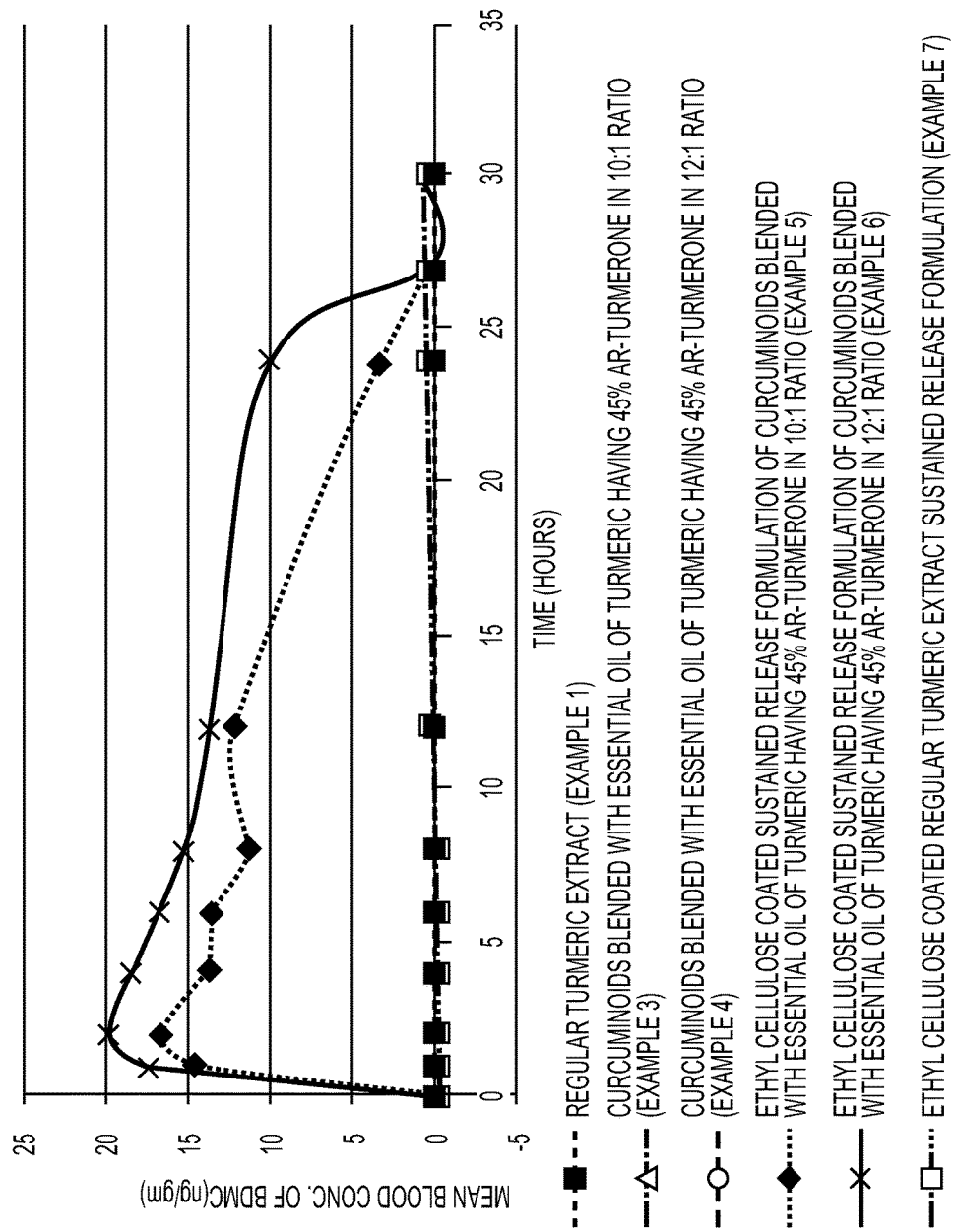
FIG. 3 provides a graph showing Mean blood concentration of bisdemethoxy curcumin (BDMC) (ng/gm) Vs Time in human subjects after administering sustained release curcuminoid formulation coated with ethyl cellulose in 10:1 ratio.
Figure 4:
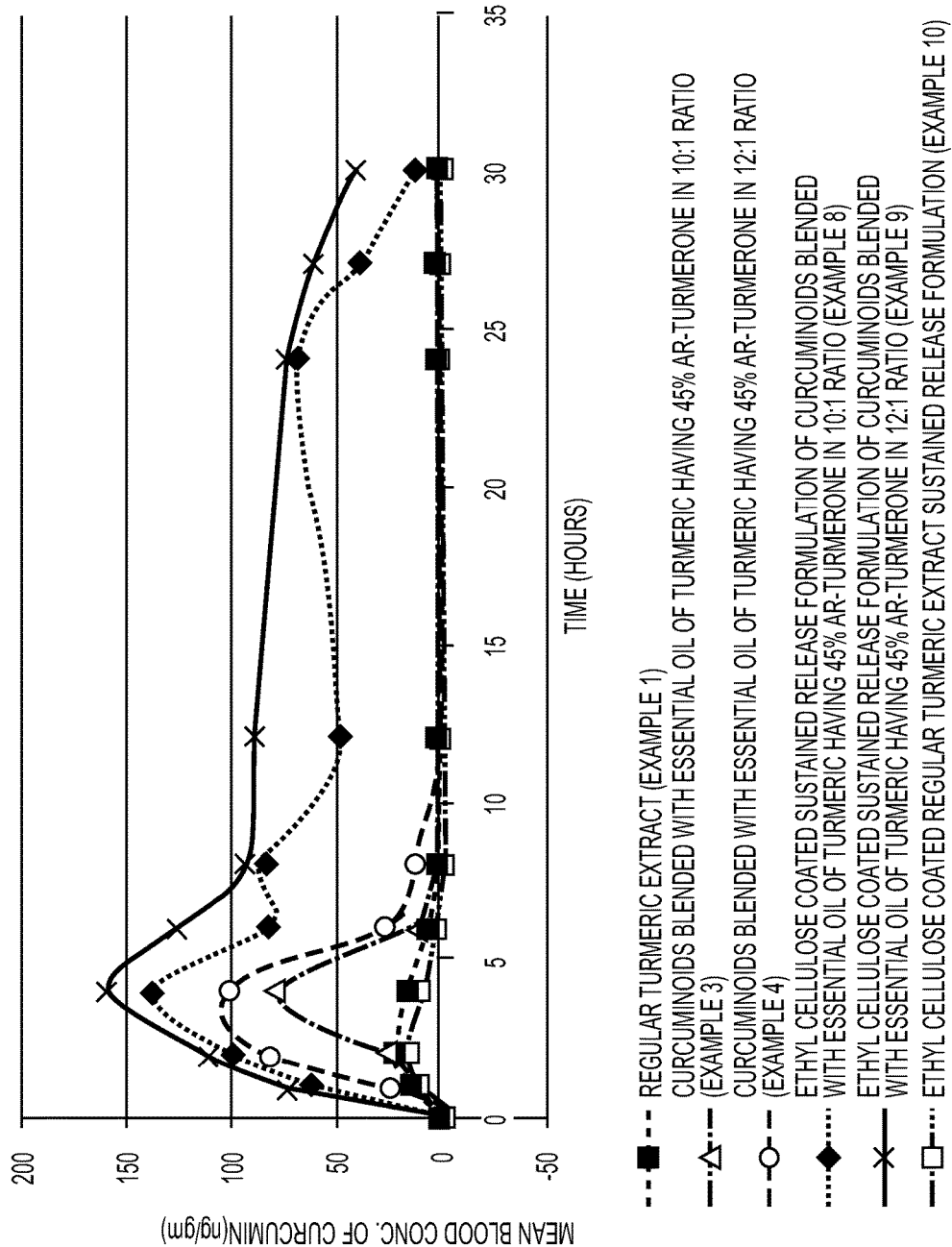
FIG. 4 provides a graph showing Mean blood concentration of curcumin (ng/gm) Vs Time in human subjects after administering sustained release curcuminoid formulation coated with ethyl cellulose in 500:25 ratio.
Figure 5:
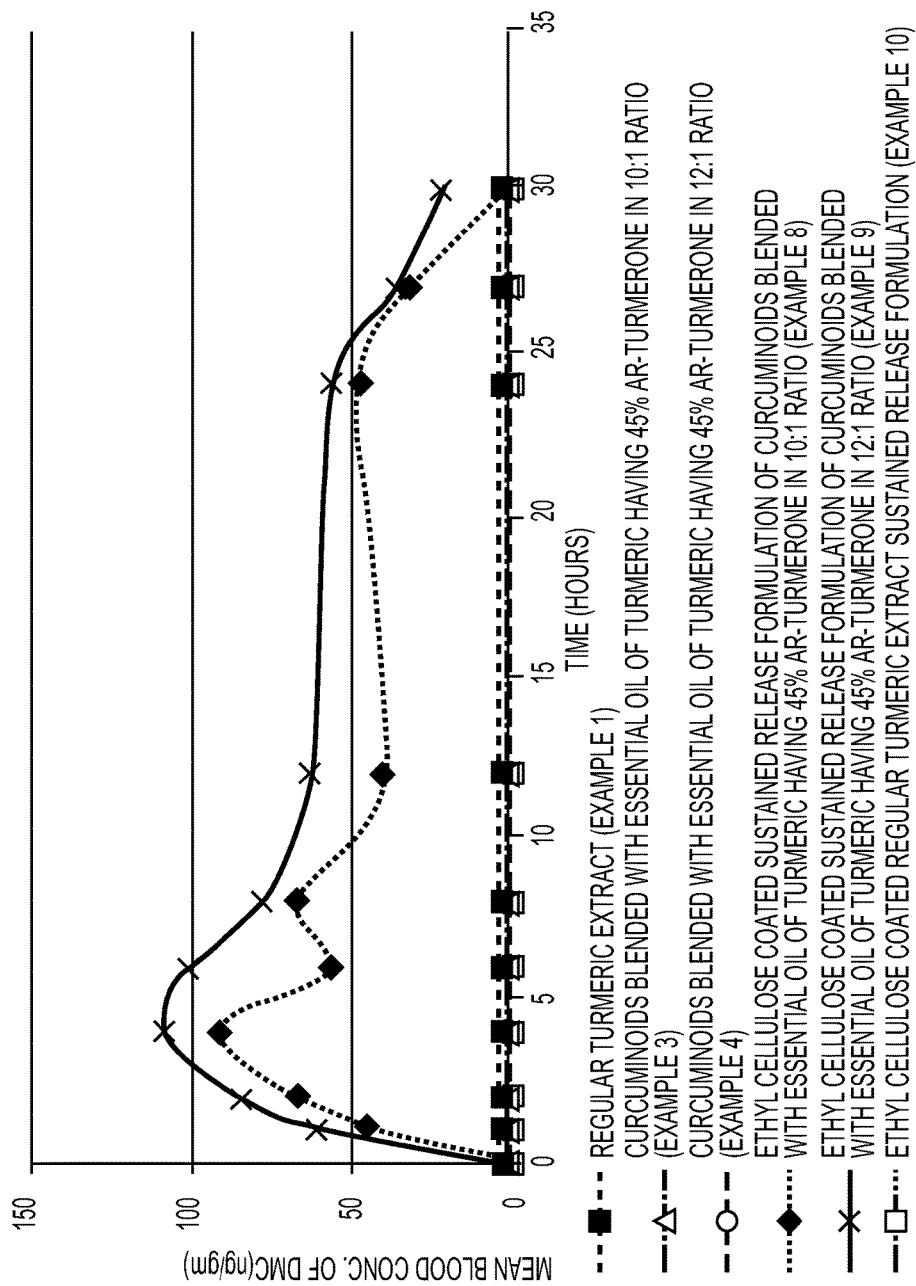
FIG. 5 provides a graph showing Mean blood concentration of demethoxy curcumin (DMC) (ng/gm) Vs Time in human subjects after administering sustained release curcuminoid formulation coated with ethyl cellulose in 500:25 ratio.
Figure 6:
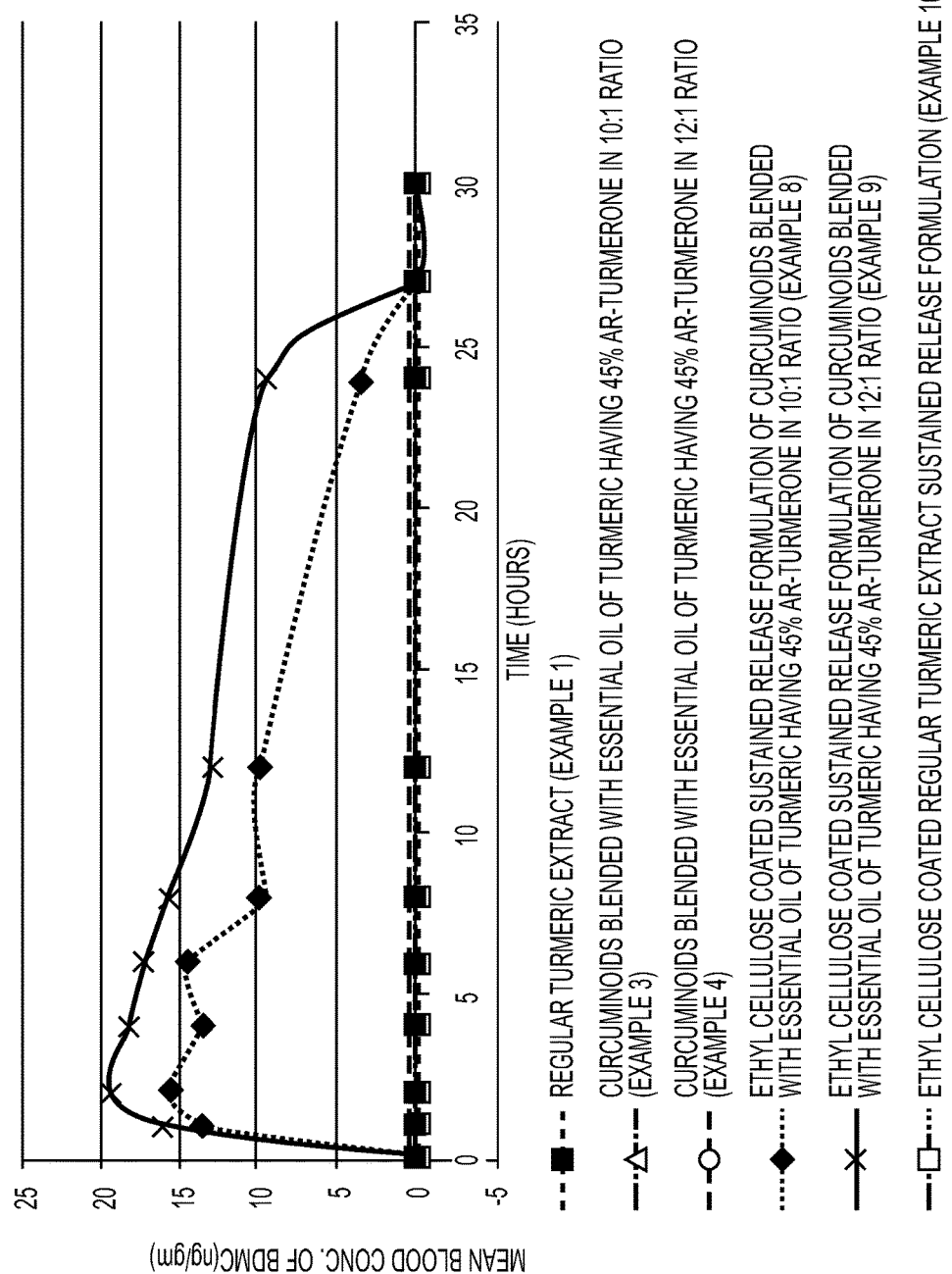
FIG. 6 provides a graph showing Mean blood concentration of bisdemethoxy curcumin (BDMC) (ng/gm) Vs Time in human subjects after administering sustained release curcuminoid formulation coated with ethyl cellulose in 500:25 ratio.
Figure 7:
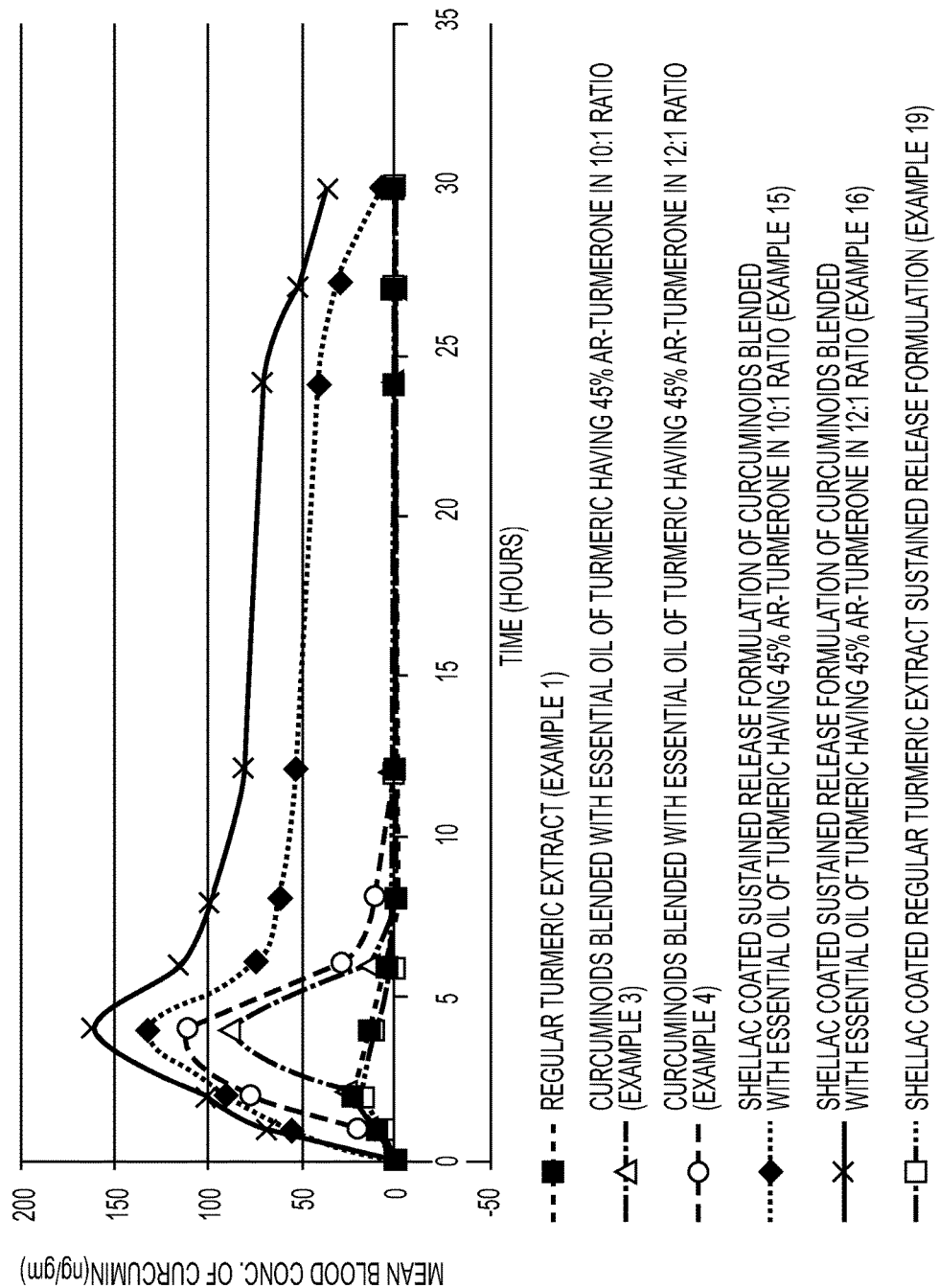
FIG. 7 provides a graph showing Mean blood concentration of curcumin (ng/gm) Vs Time in human subjects after administering sustained release curcuminoid formulation coated with shellac in 10:1 ratio.
Figure 8:
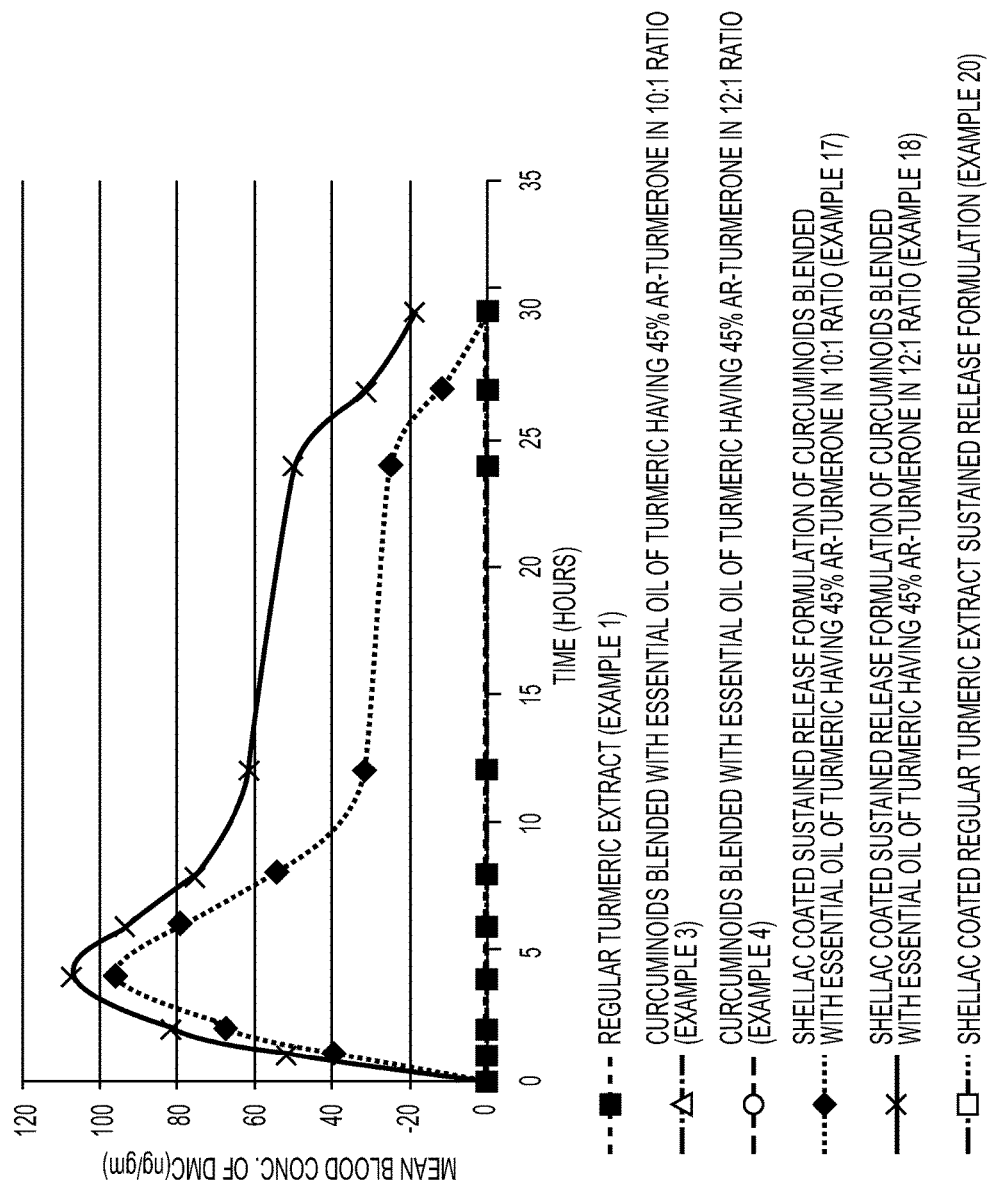
FIG. 8 provides a graph showing mean blood concentration in human subjects of demethoxy curcumin (DMC) (ng/gm) versus time after administering sustained release curcuminoid formulation coated with shellac in 10:1 ratio.
Figure 9:
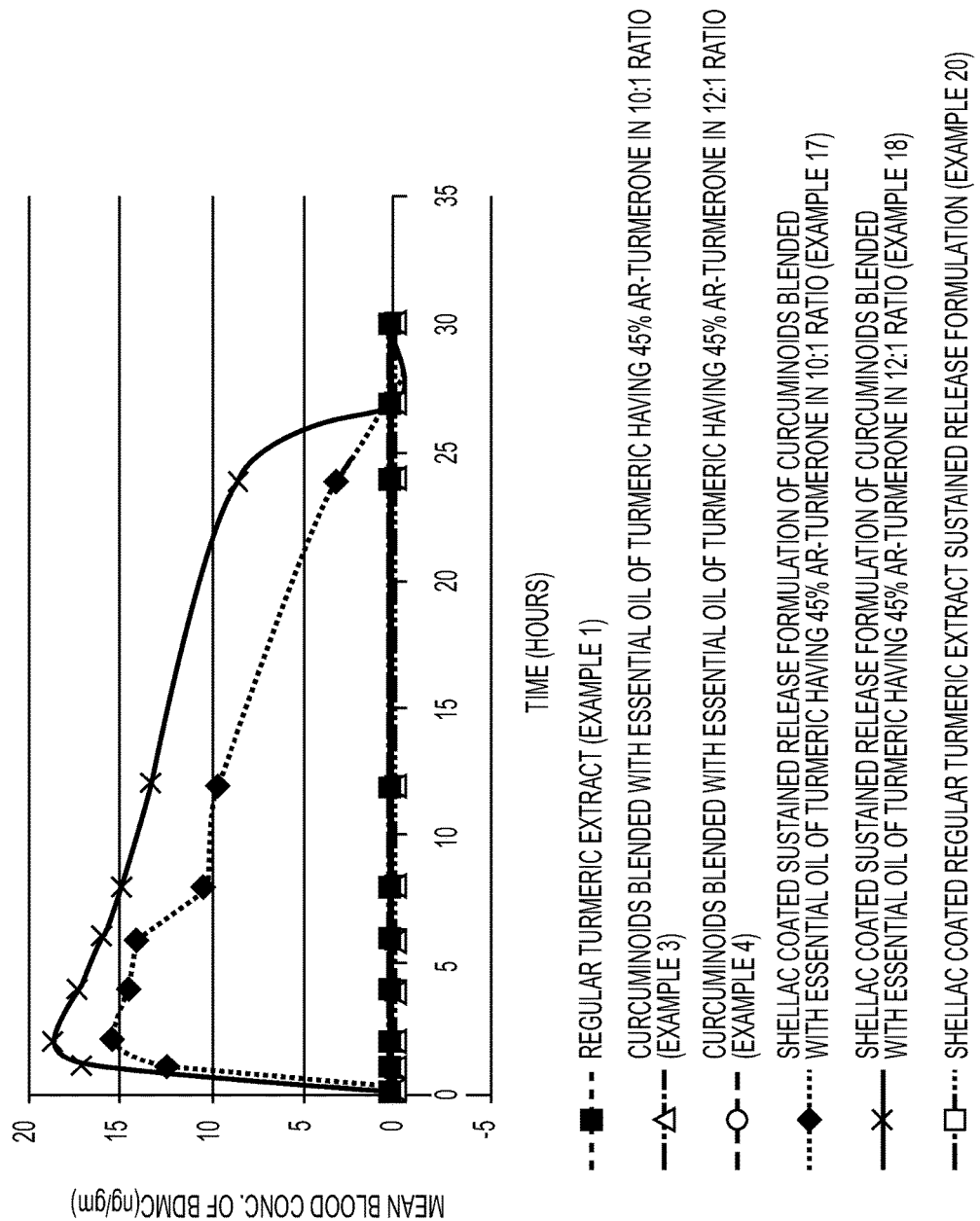
FIG. 9 provides a graph showing in human subjects the mean blood concentration of bisdemethoxy curcumin (BDMC) (ng/gm) versus time after administering sustained curcuminoid release formulation coated with shellac in 10:1 ratio of bioavailable curcumin composition to shellac.
Figure 10:
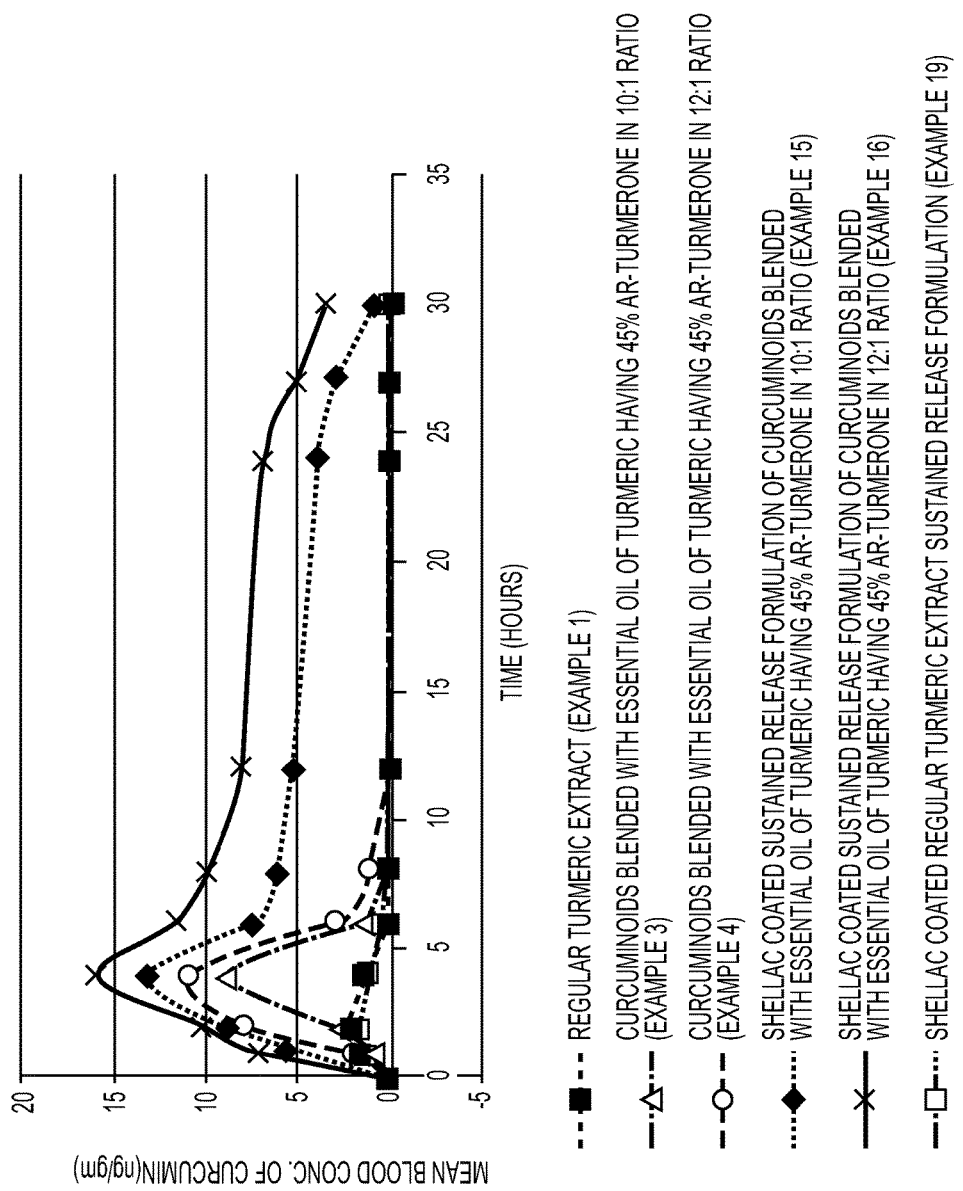
FIG. 10 provides a graph showing in human subjects the mean blood concentration of curcumin (ng/gm) Vs Time after administering sustained release curcuminoid formulation coated with shellac in 14:1 ratio.
Figure 11:
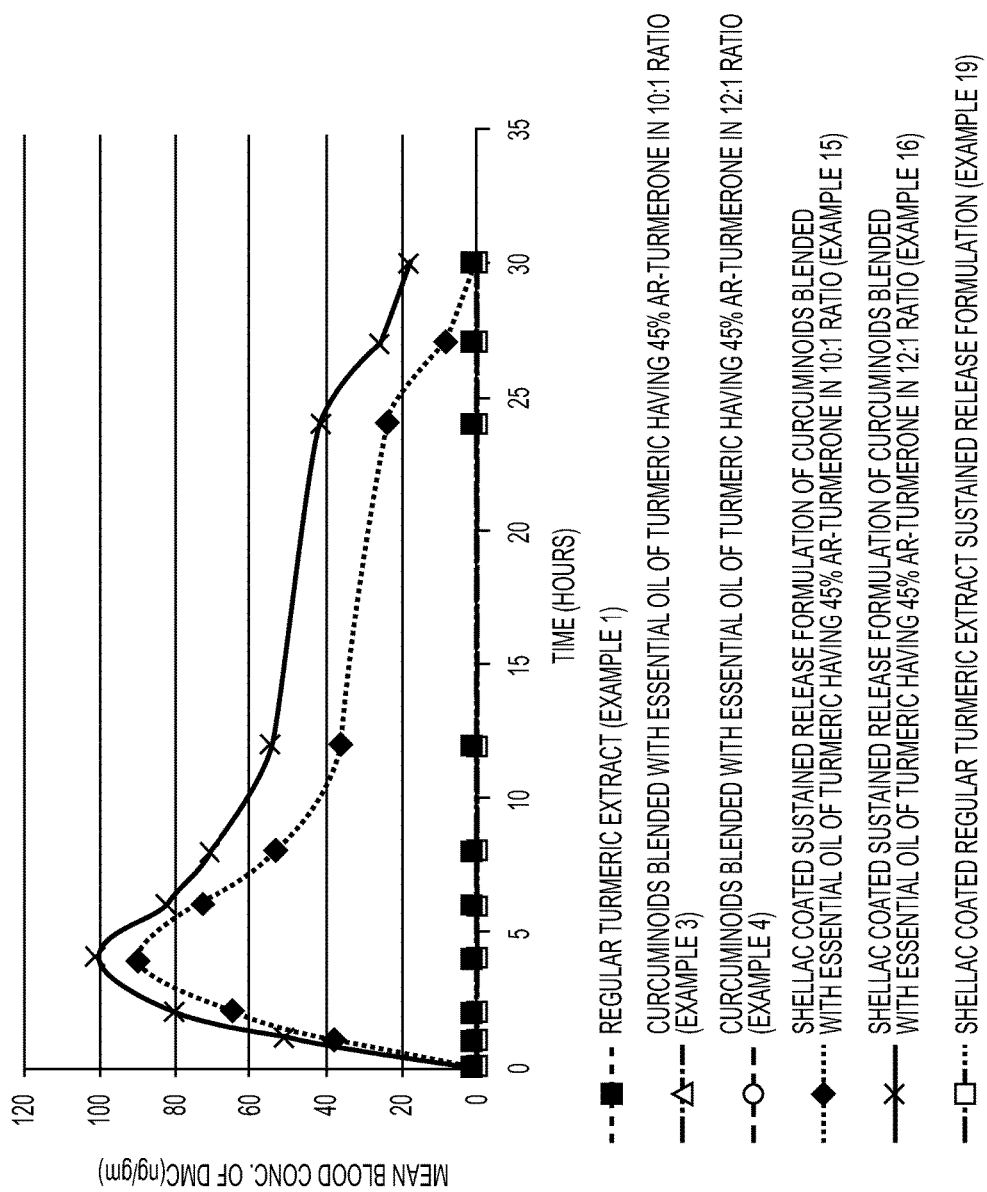
FIG. 11 provides a graph showing in human subjects, the mean blood concentration of demethoxy curcumin (DMC) (ng/gm) Vs Time after administering sustained release curcuminoid formulation coated with shellac in 14:1 ratio.
Figure 12:
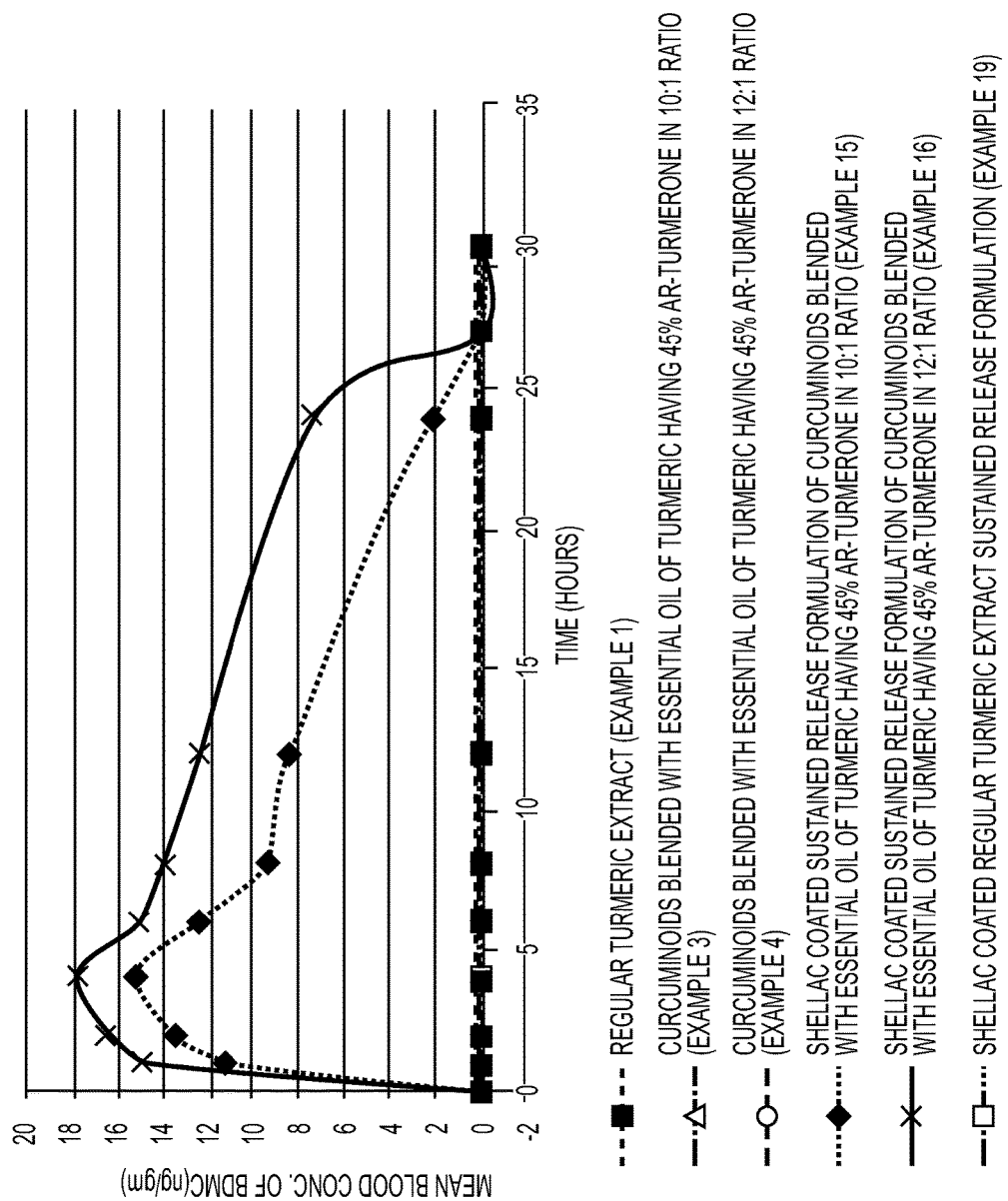
FIG. 12 provides a graph showing in human subjects the mean blood concentration of bisdemethoxy curcumin (BDMC) (ng/gm) Vs Time after administering sustained release curcuminoid formulation coated with shellac in 14:1 ratio.

The disclosure provides coating on a bioavailable curcumin formulation to obtain sustained release of curcumin, demethoxycurcumin and bisdemethoxycurcumin. A dosage form of the sustained release composition allowing absorption of curcuminoids for a long duration of time throughout the entire gastro-intestinal tract is provided.

The physiological condition in the gastro intestinal tract (GIT) varies from stomach to large intestine. The absorption of an ingested compound varies with the release of compound from the formulation at various parts of the GIT. If drugs can be delivered to the different absorptive sites in the GIT at different time points, the absorption as well as bioavailability of actives can be increased. The pH of GIT is different at different parts ranging from 1.2 to 2 in stomach to 6-7.2 in intestine. If the release of compounds in GIT can be modified to bring the compounds in direct contact with the absorptive site at substantially longer time points during the transit will lead to enhanced bioavailability. The bioavailable curcumin formulation was coated with different formulations of ethyl cellulose, shellac, copolymer of ethyl acrylate and methyl methacrylate, acrylic acid copolymers, hydroxy propyl methyl cellulose (HPMC), hydroxy propyl cellulose, and combinations thereof to modify the release of the active compounds in the GIT.

In sustained release curcuminoid composition, administering a single dosage of the composition enhances bioavailability of curcumin, demethoxycurcumin and bisdemethoxycurcumin in the body tissues even after 24 hours post drug. On the other hand, bioavailable curcumin formulation showed detection of low levels of curcumin only in the body tissues after 24 hours.

Bioavailable curcumin formulation is a blend of curcuminoids and essential oil of turmeric. Curcuminoid is a mixture of curcumin, demethoxycurcumin and bisdemethoxycurcumin. "Essential oil" or "essential oil of turmeric" is also referred to as "volatile oil" or "volatile oil of turmeric." Ar-turmerone is the main constituent of essential oil. Ar-turmerone constitutes about 40-50% of the essential oil of turmeric. In some embodiments, ar-turmerone constitutes about 45% of the essential oil of turmeric. In some embodiments, the weight ratio of the curcuminoid mixture to the essential oil of turmeric having 45% Ar-turmerone ranges from about 1:3 to about 99:1. In some embodiments, the weight ratio of curcuminoid mixture to the essential oil of turmeric having 45% Ar-turmerone is about 10:1. In some embodiments, the weight ratio of curcuminoid mixture to the essential oil of turmeric having 45% Ar-turmerone is about 12:1.

The disclosure also provides a process for the making of sustained release drug delivery system which provides slow release of active constituents from the delivery system for a long time duration, which includes dissolving the bioavailable curcumin formulation in ethyl acetate or any other suitable organic solvent in which the Bioavailable curcumin formulation is soluble to form a solution of bioavailable curcumin formulation (Solution A).

The polymers (for example, ethyl cellulose, shellac, copolymer of ethyl acrylate and methyl methacrylate, acrylic acid copolymers, hydroxy propyl methyl cellulose (HPMC), hydroxy propyl cellulose or any other similar polymer either in combination or alone) are dissolved in ethyl acetate or any other suitable organic solvent in which the polymers are soluble to form solution of polymer (Solution B). The organic solvent taken in this step should be miscible with the solvent taken in previous step to prepare solution of bioavailable curcumin formulation or solution of Regular turmeric extract (both are referred to as Solution 'A'). Solution of bioavailable curcumin formulation or a solution of Regular turmeric extract (Solution A) with solution of polymer (Solution B) are mixed. The mixture is stirred for about 30 min to 1 hr using a mechanical or magnetic stirrer. The solvent is evaporated under reduced pressure to obtain the sustained release product.

In one embodiment, the active principle selected to make sustained release delivery system for extended period of time is Bioavailable curcumin formulation.

In one embodiment, the excipients/polymers may be but not limited to ethyl cellulose, shellac, copolymer of ethyl acrylate and methyl methacrylate, acrylic acid copolymers, hydroxy propyl methyl cellulose (HPMC), hydroxy propyl cellulose or any other similar polymer either alone or in combination with each other.

In one embodiment, the solvents selected to dissolve active principles (bioavailable curcumin formulation or regular turmeric extract) or release rate controlling excipients or release rate controlling polymers may be ethyl acetate, alcohols, acetone, dichloromethane, dichloroethane, chloroform, diethyl ether or any other suitable solvent either alone or as a mixture of two or more solvents.

The disclosure provides a sustained release curcuminoid composition having a bioavailable curcumin composition and a release rate controlling excipient. The bioavailable composition of curcumin includes a curcuminoid mixture and an added essential oil of turmeric. The curcuminoid mixture includes curcumin, demethoxycurcumin and bisdemethoxycurcumin. The added essential oil of turmeric includes about 40% to about 50% of ar-turmerone. In some embodiments of the sustained release curcuminoid composition, the added essential oil of turmeric includes about 45% ar-turmerone.

In some embodiments of the sustained release curcuminoid composition, a weight ratio of the curcuminoid mixture to the added essential oil of turmeric ranges from about 1:3 to about 99:1. In some embodiments of the sustained release curcuminoid composition, the weight ratio of the curcuminoid mixture to the essential oil of turmeric is about 10:1. In some embodiments of the sustained release curcuminoid composition, the weight ratio of the curcuminoid mixture to the essential oil of turmeric is about 12:1.

In some embodiments of the sustained release curcuminoid composition, the release rate controlling excipient is ethyl cellulose, shellac, copolymer of ethyl acrylate and methyl methacrylate, acrylic acid copolymers, hydroxy propyl methyl cellulose (HPMC), hydroxy propyl cellulose or combinations thereof.

In some embodiments of the sustained release curcuminoid composition, a weight ratio of the bioavailable curcumin composition to the release rate controlling excipient ranges from about 3:1 to about 50:1. In some embodiments of the sustained release curcuminoid composition, a weight ratio of the bioavailable curcumin composition to the release rate controlling excipient ranges from about 10:1 to about 20:1. In some embodiments of the sustained release curcuminoid composition, a weight ratio of the bioavailable curcumin composition to the release rate controlling excipient is about 10:1. In some embodiments of the sustained release curcuminoid composition, a weight ratio of the bioavailable curcumin composition to the release rate controlling excipient is about 14:1. In some embodiments of the sustained release curcuminoid composition, a weight ratio of the bioavailable curcumin composition to the release rate controlling excipient is about 20:1.

In some embodiments of the sustained release curcuminoid composition, the release rate controlling excipient is shellac. In some embodiments of the sustained release curcuminoid composition, shellac forms a coating on the bioavailable curcumin composition. In some embodiments of the sustained release curcuminoid composition, a weight ratio of the bioavailable curcumin composition to the shellac ranges from about 3:1 to about 50:1. In some embodiments of the sustained release curcuminoid composition, a weight ratio of the bioavailable curcumin composition to the shellac ranges from about 10:1 to about 14:1. In some embodiments of the sustained release curcuminoid composition, a weight ratio of the bioavailable curcumin composition to the shellac is about 10:1. In some embodiments of the sustained release curcuminoid composition, a weight ratio of the bioavailable curcumin composition to the shellac is about 14:1.

In some embodiments of the sustained release curcuminoid composition, the release rate controlling excipient is ethyl cellulose. In some embodiments of the sustained release curcuminoid composition, ethyl cellulose forms a coating on the bioavailable curcumin composition. In some embodiments of the sustained release curcuminoid composition, a weight ratio of the bioavailable curcumin composition to the ethyl cellulose ranges from about 3:1 to about 50:1. In some embodiments of the sustained release curcuminoid composition, a weight ratio of the bioavailable curcumin composition to the ethyl cellulose ranges from about 10:1 to about 20:1. In some embodiments of the sustained release curcuminoid composition, a weight ratio of the bioavailable curcumin composition to the ethyl cellulose is about 10:1. In some embodiments of the sustained release curcuminoid composition, a weight ratio of the bioavailable curcumin composition to the ethyl cellulose is about 20:1.

In some embodiments of the sustained release curcuminoid composition, a weight ratio of the bioavailable curcumin composition to the copolymer of ethyl acrylate and methyl methacrylate ranges from about 3:1 to about 50:1. In some embodiments of the sustained release curcuminoid composition, the weight ratio of the bioavailable curcumin composition to the copolymer of ethyl acrylate and methyl methacrylate ranges from about 10:1 to about 20:1.

In some embodiments, the sustained release curcuminoid composition is orally administration. In some embodiments, a dosage form of the sustained release curcuminoid composition for oral administration is provided. In some embodiments, the dosage form of the sustained release curcuminoid composition can be a powder, pellets, granules, tablets or capsules.

In some embodiments of the sustained release curcuminoid composition, curcumin, demethoxycurcumin and bisdemethoxycurcumin are detected in the blood for about 24 to about 36 hours. In some embodiments of the sustained release curcuminoid composition, a single dosage of the composition provides curcumin, demethoxycurcumin and bisdemethoxycurcumin in the body for 24 hours. In some embodiment of the sustained release curcuminoid composition, a single dosage of the composition provides curcumin, demethoxycurcumin and bisdemethoxycurcumin in the body for 36 hours. The disclosure provides a sustained release curcuminoid composition, wherein administering a single dosage of the sustained release curcuminoid composition enhances bioavailability of curcumin, demethoxycurcumin and bisdemethoxycurcumin in the blood for 24 hours, whereas a single dosage administration of the bioavailable curcumin composition alone did not provide bioavailability of curcumin, demethoxycurcumin and bis demethoxy curcumin in the blood for 24 hours. In some embodiments, administering a single dosage of the sustained release curcuminoid composition provided bioavailable curcumin, demethoxycurcumin and bisdemethoxycurcumin in the blood for 36 hours when compared to a single dosage administration of the bioavailable curcumin composition alone (without the rate controlling excipients).

In some embodiments of the sustained release curcuminoid composition, administering a single dosage of the sustained release curcuminoid composition enhances bioavailability of curcumin, demethoxycurcumin and bisdemethoxycurcumin in a body tissue for more than 24 hours when compared to administration of the bioavailable curcumin composition alone. In some embodiments of the sustained release curcuminoid composition, the half-life ($t_{1/2}$) of the curcumin, demethoxycurcumin and bisdemethoxycurcumin in the blood is increased when compared to the half life ($t_{1/2}$) of curcumin, demethoxycurcumin and bisdemethoxycurcumin in the blood following a single dose administration of the bioavailable curcumin composition alone. Following a single dose administration of sustained release curcuminoid formulation prepared as per Example 21 and 22, the half life (t½) of curcumin is 11.8 and 11.4 hours respectively. Whereas administering single dose of bioavailable curcumin formulation prepared as per example 3 and 4, the half life of curcumin is 4.5 and 4.7 respectively. Administering a single dose administration of sustained release curcuminoid formulation prepared as per Example 21 resulted in a half life (t½) of demethoxycurcumin and bisdemethoxycurcumin is 10.4 and 10.2 hours respectively. But after administering bioavailable curcumin formulation demethoxycurcumin and bisdemethoxycurcumin is not detected in blood. Administering the sustained release curcuminoid formulation prepared as per Example 22, the half life (t½) of demethoxycurcumin and bisdemethoxycurcumin is about 9.9 and about 9.2 hours respectively. Administering regular turmeric extract resulted in a half life (t½) of curcumin of about 1.07 hours. Demethoxycurcumin and bisdemethoxycurcumin is not detected in blood after administration of the regular turmeric extract.

Half life means the period of time required for the concentration or amount of drug in the body to be reduced to exactly one-half of a given concentration or amount. A drug's blood half life depends on how quickly the drug is eliminated from the blood. Higher $t_{1/2}$ indicates the longer stay of the drug in the body.

In another embodiment, the area under the curve ($AUC_{0-t}$) of the curcumin, demethoxy curcumin and bisdemethoxy curcumin in the blood is increased after a single dosage of sustained release curcuminoid formulation. After a single dosage of sustained release curcuminoid formulation prepared as per Example 21 and 22, the AUC (ng/gm) of curcumin in blood is about 4002.5 and about 3752.8 respectively. Whereas after a single dosage of bioavailable curcumin formulation prepared as per example 3 and 4, the AUC of curcumin in blood is about 321.9 and about 414.9 ng/gm respectively. After a single dosage of sustained release curcuminoid formulation prepared as per Example 21, the AUC of demethoxycurcumin and bisdemethoxycurcumin in blood is about 3226.1 and about 1056.8 ng/gm respectively. But after administering a single dose of bioavailable curcumin formulation demethoxycurcumin and bisdemethoxycurcumin is not detected in blood. In sustained release curcuminoid formulation prepared as per Example 22, the AUC of demethoxycurcumin and bisdemethoxycurcumin is about 2939.7 and about 957.1 ng/gm respectively. Administering regular turmeric extract resulted in an AUC (ng/gm) of curcumin of about 23.9. Demethoxycurcumin and bisdemethoxycurcumin is not detected in blood after administration of the regular turmeric extract.

The area under the blood drug concentration-time curve (AUC) reflects the actual body exposure to drug after administration of a dose of the drug. This area under the curve is dependent on the rate of elimination of the drug from the body and the dose administered. AUC gives a measure of how much and how long a drug stays in a body. The total amount of drug eliminated by the body may be assessed by adding up or integrating the amounts eliminated in each time interval, from time zero (time of the administration of the drug) to a definite time (AUC(0-t)) or infinite time (AUC (0-∞)). This total amount corresponds to the fraction of the dose administered that reaches the systemic circulation. Bioavailability is usually assessed by determining the area under the blood concentration-time curve. Bioavailability is proportional to the total area under the blood concentration-time curve (AUC).

In some embodiments of the sustained release curcuminoid composition, the area under the curve (AUC) of the curcumin, demethoxycurcumin and bisdemethoxycurcumin in the blood is increased when compared to the AUC of curcumin, demethoxycurcumin and bisdemethoxycurcumin upon administration of the bioavailable curcumin composition alone (without the rate controlling excipients).

In some embodiments, the disclosure provides a method of preparing a sustained release curcuminoid composition. The method includes suspending a curcuminoid mixture in water to form a suspension. Then adding essential oil of turmeric to the suspension to form a second mixture. Then homogenizing the second mixture to obtain a slurry. Then drying the slurry under heat and vacuum to obtain a uniform blend of the bioavailable curcumin composition. Next dissolving the bioavailable curcumin composition in ethyl acetate to obtain a solution of the bioavailable curcumin composition. Mixing the solution of the bioavailable curcumin composition with an ethyl cellulose solution to obtain a mixture. The ethyl cellulose solution is made by dissolving the ethyl cellulose in ethanol. Evaporating the mixture of the bioavailable curcumin composition and ethyl cellulose at 50° C. under reduced pressure to obtain the sustained release curcuminoid composition.

In some embodiments, the disclosure provides a method of preparing a sustained release curcuminoid composition. The method includes suspending a curcuminoid mixture in water to form a suspension. Then adding essential oil of turmeric to the suspension to form a second mixture. Then homogenizing the second mixture to obtain a slurry. Then drying the slurry under heat and vacuum to obtain a uniform blend of the bioavailable curcumin composition. Next dissolving the bioavailable curcumin composition in ethyl acetate to obtain a solution of the bioavailable curcumin composition. Mixing the solution of the bioavailable curcumin composition with a solution having a copolymer of ethyl acrylate and methyl methacrylate to obtain a mixture. The solution having a copolymer of ethyl acrylate and methyl methacrylate is made by dissolving the copolymer of ethyl acrylate and methyl methacrylate in 1:1 ratio of methanol:ethyl acetate. Evaporating the mixture of the bioavailable curcumin composition and the copolymer of ethyl acrylate and methyl methacrylate at 50° C. under reduced pressure to obtain the sustained release curcuminoid composition.

In some embodiments, the disclosure provides a method of preparing a sustained release curcuminoid composition. The method includes suspending a curcuminoid mixture in water to form a suspension. Then adding essential oil of turmeric to the suspension to form a second mixture. Then homogenizing the second mixture to obtain a slurry. Then drying the slurry under heat and vacuum to obtain a uniform blend of the bioavailable curcumin composition. Next dissolving the bioavailable curcumin composition in ethyl acetate to obtain a solution of the bioavailable curcumin composition. Mixing the solution of the bioavailable curcumin composition with a solution having a shellac, a copolymer of ethyl acrylate and methyl methacrylate, an ethyl cellulose and a hydroxyl propyl methyl cellulose to obtain a mixture. The solution having a shellac, a copolymer of ethyl acrylate and methyl methacrylate, an ethyl cellulose and a hydroxyl propyl methyl cellulose is made by dissolving shellac, copolymer of ethyl acrylate and methyl methacrylate, ethyl cellulose and hydroxyl propyl methyl cellulose in 1:1 ratio of methanol:ethyl acetate. Evaporating the mixture of the bioavailable curcumin composition and the release rate controlling excipients including shellac, copolymer of ethyl acrylate and methyl methacrylate, ethyl cellulose and hydroxyl propyl methyl cellulose at 50° C. under reduced pressure to obtain the sustained release curcuminoid composition.

In some embodiments, the disclosure provides a method of preparing a sustained release curcuminoid composition. The method includes suspending a curcuminoid mixture in water to form a suspension. Then essential oil of turmeric is added to the suspension to form a second mixture. Then the second mixture is homogenized to obtain a slurry. Then the slurry is dried under heat and vacuum to obtain a uniform blend of the bioavailable curcumin composition. Next the bioavailable curcumin composition is dissolved in ethyl acetate to obtain a solution of the bioavailable curcumin composition. Then the solution of the bioavailable curcumin composition is mixed with shellac solution to obtain a mixture. The shellac solution is prepared by dissolving shellac in ethanol. The mixture of the bioavailable curcumin composition and shellac is evaporated at 50° C. under reduced pressure to obtain the sustained release curcuminoid composition.

Some embodiments are related to a method of treatment by administering the sustained release composition to a subject.

In some embodiments, the disclosure provides a sustained release curcuminoid composition having first component and a second component. The first component includes a bioavailable curcumin composition. The bioavailable curcumin composition includes a curcuminoid mixture and an added essential oil of turmeric. The curcuminoid mixture includes curcumin, demethoxycurcumin and bisdemethoxycurcumin. In some embodiments, the ar-turmerone constitutes about 40% to about 50% of the added essential oil of turmeric. In some embodiments, the added essential oil of turmeric includes about 45% ar-turmerone. In some embodiments, the first component has a weight ratio of the curcuminoid mixture to the added essential oil of turmeric ranging from about 1:3 to about 99:1. In some embodiments, the first component has a weight ratio of the curcuminoid mixture to the added essential oil of turmeric of about 10:1. In some embodiments, the first component includes a weight ratio of the curcuminoid mixture to the added essential oil of turmeric of about 12:1. The second component includes the bioavailable curcumin composition and a release rate controlling excipient. The release rate controlling excipient can be ethyl cellulose, shellac, copolymer of ethyl acrylate and methyl methacrylate, acrylic acid copolymers, hydroxy propyl methyl cellulose (HPMC), hydroxy propyl cellulose, or combinations thereof. In some embodiments, the second component includes a weight ratio of the bioavailable curcumin composition to the release rate controlling excipient ranging from about 3:1 to about 50:1. In some embodiments, the second component includes a weight ratio of the bioavailable curcumin composition to the release rate controlling excipient ranging from about 10:1 to about 20:1. In some embodiments of the sustained release curcuminoid composition, the first component ranges from about 5% to about 30%; and, the second component ranges from about 30 to about 80%, and the weight ratio of the bioavailable curcumin composition to the release rate controlling excipient is about 10:1.

In some embodiments, the disclosure provides a sustained release curcuminoid composition having first component, a second component and a third component. The first component includes a bioavailable curcumin composition. The bioavailable curcumin composition includes a curcuminoid mixture and an added essential oil of turmeric. The curcuminoid mixture includes curcumin, demethoxycurcumin and bisdemethoxycurcumin. In some embodiments, the ar-turmerone constitutes about 40% to about 50% of the added essential oil of turmeric. In some embodiments, the added essential oil of turmeric includes about 45% ar-turmerone. In some embodiments, the first component has a weight ratio of the curcuminoid mixture to the added essential oil of turmeric ranging from about 1:3 to about 99:1. In some embodiments, the first component has a weight ratio of the curcuminoid mixture to the added essential oil of turmeric of about 10:1. In some embodiments, the first component includes a weight ratio of the curcuminoid mixture to the added essential oil of turmeric of about 12:1. The second component includes the bioavailable curcumin composition and a release rate controlling excipient. The release rate controlling excipient can be ethyl cellulose, shellac, copolymer of ethyl acrylate and methyl methacrylate, acrylic acid copolymers, hydroxy propyl methyl cellulose (HPMC), hydroxy propyl cellulose, or combinations thereof. In some embodiments, the second component includes a weight ratio of the bioavailable curcumin composition to the release rate controlling excipient ranging from about 3:1 to about 50:1. In some embodiments, the second component includes a weight ratio of the bioavailable curcumin composition to the release rate controlling excipient ranging from about 10:1 to about 20:1. In some embodiments of the sustained release curcuminoid composition, the first component ranges from about 5% to about 30%; and, the second component ranges from about 30 to about 80%, and the weight ratio of the bioavailable curcumin composition to the release rate controlling excipient is about 10:1. The third component includes the bioavailable curcumin composition and the release rate controlling excipient. In some embodiments, the third component includes a weight ratio of the bioavailable curcumin to the release rate controlling excipient ranges from about 3:1 to about 50:1.

In some embodiments, the disclosure provides a sustained release curcuminoid composition having about 5% to about 30% of the first component; about 30 to about 80% of the second component, and about 15% to about 40% of a third component. The second component includes the bioavailable curcumin composition and shellac, and the weight ratio of the bioavailable curcumin composition to the shellac is about 10:1. The third component includes the bioavailable curcumin composition and shellac, and the weight ratio of the bioavailable curcumin composition to the shellac is about 14:1.

Some embodiments of the sustained release curcuminoid composition include about 10% of the first component, about 60% of the second component, and about 30% of the third component. The second component includes the bioavailable curcumin composition and shellac. In the second component, the weight ratio of shellac to the bioavailable curcumin composition is about 10:1. The third component includes the bioavailable curcumin composition and shellac.

In the third component, the weight ratio of the bioavailable curcumin composition to the shellac is about 14:1.

Some embodiments of the sustained release curcuminoid composition include about 5% to about 30% of the first component, about 30 to about 80% of the second component, and, about 15% to about 40% of a third component. The second component includes the bioavailable curcumin composition and the ethyl cellulose, and the weight ratio of the bioavailable curcumin composition to the ethyl cellulose is about 10:1. The third component includes the bioavailable curcumin composition and the ethyl cellulose, and the weight ratio of the bioavailable curcumin composition to the ethyl cellulose is about 20:1.

Some embodiments of the sustained release curcuminoid composition includes about 10% of the first component, about 60% of the second component, and, about 30% of a third component. The second component includes the bioavailable curcumin composition and the ethyl cellulose, and the weight ratio of the bioavailable curcumin composition to the ethyl cellulose is about 10:1. The third component includes the bioavailable curcumin composition and ethyl cellulose. The weight ratio of the bioavailable curcumin composition to the ethyl cellulose in the third component is about 20:1.

Some embodiments provide a sustained release curcuminoid composition having a first component, a second component and a third component. The first component includes a bioavailable curcumin composition. The second component includes a first weight ratio of the bioavailable curcumin composition to a release rate controlling excipient. The third component includes a second weight ratio of the bioavailable curcumin composition to the release rate controlling excipient. The bioavailable curcumin composition is a blend of a curcuminoid mixture and an added essential oil of turmeric. The curcuminoid mixture includes curcumin, demethoxycurcumin and bisdemethoxycurcumin. The added essential oil of turmeric includes about 40% to about 50% of ar-turmerone. In some embodiments, the first weight ratio in the second component ranges from about 3:1 to about 50:1. In some embodiments of the sustained release composition, the first weight ratio in the second component ranges from about 10:1 to about 20:1. In some embodiments, the third component includes a second weight ratio of the bioavailable curcumin composition to the release rate limiting excipient ranging from about 3:1 to about 50:1. The release rate controlling excipient is ethyl cellulose, shellac, copolymer of ethyl acrylate and methyl methacrylate, acrylic acid copolymers, hydroxy propyl methyl cellulose (HPMC), hydroxy propyl cellulose, or combinations thereof. In some embodiments, the sustained release composition includes about 5% to about 30% of the first component, about 30 to about 80% of the second component, and about 15% to about 40% of the third component. In the second component, the weight ratio of the bioavailable curcumin composition to the release rate controlling excipient is about 10:1. In the third component the weight ratio of the bioavailable curcumin to the release rate controlling excipient ranges from about 3:1 to about 50:1. In some embodiments, the sustained release curcuminoid composition includes about 5% to about 30% of the first component, about 30 to about 80% of the second component, and about 15% to about 40% of a third component. The second component includes the bioavailable curcumin composition and shellac, in a weight ratio of bioavailable curcumin composition to shellac of about 10:1. The third component includes the bioavailable curcumin composition and shellac, and the weight ratio of the bioavailable curcumin composition to shellac is about 14:1.

In some embodiments, the sustained release curcuminoid composition includes about 10% of the first component, about 60% of the second component, and about 30% of a third component. The second component includes bioavailable curcumin composition and shellac in the weight ratio of the bioavailable curcumin composition to shellac of about 10:1. The third component includes bioavailable curcumin composition and shellac, and the weight ratio of the bioavailable curcumin composition to shellac is about 14:1.

In some embodiments, the sustained release curcuminoid composition includes about 5% to about 30% of the first component, about 30 to about 80% of the second component, and, about 15% to about 40% of a third component. The second component includes the bioavailable curcumin composition and the ethyl cellulose, and the weight ratio of the bioavailable curcumin composition to the ethyl cellulose is about 10:1. The third component includes the bioavailable curcumin composition and the ethyl cellulose, and the weight ratio of the bioavailable curcumin composition to the ethyl cellulose is about 20:1.

In some embodiments, the sustained release curcuminoid composition includes about 10% of the first component, about 60% of the second component, and, about 30% of a third component. The second component includes the bioavailable curcumin composition and ethyl cellulose, and in a weight ratio of the bioavailable curcumin composition to the ethyl cellulose of about 10:1. The third component includes the bioavailable curcumin composition and ethyl cellulose, and in a weight ratio of the bioavailable curcumin composition to the ethyl cellulose of about 20:1.

In some embodiments the sustained release curcuminoid composition having the first component, the second component and the third component is administered orally. In some embodiments, a dosage form of the sustained release curcuminoid composition is disclosed for oral administration. The dosage forms include powder, pellets, granules, tablets or capsules. In some embodiments of the sustained release curcuminoid composition curcumin, demethoxycurcumin and bisdemethoxycurcumin are detected in the blood for about 24 to about 36 hours. In some embodiments of the sustained release curcuminoid composition, administering a single dosage of the sustained release curcuminoid composition provides curcumin, demethoxycurcumin and bisdemethoxycurcumin in the body for 24 hours. In some embodiments, administering a single dosage of the sustained release curcuminoid composition provides curcumin, demethoxycurcumin and bisdemethoxycurcumin in the body for 36 hours. In some embodiments, administering a single dosage of the sustained release curcuminoid composition provides bioavailability of curcumin, demethoxycurcumin and bisdemethoxycurcumin in the blood for 24 hours when compared to administration of the bioavailable curcumin composition alone. In some embodiments, administering a single dosage of the sustained release curcuminoid composition enhances bioavailability of curcumin, demethoxycurcumin and bisdemethoxycurcumin in the blood for 24 hours when compared to administration of the bioavailable curcumin composition alone. In some embodiments, administering a single dosage of the sustained release curcuminoid composition enhances bioavailability of curcumin, demethoxycurcumin and bisdemethoxycurcumin in the blood for 36 hours when compared to administration of the bioavailable curcumin composition alone. In some embodiments, administering a single dosage of the sustained release curcuminoid composition enhances bioavailability of curcumin, demethoxycurcumin and bisdemethoxycurcumin in body tissues for more than 24 hours when compared to administration of the bioavailable curcumin composition alone. In some embodiments, the half-life ($t_{1/2}$) of the curcumin, demethoxycurcumin and bisdemethoxycurcumin in the blood is increased when compared to the half-life ($t_{1/2}$) of curcumin, demethoxycurcumin and bisdemethoxycurcumin in the blood upon administration of the bioavailable curcumin composition alone. In some embodiments, the area under the curve (AUC) of the curcumin, demethoxycurcumin and bisdemethoxycurcumin in the blood is increased when compared to the AUC of curcumin, demethoxycurcumin and bisdemethoxycurcumin upon administration of the bioavailable curcumin composition.

In some embodiments a method of preparing a sustained release curcuminoid composition is provided. The method includes suspending the curcuminoid mixture in water to form a suspension. Then essential oil of turmeric is added to the suspension to form a second mixture. Then the second mixture is homogenized to obtain a slurry. Next the slurry is dried under heat and vacuum to obtain a uniform blend of the bioavailable curcumin composition. Then the bioavailable curcumin composition is dissolved in ethyl acetate to obtain a solution of the bioavailable curcumin composition. The solution of the bioavailable curcumin composition is mixed with a solution of ethyl cellulose dissolved in ethanol to obtain a mixture having the first weight ratio of the bioavailable curcumin composition to the ethyl cellulose. The mixture is evaporated at 50° C. under reduced pressure to obtain the second component The dried uniform blend of the bioavailable curcumin composition is sprayed with a solution of ethyl cellulose dissolved in ethanol to obtain ethyl cellulose coated bioavailable curcumin composition. The ethyl cellulose coated bioavailable curcumin composition has the second weight ratio of the bioavailable curcumin composition to the ethyl cellulose.

In some embodiments, a 5% solution of ethyl cellulose dissolved in ethanol is sprayed on a powder of bioavailable curcumin composition to obtain an ethyl cellulose coated sustained release curcuminoid composition having the second weight ratio of the bioavailable curcumin composition to the ethyl cellulose. The ethyl cellulose coated sustained release curcuminoid product is dried at 50° C. for 2 hours under reduced pressure to obtain the third component. The bioavailable curcumin composition, the second component and the third component are mixed to obtain another sustained release composition. The sustained release curcuminoid product can be stored at room temperature.

Some embodiments provide a method of preparing the sustained release curcuminoid composition. The method includes suspending the curcuminoid mixture in water to form a suspension. Then essential oil of turmeric is added to the suspension to form a second mixture. Then the second mixture is homogenized to obtain a slurry. Next the slurry is dried under heat and vacuum to obtain a uniform blend of the bioavailable curcumin composition. Then the bioavailable curcumin composition is dissolved in ethyl acetate to obtain a solution of the bioavailable curcumin composition. The solution of the bioavailable curcumin composition is mixed with a solution having a copolymer of ethyl acrylate and methyl methacrylate to obtain a mixture. The mixture is evaporated at 50° C. under reduced pressure to obtain the sustained release curcuminoid composition. The solution having the copolymer of ethyl acrylate and methyl methacrylate is prepared by dissolving the copolymer of ethyl acrylate and methyl methacrylate in a solution having a 1:1 ratio of methanol:ethyl acetate.

Some embodiments provide a method of preparing the sustained release curcuminoid composition. The method includes suspending the curcuminoid mixture in water to form a suspension. Then essential oil of turmeric is added to the suspension to form a second mixture. Then the second mixture is homogenized to obtain a slurry. Next the slurry is dried under heat and vacuum to obtain a uniform blend of the bioavailable curcumin composition. Then the bioavailable curcumin composition is dissolved in ethyl acetate to obtain a solution of the bioavailable curcumin composition. The solution of the bioavailable curcumin composition is mixed with a solution having a release rate controlling excipient to form a mixture. The mixture is evaporated at 50° C. under reduced pressure to obtain the sustained release curcuminoid composition. The solution having the release rate controlling excipient is prepared by dissolving shellac, a copolymer of ethyl acetate and methyl methacrylate, ethyl cellulose and hydroxyl propyl methyl cellulose in a solution having a 1:1 ratio of methanol to ethyl acetate.

Some embodiments provide a method of preparing the sustained release curcuminoid composition. The method includes suspending the curcuminoid mixture in water to form a suspension. Then essential oil of turmeric is added to the suspension to form a second mixture. Then the second mixture is homogenized to obtain a slurry. Next the slurry is dried under heat and vacuum to obtain a uniform blend of the bioavailable curcumin composition. Then the bioavailable curcumin composition is dissolved in ethyl acetate to obtain a solution of the bioavailable curcumin composition. The solution of the bioavailable curcumin composition is mixed with a shellac solution to obtain a mixture having the first weight ratio of the bioavailable curcumin composition to the shellac. The shellac solution is prepared by dissolving shellac in ethanol. The mixture is evaporated at 50° C. under reduced pressure to obtain the second component. The solution of the bioavailable curcumin composition is mixed with a shellac solution to obtain a mixture having the second weight ratio of the bioavailable curcumin composition to the shellac. The solution is evaporated at 50° C. under reduced pressure to obtain the third component. Next the bioavailable curcumin composition, the second component and the third component are mixed to obtain the sustained release composition.

It will be readily understood by the skilled artisan that numerous alterations may be made to the examples and instructions given herein. These and other objects and features of disclosed embodiments will be made apparent from the following examples. The following examples as described are not intended to be construed as limiting the scope of the disclosure.

EXAMPLES

Example 1

Method of Preparation of Regular Turmeric Extract

The rhizomes of turmeric (500 Kg) were dried. The dried turmeric rhizomes were powdered to form powdered turmeric. Ethyl acetate extraction of the powdered turmeric was performed. For the extraction, ethyl acetate (1500 L) was added to the powdered turmeric at 78° C. temperature and extracted for 1 hr. After ethyl acetate extraction a solution and a residue 1 were obtained. The residue 1 was separated from the solution and 1500 liters of ethyl acetate was again added to the residue 1 for extraction at 78° C. temperature for 1 hr. The resultant residue was similarly extracted with ethyl acetate for three more times. The solution from each of the ethyl acetate extraction steps was combined and filtered. The solvent from the filtered solution was stripped to form an extract. Then the extract was cooled to about 4° C. to obtain crystals of curcuminoid (20 Kg) and a liquid. The crystals of curcuminoid were isolated from the liquid by filtration. The crystal of curcuminoid included mixture of curcumin (78.16%), demethoxycurcumin (13.79%) and bis-demethoxycurcumin (2.87%). The crystals of curcuminoids are referred to as regular turmeric extract.

Example 2

Preparation of Fractions of Essential Oil of Turmeric

The rhizomes of turmeric (500 Kg) were dried. The dried turmeric rhizomes were powdered to form powdered turmeric. Ethyl acetate extraction of the powdered turmeric was performed. For the extraction, ethyl acetate (1500 L) was added to the powdered turmeric at 78° C. temperature and extracted for 1 hr. After ethyl acetate extraction a solution and a residue 1 were obtained. The residue 1 was separated from the solution and 1500 liters of ethyl acetate was again added to the residue 1 for extraction at 78° C. temperature for 1 hr. The resultant residue was similarly extracted with ethyl acetate for three more times. The solution from each of the ethyl acetate extraction steps was combined and filtered. The solvent from the filtered solution was stripped to form an extract. Then the extract was cooled to about 4° C. to obtain crystals of curcuminoid and a liquid. The crystals of curcuminoid were isolated from the liquid by filtration. The crystal of curcuminoid included mixture of curcumin, demethoxycurcumin and bisdemethoxycurcumin. The crystals of curcuminoid are referred to as regular turmeric extract.

The liquid included essential oil of turmeric, flavouring compounds, any impurities that remained in solution, and, curcuminoids that did not crystallize. The liquid was then steam distilled to isolate essential oil of turmeric having 10-15% Ar-turmerone (25 Kg) and a residue 2. The essential oil having 10-15% Ar-turmerone was fractionated to obtain three fractions. Essential oil of turmeric having 2-3% Ar-turmerone (9.3 Kg) was obtained at 110° C. and designated as fraction 1. Essential oil of turmeric having 4-5% Ar-turmerone (8.3 Kg) was obtained at 125° C. and designated as fraction 2. Essential oil of turmeric having 45% Ar-turmerone (7.5 Kg) was obtained at 140° C. and designated as fraction 3.

Example 3

Method of Preparation of Curcuminoids Blended with Essential Oil of Turmeric Having 45% Ar-Turmerone in 10:1 Ratio 2.7 Kg of turmeric extract (From Example 1) was suspended in water (12 L) to form a suspension. From Example 2, the fraction of essential oil (fraction 3) having 45% Ar-turmerone (0.27 Kg) was added to the suspension in a 10:1 ratio of turmeric extract:essential oil of turmeric to obtain a mixture of turmeric extract and essential oil of turmeric. The mixture of turmeric extract blended with essential oil of turmeric was pulverized in a colloidal mill to form fine slurry. Water was stripped from the slurry under heat and vacuum to form a uniform blend (3 Kg) containing curcuminoids and essential oil of turmeric having 45% Ar-turmerone in 10:1 ratio. This blend contains 69.8% curcumin, 17.0% demethoxy curcumin, 3.2% bisdemethoxy curcumin and 8.8% essential oil of turmeric having 45% Ar-turmerone.

Example 4

Method of Preparation of Curcuminoids Blended with Essential Oil of Turmeric Having 45% Ar-Turmerone in 12:1 Ratio 3.5 Kg of turmeric extract (From Example 1) was suspended in water (15 L) to form a suspension. From Example 2, the fraction of essential oil (fraction 3) having 45% Ar-turmerone (0.29 Kg) was added to the suspension in a 12:1 ratio of turmeric extract:essential oil of turmeric to obtain a mixture of turmeric extract and essential oil of turmeric. The mixture of turmeric extract blended with essential oil of turmeric was pulverized in a colloidal mill to form fine slurry. Water was stripped from the slurry under heat and vacuum to form a uniform blend (3.8 Kg) containing curcuminoids and essential oil of turmeric having 45% Ar-turmerone in 12:1 ratio. This blend contains 70.0% curcumin, 17.1% demethoxy curcumin, 3.3% bisdemethoxy curcumin and 7.3% essential oil of turmeric having 45% Ar-turmerone.

Example 5

The curcuminoids blended with essential oil of turmeric having 45% Ar-turmerone in 10:1 ratio (from Example 3) was combined with ethyl cellulose in a 10:1 weight/weight ratio as shown in Table 1 below to form a bioavailable curcumin sustained-release composition. The sustained release composition had 68% Curcumin, 12% Demethoxy curcumin, 2.5% Bisdemethoxy curcumin, 6% Essential oil of turmeric having 45% Ar-turmerone and 9% Ethyl cellulose.

TABLE 1

| S. No. | Ingredients | Quantity (gm) |
|---|---|---|
| 1 | Curcuminoids blended with essential oil of turmeric having 45% Ar-turmerone in 10:1 ratio | 10 |
| 2 | Ethyl cellulose | 1 |

Weighed quantity of curcuminoids blended with essential oil of turmeric having 45% Ar-turmerone in 10:1 ratio (from Example 3) was dissolved in 50 ml of ethyl acetate by stirring and heating at 50° C. to form solution of curcuminoids blended with essential oil of turmeric having 45% Ar-turmerone in 10:1 ratio. The solution was filtered and kept in a 100 ml beaker (Solution of curcuminoids blended with essential oil of turmeric having 45% Ar-turmerone in 10:1 ratio was referred to as Solution A). Similarly, weighed quantity of Ethyl cellulose was dissolved in 25 ml of Ethanol and filtered to form solution of ethyl cellulose referred to as Solution B). Solution A was mixed with Solution B and the mixture was stirred at 500 rpm for 30 min using a mechanical stirrer. The resultant solution was kept in a round bottom flask and solvent was evaporated completely at 50° C. under reduced pressure to get the curcumin sustained-release product in 10:1 ratio.

Example 6

The curcuminoids blended with essential oil of turmeric having 45% Ar-turmerone in 12:1 ratio (from Example 4) was combined with ethyl cellulose in a 10:1 weight/weight ratio as shown in Table 2 below to form a bioavailable curcumin sustained-release composition. The sustained release composition had 68.5% Curcumin, 12.5% Demethoxy curcumin, 2.5% Bisdemethoxy curcumin, 5% Essential oil of turmeric having 45% Ar-turmerone and 9% Ethyl cellulose.

TABLE 2

| S. No. | Ingredients | Quantity (gm) |
|---|---|---|
| 1 | Curcuminoids blended with essential oil of turmeric having 45% Ar-turmerone in 12:1 ratio | 10 |
| 2 | Ethyl cellulose | 1 |

Weighed quantity of curcuminoids blended with essential oil of turmeric having 45% Ar-turmerone in 12:1 ratio (from Example 4) was dissolved in 50 ml of ethyl acetate by stirring and heating at 50° C. to from solution of curcuminoids blended with essential oil of turmeric having 45% Ar-turmerone in 12:1 ratio. The solution was filtered and kept in a 100 ml beaker (Solution of curcuminoids blended with essential oil of turmeric having 45% Ar-turmerone in 12:1 ratio was referred to as Solution A). Similarly, weighed quantity of ethyl cellulose was dissolved in 25 ml of ethanol and filtered to form solution of ethyl cellulose referred to as Solution B. Solution A was mixed with Solution B and the mixture was stirred at 500 rpm for 30 min using a mechanical stirrer. The resultant solution was kept in a round bottom flask and solvent was evaporated completely at 50° C. under reduced pressure to get the curcumin sustained-release product in 10:1 ratio.

Example 7

The regular turmeric extract (from Example 1) was combined with ethyl cellulose in a 10:1 weight/weight ratio as shown in Table 3 below to form a curcumin sustained-release composition. The sustained release composition had 72% Curcumin, 12% Demethoxy curcumin, 3% Bisdemethoxy curcumin and 9% Ethyl cellulose.

TABLE 3

| S. No. | Ingredients | Quantity (gm) |
| --- | --- | --- |
| 1 | Regular turmeric extract | 10 |
| 2 | Ethyl cellulose | 1 |

Weighed quantity of regular turmeric extract (from Example 1) was dissolved in 50 ml of ethyl acetate by stirring and heating at 50° C. to from solution of regular turmeric extract. The solution was filtered and kept in a 100 ml beaker (Solution of regular turmeric extract was referred as Solution A). Similarly, weighed quantity of ethyl cellulose was dissolved in 25 ml of ethanol and filtered to form solution of ethyl cellulose referred as Solution B. Solution A was mixed with Solution B and the mixture was stirred at 500 rpm for 30 min using a mechanical stirrer. The resultant solution was kept in a round bottom flask and solvent was evaporated completely at 50° C. under reduced pressure to get the regular turmeric extract sustained release product in 10:1 ratio.

Example 8

The curcuminoids blended with essential oil of turmeric having 45% Ar-turmerone in 10:1 ratio (from Example 3) was combined with ethyl cellulose in a 50:2.5 weight/weight ratio as shown in Table 4 below to form a bioavailable curcumin sustained-release composition. The sustained release composition had 69% Curcumin, 13% Demethoxy curcumin, 3% Bisdemethoxy curcumin, 6% Essential oil of turmeric having 45% Ar-turmerone and 5% Ethyl cellulose.

TABLE 4

| S. No. | Ingredients | Quantity (gm) |
| --- | --- | --- |
| 1 | Curcuminoids blended with essential oil of turmeric having 45% Ar-turmerone in 10:1 ratio | 500 |
| 2 | Ethyl cellulose | 25 |

Weighed quantity of ethyl cellulose was dissolved in 500 ml of ethanol by stirring and heating at 50° C. to get 5% solution of ethyl cellulose in ethanol. The solution was filtered and kept for spraying (5% solution of ethyl cellulose was referred as Solution A). Curcuminoids blended with essential oil of turmeric having 45% Ar-turmerone in 10:1 ratio (from Example 3) was taken as a fine powder and passed through a sieve of 60 mesh. The sieved material was used to make sustained release formulation. The ethyl cellulose solution (Solution A) was sprayed on the sieved material using a sprayer. The obtained sustained release product was dried at 50° C. for 2 hours and stored at room temperature.

Example 9

The curcuminoids blended with essential oil of turmeric having 45% Ar-turmerone in 12:1 ratio (from Example 4) was combined with ethyl cellulose in a 50:2.5 weight/weight ratio as shown in Table 5 below to form a bioavailable curcumin sustained-release composition. The sustained release composition had 69.5% Curcumin, 13.5% Demethoxy curcumin, 3% Bisdemethoxy curcumin, 5% Essential oil of turmeric having 45% Ar-turmerone and 5% Ethyl cellulose.

TABLE 5

| S. No. | Ingredients | Quantity (gm) |
| --- | --- | --- |
| 1 | Curcuminoids blended with essential oil of turmeric having 45% Ar-turmerone in 12:1 ratio | 500 |
| 2 | Ethyl cellulose | 25 |

Weighed quantity of ethyl cellulose was dissolved in 500 ml of ethanol by stirring and heating at 50° C. to get 5% solution of ethyl cellulose in ethanol. The solution was filtered and kept for spraying (5% solution of ethyl cellulose in ethanol was referred as Solution A). Curcuminoids blended with essential oil of turmeric having 45% Ar-turmerone in 12:1 ratio (from Example 4) was taken as a fine powder and passed through a sieve of 60 mesh. The sieved material was used to make sustained release formulation. The ethyl cellulose solution (Solution A) was sprayed on the sieved material using a sprayer. The obtained sustained release product was dried at 50° C. for 2 hours and stored at room temperature.

Example 10

The regular turmeric extract (from Example 1) was combined with ethyl cellulose in a 50:2.5 weight/weight ratio as shown in Table 6 below to form a curcumin sustained-release composition. The sustained release composition had 74% Curcumin, 14% Demethoxy curcumin, 3% Bisdemethoxy curcumin and 5% ethyl cellulose.

TABLE 6

| S. No. | Ingredients | Quantity (gm) |
| --- | --- | --- |
| 1 | Regular turmeric extract | 500 |
| 2 | Ethyl cellulose | 25 |

Weighed quantity of ethyl cellulose was dissolved in 500 ml of ethanol by stirring and heating at 50° C. to get 5% solution of ethyl cellulose in ethanol. The solution was filtered and kept for spraying (5% solution of ethyl cellulose in ethanol was referred as Solution A). Regular turmeric extract (from Example 1) was taken as a fine powder and passed through a sieve of 60 mesh. The sieved material was used to make sustained release formulation. The ethyl cellulose solution (Solution A) was sprayed on the sieved material using a sprayer. The obtained sustained release product was dried at 50° C. for 2 hours and stored at room temperature.

Example 11

The curcuminoids blended with essential oil of turmeric having 45% Ar-turmerone in 10:1 ratio (from Example 3) was combined with copolymer of ethyl acrylate and methyl methacrylate in a 10:1 weight/weight ratio as shown in Table 7 below to form a bioavailable curcumin sustained-release composition. The sustained release composition had 68% Curcumin, 12% Demethoxy curcumin, 2.5% Bisdemethoxy curcumin, 6% essential oil of turmeric having 45% Ar-turmerone and 9% Copolymer of ethyl acrylate and methyl methacrylate.

TABLE 7

| S. No. | Ingredients | Quantity (gm) |
|---|---|---|
| 1 | Curcuminoids blended with essential oil of turmeric having 45% Ar-turmerone in 10:1 ratio | 10 |
| 2 | Copolymer of ethyl acrylate and methyl methacrylate | 1 |

Weighed quantity of curcuminoids blended with essential oil of turmeric having 45% Ar-turmerone in 10:1 ratio (from Example 3) was dissolved in 50 ml of ethyl acetate by stirring and heating at 50° C. to form solution of curcuminoids blended with essential oil of turmeric having 45% Ar-turmerone in 10:1 ratio. The solution was filtered and kept in a 100 ml beaker (solution of curcuminoids blended with essential oil of turmeric having 45% Ar-turmerone in 10:1 ratio was referred as Solution A). Similarly, weighed quantity of copolymer of ethyl acrylate and methyl methacrylate was dissolved in 25 ml of Methanol/Ethyl acetate (1:1) and filtered to form solution of copolymer of ethyl acrylate and methyl methacrylate referred as Solution B. Solution A was mixed with Solution B and the mixture was stirred at 500 rpm for 30 min using a mechanical stirrer. The resultant solution was kept in a round bottom flask and solvent was evaporated completely at 50° C. under reduced pressure to get the sustained release product in 10:1 ratio.

Example 12

The curcuminoids blended with essential oil of turmeric having 45% Ar-turmerone in 12:1 ratio (from Example 4) was combined with copolymer of ethyl acrylate and methyl methacrylate in a 10:1 weight/weight ratio as shown in Table 8 below to form a bioavailable curcumin sustained-release composition. The sustained release composition had 68.5% curcumin, 12.5% Demethoxy curcumin, 2.5% Bisdemethoxy curcumin, 5% essential oil of turmeric having 45% Ar-turmerone and 9% Copolymer of ethyl acrylate and methyl methacrylate.

TABLE 8

| S. No. | Ingredients | Quantity (gm) |
|---|---|---|
| 1 | Curcuminoids blended with essential oil of turmeric having 45% Ar-turmerone in 12:1 ratio | 10 |
| 2 | Copolymer of ethyl acrylate and methyl methacrylate | 1 |

Weighed quantity of curcuminoid blended with essential oil of turmeric having 45% Ar-turmerone in 12:1 ratio (from Example 4) was dissolved in 50 ml of ethyl acetate by stirring and heating at 50° C. to form solution of curcuminoids blended with essential oil of turmeric having 45% Ar-turmerone in 12:1 ratio. The solution was filtered and kept in a 100 ml beaker (solution of curcuminoids blended with essential oil of turmeric having 45% Ar-turmerone in 12:1 ratio was referred as Solution A). Similarly, weighed quantity of copolymer of ethyl acrylate and methyl methacrylate was dissolved in 25 ml of Methanol/Ethyl acetate (1:1) and filtered to form solution of copolymer of ethyl acrylate and methyl methacrylate referred as Solution B. Solution A was mixed with Solution B and the mixture was stirred at 500 rpm for 30 min using a mechanical stirrer. The resultant solution was kept in a round bottom flask and solvent was evaporated completely at 50° C. under reduced pressure to get the sustained release product in 10:1 ratio.

Example 13

The regular turmeric extract (from Example 1) was combined with copolymer of ethyl acrylate and methyl methacrylate in a 10:1 weight/weight ratio as shown in Table 9 below to form a curcumin sustained-release composition. The sustained release composition had 72% curcumin, 12% Demethoxy curcumin, 3% Bisdemethoxy curcumin and 9% Copolymer of ethyl acrylate and methyl methacrylate.

TABLE 9

| S. No. | Ingredients | Quantity (gm) |
|---|---|---|
| 1 | Regular turmeric extract | 10 |
| 2 | Copolymer of ethyl acrylate and methyl methacrylate | 1 |

Weighed quantity of Regular turmeric extract (from Example 1) was dissolved in 50 ml of ethyl acetate by stirring and heating at 50° C. to form solution of regular turmeric extract. The solution was filtered and kept in a 100 ml beaker (solution of regular turmeric extract was referred as Solution A). Similarly, weighed quantity of copolymer of ethyl acrylate and methyl methacrylate was dissolved in 25 ml of Methanol/Ethyl acetate (1:1) and filtered to form solution of copolymer of ethyl acrylate and methyl methacrylate referred as Solution B. Solution A was mixed with Solution B and the mixture was stirred at 500 rpm for 30 min using a mechanical stirrer. The resultant solution was kept in a round bottom flask and solvent was evaporated completely at 50° C. under reduced pressure to get the sustained release product in 10:1 ratio.

Example 14

The curcuminoids blended with essential oil of turmeric having 45% Ar-turmerone in 10:1 ratio prepared (from Example 3) was combined with Shellac, Copolymer of ethyl acrylate and methyl methacrylate, Ethyl cellulose, and Hydroxy propyl methyl cellulose as shown in Table 10 below to form a bioavailable curcumin sustained release composition. The sustained release composition had 68% Curcumin, 12% Demethoxy curcumin, 2.5% Bisdemethoxy curcumin, 6% essential oil of turmeric having 45% Ar-turmerone, 2.5% shellac, 1.5% Copolymer of ethyl acrylate and methyl methacrylate, 4% ethyl cellulose and 1% Hydroxy propyl methyl cellulose.

TABLE 10

| S. No. | Ingredients | Quantity (gm) |
|---|---|---|
| 1 | Curcuminoid blended with essential oil of turmeric having 45% Ar-turmerone in 10:1 ratio | 10 |
| 2 | Shellac | 0.3 |
| 3 | Copolymer of ethyl acrylate and methyl methacrylate | 0.2 |
| 4 | Ethyl cellulose | 0.4 |
| 5 | Hydroxy propyl methyl cellulose | 0.1 |

Weighed quantity of curcuminoid blended with essential oil of turmeric having 45% Ar-turmerone in 10:1 ratio (from Example 3) was dissolved in 50 ml of ethyl acetate by stirring and heating at 50° C. to form solution of curcuminoid blended with essential oil of turmeric having 45% Ar-turmerone in 10:1 ratio. The solution was filtered and kept in a 100 ml beaker (solution of curcuminoid blended with essential oil of turmeric having 45% Ar-turmerone in 10:1 ratio referred as Solution A). Similarly, weighed quantity of Shellac, copolymer of ethyl acrylate and methyl methacrylate, Ethyl cellulose and Hydroxy propyl methyl cellulose were dissolved in 50 ml of Methanol/Ethyl acetate (1:1) mixture and filtered to from solution of different polymers mentioned above and is referred as Solution B. Solution A was mixed with Solution B and the mixture was stirred at 500 rpm for 30 min using a mechanical stirrer. The resultant solution was kept in a round bottom flask and solvent was evaporated completely at 50° C. under reduced pressure to get the sustained release product in 10:0.3:0.2:0.4:0.1 ratio.

Example 15

The curcuminoids blended with essential oil of turmeric having 45% Ar-turmerone in 10:1 ratio (from Example 3) was combined with shellac in a 14:1 weight/weight ratio as shown in Table 11 below to form a bioavailable curcumin sustained-release composition. The sustained release composition had 67.9% Curcumin, 14.2% Demethoxy curcumin, 2.9% Bisdemethoxy curcumin, 8.5% Essential oil of turmeric having 45% Ar-turmerone and 6.5% shellac.

TABLE 11

| S. No. | Ingredients | Quantity (gm) |
|---|---|---|
| 1 | Curcuminoids blended with essential oil of turmeric having 45% Ar-turmerone in 10:1 ratio | 14 |
| 2 | Shellac | 1 |

Weighed quantity of curcuminoids blended with essential oil of turmeric having 45% Ar-turmerone in 10:1 ratio (from Example 3) was dissolved in 50 ml of ethyl acetate by stirring and heating at 50° C. to form a solution of curcuminoids blended with essential oil of turmeric having 45% Ar-turmerone in 10:1 ratio. The solution was filtered and kept in a 100 ml beaker (solution of curcuminoids blended with essential oil of turmeric having 45% Ar-turmerone in 10:1 ratio was referred as Solution A). Similarly, weighed quantity of shellac was dissolved in 25 ml of Ethanol and filtered to form solution of shellac referred as Solution B. Solution A was mixed with Solution B and the mixture was stirred at 500 rpm for 30 min using a mechanical stirrer. The resultant solution was kept in a round bottom flask and solvent was evaporated completely at 50° C. under reduced pressure to get the curcumin sustained-release product in 14:1 ratio.

Example 16

The curcuminoids blended with essential oil of turmeric having 45% Ar-turmerone in 12:1 ratio (from Example 4) was combined with shellac in a 14:1 weight/weight ratio as shown in Table 12 below to form a bioavailable curcumin sustained-release composition. The sustained release composition had 68.7% Curcumin, 14.6% Demethoxy curcumin, 3% Bisdemethoxy curcumin, 7.2% Essential oil of turmeric having 45% Ar-turmerone and 6.5% shellac.

TABLE 12

| S. No. | Ingredients | Quantity (gm) |
|---|---|---|
| 1 | Curcuminoids blended with essential oil of turmeric having 45% Ar-turmerone in 12:1 ratio | 14 |
| 2 | Shellac | 1 |

Weighed quantity of curcuminoids blended with essential oil of turmeric having 45% Ar-turmerone in 12:1 ratio (from Example 4) was dissolved in 50 ml of ethyl acetate by stirring and heating at 50° C. to form solution of curcuminoids blended with essential oil of turmeric having 45% Ar-turmerone in 12:1 ratio. The solution was filtered and kept in a 100 ml beaker (solution of curcuminoids blended with essential oil of turmeric having 45% Ar-turmerone in 12:1 ratio was referred as Solution A). Similarly, weighed quantity of shellac was dissolved in 25 ml of ethanol and filtered to form solution of shellac referred as Solution B. Solution A was mixed with Solution B and the mixture was stirred at 500 rpm for 30 min using a mechanical stirrer. The resultant solution was kept in a round bottom flask and solvent was evaporated completely at 50° C. under reduced pressure to get the curcumin sustained-release product in 14:1 ratio.

Example 17

The curcuminoids blended with essential oil of turmeric having 45% Ar-turmerone in 10:1 ratio (from Example 3) was combined with shellac in a 10:1 weight/weight ratio as shown in Table 13 below to form a bioavailable curcumin sustained-release composition. The sustained release composition had 66.7% Curcumin, 13.6% Demethoxy curcumin, 2.7% Bisdemethoxy curcumin, 8.3% Essential oil of turmeric having 45% Ar-turmerone and 8.7% shellac.

TABLE 13

| S. No. | Ingredients | Quantity (gm) |
|---|---|---|
| 1 | Curcuminoids blended with essential oil of turmeric having 45% Ar-turmerone in 10:1 ratio | 10 |
| 2 | Shellac | 1 |

Weighed quantity of curcuminoids blended with essential oil of turmeric having 45% Ar-turmerone in 10:1 ratio (from Example 3) was dissolved in 50 ml of ethyl acetate by stirring and heating at 50° C. to form a solution of curcuminoids blended with essential oil of turmeric having 45% Ar-turmerone in 10:1 ratio. The solution was filtered and kept in a 100 ml beaker (solution of curcuminoids blended with essential oil of turmeric having 45% Ar-turmerone in 10:1 ratio was referred as Solution A). Similarly, weighed quantity of shellac was dissolved in 25 ml of Ethanol and filtered to form solution of shellac referred as Solution B. Solution A was mixed with Solution B and the mixture was stirred at 500 rpm for 30 min using a mechanical stirrer. The resultant solution was kept in a round bottom flask and solvent was evaporated completely at 50° C. under reduced pressure to get the curcumin sustained-release product in 10:1 ratio.

Example 18

The curcuminoids blended with essential oil of turmeric having 45% Ar-turmerone in 12:1 ratio (from Example 4) was combined with shellac in a 10:1 weight/weight ratio as shown in Table 14 below to form a bioavailable curcumin sustained-release composition. The sustained release composition had 67.6% Curcumin, 13.9% Demethoxy curcumin, 2.8% Bisdemethoxy curcumin, 7% Essential oil of turmeric having 45% Ar-turmerone and 8.7% shellac.

TABLE 14

| S. No. | Ingredients | Quantity (gm) |
|---|---|---|
| 1 | Curcuminoids blended with essential oil of turmeric having 45% Ar-turmerone in 12:1 ratio | 10 |
| 2 | Shellac | 1 |

Weighed quantity of curcuminoids blended with essential oil of turmeric having 45% Ar-turmerone in 12:1 ratio (from Example 4) was dissolved in 50 ml of ethyl acetate by stirring and heating at 50° C. to form solution of curcuminoids blended with essential oil of turmeric having 45% Ar-turmerone in 12:1 ratio. The solution was filtered and kept in a 100 ml beaker (solution of curcuminoids blended with essential oil of turmeric having 45% Ar-turmerone in 12:1 ratio was referred as Solution A). Similarly, weighed quantity of shellac was dissolved in 25 ml of ethanol and filtered to from solution of shellac referred as Solution B. Solution A was mixed with Solution B and the mixture was stirred at 500 rpm for 30 min using a mechanical stirrer. The resultant solution was kept in a round bottom flask and solvent was evaporated completely at 50° C. under reduced pressure to get the curcumin sustained-release product in 10:1 ratio.

Example 19

The regular turmeric extract (from Example 1) was combined with shellac in a 14:1 weight/weight ratio as shown in Table 15 below to form a curcumin sustained-release composition. The sustained release composition had 72.1% Curcumin, 17.9% Demethoxy curcumin, 3.5% Bisdemethoxy curcumin and 6.5% Shellac.

TABLE 15

| S. No. | Ingredients | Quantity (gm) |
|---|---|---|
| 1 | Regular turmeric extract | 14 |
| 2 | Shellac | 1 |

Weighed quantity of regular turmeric extract (from Example 1) was dissolved in 50 ml of ethyl acetate by stirring and heating at 50° C. to form solution of regular turmeric extract. The solution was filtered and kept in a 100 ml beaker (solution of regular turmeric extract was referred as Solution A. Similarly, weighed quantity of shellac was dissolved in 25 ml of ethanol and filtered to form solution of shellac referred as Solution B. Solution A was mixed with Solution B and the mixture was stirred at 500 rpm for 30 min using a mechanical stirrer. The resultant solution was kept in a round bottom flask and solvent was evaporated completely at 50° C. under reduced pressure to get the product in 14:1 ratio.

Example 20

The regular turmeric extract (from Example 1) was combined with shellac in a 10:1 weight/weight ratio as shown in Table 16 below to form a curcumin sustained-release composition. The sustained release composition had 70.7% Curcumin, 17.3% Demethoxy curcumin, 3.3% Bisdemethoxy curcumin and 8.7% Shellac.

TABLE 16

| S. No. | Ingredients | Quantity (gm) |
|---|---|---|
| 1 | Regular turmeric extract | 10 |
| 2 | Shellac | 1 |

Weighed quantity of regular turmeric extract (from Example 1) was dissolved in 50 ml of ethyl acetate by stirring and heating at 50° C. to form solution of regular turmeric extract. The solution was filtered and kept in a 100 ml beaker (solution of regular turmeric extract was referred as Solution A). Similarly, weighed quantity of shellac was dissolved in 25 ml of ethanol and filtered to form solution of shellac referred as Solution B. Solution A was mixed with Solution B and the mixture was stirred at 500 rpm for 30 min using a mechanical stirrer. The resultant solution was kept in a round bottom flask and solvent was evaporated completely at 50° C. under reduced pressure to get the product in 10:1 ratio.

Example 21

The curcuminoids blended with essential oil of turmeric having 45% Ar-turmerone in 12:1 ratio prepared (from Example 4) was blended with 14:1 ratio of bioavailable curcumin sustained-release composition coated with shellac (from example 16) and 10:1 ratio of bioavailable curcumin sustained-release composition coated with shellac (from example 18) as shown in Table 17 below to form a bioavailable curcumin sustained release composition. The sustained release composition had 68.37% Curcumin, 14.45% Demethoxy curcumin, 2.91% Bisdemethoxy curcumin, 7.1% essential oil of turmeric having 45% Ar-turmerone, 7.17% shellac.

TABLE 17

| S. No. | Ingredients | Quantity (gm) |
|---|---|---|
| 1 | Curcuminoid blended with essential oil of turmeric having 45% Ar-turmerone in 12:1 ratio | 10 |
| 2 | Bioavailable curcumin sustained-release composition coated with | 60 |

TABLE 17-continued

| S. No. | Ingredients | Quantity (gm) |
|---|---|---|
| 3 | Bioavailable curcumin sustained-release composition coated with shellac 14:1 ratio | 30 |

Weighed quantity of curcuminoid blended with essential oil of turmeric having 45% Ar-turmerone in 12:1 ratio (from Example 4) was dissolved in 50 ml of ethyl acetate by stirring and heating at 50° C. to form solution of curcuminoid blended with essential oil of turmeric having 45% Ar-turmerone in 12:1 ratio. The solution was filtered and kept in a 100 ml beaker (solution of curcuminoid blended with essential oil of turmeric having 45% Ar-turmerone in 12:1 ratio referred as Solution A). Similarly, weighed quantity of bioavailable curcumin sustained-release composition coated with shellac in 14:1 ratio (Example 16) and bioavailable curcumin sustained-release composition coated with shellac in 10:1 ratio (from example 18) were dissolved in 50 ml of ethanol and filtered to form solution of bioavailable curcumin sustained-release composition coated with shellac in 14:1 ratio and bioavailable curcumin sustained-release composition coated with shellac in 10:1 ratio and is referred as Solution B. Solution A was mixed with Solution B and the mixture was stirred at 500 rpm for 30 min using a mechanical stirrer. The resultant solution was kept in a round bottom flask and solvent was evaporated completely at 50° C. under reduced pressure to get the sustained release product.

Example 22

The curcuminoids blended with essential oil of turmeric having 45% Ar-turmerone in 12:1 ratio prepared (from Example 4) was blended with 500:25 (20:1) ratio of bioavailable curcumin sustained-release composition coated with ethyl cellulose (from example 9) and 10:1 ratio of bioavailable curcumin sustained-release composition coated with ethyl cellulose (from example 6) as shown in Table 18 below to form a bioavailable curcumin sustained release composition. The sustained release composition had 69.27% Curcumin, 15.1% Demethoxy curcumin, 3.5% Bisdemethoxy curcumin, 5.23% essential oil of turmeric having 45% Ar-turmerone, 6.9% ethyl cellulose.

TABLE 18

| S. No. | Ingredients | Quantity (gm) |
|---|---|---|
| 1 | Curcuminoid blended with essential oil of turmeric having 45% Ar-turmerone in 12:1 ratio | 10 |
| 2 | Bioavailable curcumin sustained-release composition coated with ethyl cellulose in 10:1 ratio | 60 |
| 3 | Bioavailable curcumin sustained-release composition coated with ethyl cellulose in 20:1 ratio | 30 |

Weighed quantity of curcuminoid blended with essential oil of turmeric having 45% Ar-turmerone in 12:1 ratio (from Example 4) was dissolved in 50 ml of ethyl acetate by stirring and heating at 50° C. to form solution of curcuminoid blended with essential oil of turmeric having 45% Ar-turmerone in 12:1 ratio. The solution was filtered and kept in a 100 ml beaker (solution of curcuminoid blended with essential oil of turmeric having 45% Ar-turmerone in 12:1 ratio referred as Solution A). Similarly, weighed quantity of bioavailable curcumin sustained-release composition coated with ethyl cellulose in 20:1 ratio (Example 9) and bioavailable curcumin sustained-release composition coated with ethyl cellulose in 10:1 ratio (from example 6) were dissolved in 50 ml of ethanol and filtered to form solution of bioavailable curcumin sustained-release composition coated with ethyl cellulose in 20:1 ratio and bioavailable curcumin sustained-release composition coated with ethyl cellulose in 10:1 ratio and referred as Solution B. Solution A was mixed with Solution B and the mixture was stirred at 500 rpm for 30 min using a mechanical stirrer. The resultant solution was kept in a round bottom flask and solvent was evaporated completely at 50° C. under reduced pressure to get the sustained release product.

Example 23

Dissolution study is a standard method for measuring the rate of drug release from dosage form. The release pattern was tested in simulated gastric fluid up to 2 hours (pH 1.2) and simulated intestinal fluid from 2 to 24 hours (pH 6.8) by in vitro USP dissolution apparatus. The dissolution medium (simulated gastric fluid without enzyme, pH 1.2), free from dissolved air, was filled into the vessel of the dissolution apparatus. Apparatus was assembled and dissolution medium was heated to 36.5° to 37.5°. The capsule containing sustained release formulation was sunk to the bottom of the vessel prior to the rotation of the paddle. A suitable device such as a wire of glass helix was used to keep horizontal at the bottom of the vessel capsules that would otherwise float.

After two hours of operation, an aliquot of the liquid was collected and the dissolution medium was changed to simulated intestinal fluid with pH 6.8 and repeated the above process. Samples were collected at 3, 6, 9, 12, 15, 17, 20, 24 hours.

The samples at each time point were transferred into a liquid-liquid extractor and extracted with ethyl acetate. Acidic and ethyl acetate phases were separated. Ethyl acetate phase was collected and acidic phase was again extracted with ethyl acetate two more times. All the ethyl acetate phases were pooled and extracted with water. Aqueous and ethyl acetate phases were separated and ethyl acetate phase was collected. Ethyl acetate phase was concentrated and dried to form powder of ethyl acetate extract.

The ethyl acetate extract was analyzed by HPLC on a C18 ODS Phenomenox column (250×4.6 mm, 5μ particle size) using 40% tetrahydrofuran (THF), 60% water containing 1% citric acid (pH adjusted to 3 with concentrated KOH solution) as solvent system and UV detection at 420 nm. The eluent flow rate was 1 ml/min. Table 19 shows the percentage of curcuminoid dissolved.

TABLE 19

| | Percentage of curcuminoid dissolved | | | |
|---|---|---|---|---|
| Time | Sustained release formulation coated with ethyl cellulose in 10:1 ratio prepared as per Example 5 | Sustained release formulation coated with ethyl cellulose in 10:1 ratio prepared as per Example 6 | Sustained release formulation coated with Shellac in 10:1 ratio prepared as per Example 17 | Sustained release formulation coated with Shellac in 10:1 ratio prepared as per Example 18 |
| 0 | 0 | 0 | 0 | 0 |
| 2 | 30 | 32 | 35 | 38 |
| 3 | 36 | 43 | 40 | 43 |

TABLE 19-continued

Percentage of curcuminoid dissolved

| Time | Sustained release formulation coated with ethyl cellulose in 10:1 ratio prepared as per Example 5 | Sustained release formulation coated with ethyl cellulose in 10: 1 ratio prepared as per Example 6 | Sustained release formulation coated with Shellac in 10:1 ratio prepared as per Example 17 | Sustained release formulation coated with Shellac in 10:1 ratio prepared as per Example 18 |
|---|---|---|---|---|
| 6  | 42 | 51 | 48 | 50 |
| 9  | 50 | 58 | 57 | 59 |
| 12 | 60 | 66 | 64 | 68 |
| 15 | 75 | 78 | 78 | 80 |
| 17 | 82 | 85 | 86 | 88 |
| 20 | 90 | 93 | 92 | 94 |
| 24 | 98 | 99 | 99 | 99 |

It was found that in first 2 hours only 30-38 percent of the drug was released following the administration of sustained release curcuminoid formulation coated with different coating materials in different ratios. 50-59 percent was released at 9 hours and sequential release was seen up to 24 hours in the dissolution apparatus.

Example 24

The absorption of curcumin after oral administration of sustained release formulations prepared in Example (1, 3, 4, 5, 6, 7, 8, 9 and 10) was studied in healthy human volunteers. Thirty six healthy male volunteers were enrolled for the study. The subjects were fasted overnight before administration of the formulation. Standard meals were provided at 4 hours and 8 hours after dosing and at appropriate times thereafter taking care that the food does not contain turmeric. The subjects were divided into nine groups having four subjects in each group. Subjects of Group 1 received a single dose (2 gm) of regular turmeric extract (Example 1). Subjects of Group 2 received a single dose (2 gm) of curcuminoids blended with essential oil of turmeric having 45% Ar-turmerone in 10:1 ratio (Example 3). Subjects of Group 3 received a single dose (2 gm) of curcuminoids blended with essential oil of turmeric having 45% Ar-turmerone in 12:1 ratio (Example 4). Subjects of Group 4 received a single dose (2 gm) of sustained release formulation of regular turmeric extract (Example 7). Whereas Group 5 and 6 received a single dose (2 gm) of sustained release formulation coated with ethyl cellulose in 10:1 ratio (Example 5) (curcuminoid blended with essential oil of turmeric having 45% Ar-turmerone in 10:1 ratio) and sustained release formulation coated with ethyl cellulose in 10:1 ratio (Example 6) (curcuminoids blended with essential oil of turmeric having 45% Ar-turmerone in 12:1 ratio) respectively. Subjects of Group 7 received a single dose (2 gm) of sustained release formulation of regular turmeric extract coated with ethyl cellulose in 500:25 (20:1) ratio (Example 10). Whereas Group 8 and 9 received a single dose (2 gm) of sustained release formulation coated with ethyl cellulose in 500:25 ratio (Example 8) (curcuminoid blended with essential oil of turmeric having 45% Ar-turmerone in 10:1) and sustained release formulation coated with ethyl cellulose in 500:25 ratio (Example 9) (curcuminoids blended with essential oil of turmeric having 45% Ar-turmerone in 12:1 ratio) respectively with 250 ml of water at ambient temperature after the overnight fast.

Blood was collected at different time intervals at baseline, 1, 2, 4, 6, 8, 12, 24, 27 and 30 hours post drug. The whole blood was extracted exhaustively with ethyl acetate to recover curcumin. The ethyl acetate extract was analyzed by HPLC on a RP-C18 column (250×4 5 mm) using tetrahydrofuran (THF) as solvent and UV detection at 420 nm. The eluant flow rate was 1 ml/min. The blood level concentration of curcumin, DMC (Demethoxy curcumin) and BDMC (Bis-Demethoxy curcumin) was determined by HPLC against working standards for samples collected at different time points and averaged over the four volunteers. The data is given in FIG. 26 Table 20(a) and FIG. 27 Table 20(b). The blood concentration of curcuminoids versus time profile is illustrated in FIG. 1-6.

Results show that curcumin was detected in subjects of all the groups. The curcumin was detected only up to 6 hr in the subjects treated with Regular turmeric extract (Example 1). The Cmax was 14.5 ng/gm in the group fed only Regular turmeric extract (Group I). The subjects treated with curcuminoids blended with essential oil of turmeric having 45% Ar-turmerone in 10:1 ratio (Example 3) had average blood curcumin level significantly higher (Cmax=80.3 ng/gm) than the subjects treated with Regular turmeric extract (Example 1). The subjects treated with curcuminoids blended with essential oil of turmeric having 45% Ar-turmerone in 12:1 ratio (Example 4) showed slightly higher curcumin level (Cmax=102.1 ng/gm) than the subjects treated with formulation prepared in Example 3. These results indicate that combining essential oil of turmeric with regular turmeric extract increases the blood concentration of curcumin to significant level. Moreover, blending of essential oil of turmeric to the regular turmeric extract increased the detection of curcumin up to 8 hr.

Sustained release formulations developed with regular turmeric extract (Example 7 and Example 10) did not show any significant increase in blood concentration of curcumin, and, curcumin was detected only up to 6 hr.

The subjects treated with sustained release formulation of curcuminoid blended with essential oil of turmeric having 45% Ar-turmerone in 10:1 ratio coated with ethyl cellulose (Example 5 and Example 8) showed high curcumin level in the blood. Cmax was 133.4 and 138.1 ng/gm respectively for subjects treated with formulation prepared in Example 5 and Example 8 respectively. Curcumin was also detected up to 30 hr in the blood.

Similarly, the subjects treated with sustained release formulation of curcuminoid blended with essential oil of turmeric having 45% Ar-turmerone in 12:1 ratio coated with ethyl cellulose (Example 6 and Example 9) also showed high curcumin level in the blood. Cmax was 162.5 and 158.5 ng/gm respectively for subjects treated with formulation prepared in Example 6 and Example 9 respectively. Curcumin was also detected up to 30 hr in the blood.

These results suggest that the sustained release formulation need be given only once daily and it will last at least up to 30 hr at significant level required to produce pharmacological effect.

Demethoxy curcumin (DMC) was not detected in the subjects treated with formulations prepared in Example 1, 7 and 10. It was detected in the subjects treated with formulations prepared in Example 5, 6, 8 and 9. DMC was detected up to 27 hr in the subjects treated with ethyl cellulose coated sustained release formulation of curcuminoid blended with essential oil of turmeric having 45% Ar-turmerone in 10:1 ratio (Example 5 and Example 8). DMC was detected up to 30 hr in the subjects treated with ethyl cellulose coated sustained release formulation of curcuminoid blended with essential oil of turmeric having 45%

Ar-turmerone in 12:1 ratio (Example 6 and Example 9). This further indicates the superiority of sustained release formulations.

Bisdemethoxy curcumin (BDMC) was not detected in the subjects treated with formulations prepared in Example 1, 7 and 10. It was detected in the subjects treated with formulations prepared in Example 5, 6, 8 and 9. BDMC was detected up to 24 hr in the subjects treated with ethyl cellulose coated sustained release formulation of curcuminoid blended with essential oil of turmeric having 45% Ar-turmerone in 10:1 ratio (Example 5 and Example 8) and in subjects treated with ethyl cellulose coated sustained release formulation of curcuminoid blended with essential oil of turmeric having 45% Ar-turmerone in 12:1 ratio (Example 6 and Example 9). This also indicates the superiority of sustained release formulations.

Blending essential oil of turmeric with regular turmeric extract increased the blood concentration of curcumin to significant levels. For example, at 4 hours following administration of the formulations, 10.2 ng/g curcumin was detected in the blood when regular turmeric extract was administered. 80.3 ng/g of curcumin was detected when administered with curcuminoids blended with essential oil of turmeric having 45% Ar-turmerone in 10:1 ratio (Example 3). 102.1 ng/g of curcumin was detected when administered with curcuminoids blended with essential oil of turmeric having 45% Ar-turmerone in 12:1 ratio (Example 4). In case of sustained release formulations at 4 hr 133.4 ng/g curcumin was detected when ethyl cellulose coated sustained release formulation of curcuminoid blended with essential oil of turmeric having 45% Ar-turmerone in 10:1 ratio (Example 5) was administered. 162.5 ng/g curcumin was detected when ethyl cellulose coated sustained release formulation of curcuminoid blended with essential oil of turmeric having 45% Ar-turmerone in 12:1 ratio (Example 6).

Only 14.4 ng/g curcumin was detected when ethyl cellulose coated Sustained release formulation of regular turmeric extract (Example 7) was administered. Moreover, Sustained release formulations prepared with curcuminoids blended with essential oil of turmeric having 45% Ar-turmerone in 10:1 or 12:1 ratio provided higher blood concentration of curcumin, demethoxy curcumin and bisdemethoxy curcumin. Sustained release curcuminoid formulations also provided significant concentration of curcumin, DMC and BDMC up to more than 24 hour. Thus a single dose of sustained release curcuminoid formulation a day was sufficient to obtain higher levels curcumin, DMC and BDMC in the blood.

Example 25

The absorption of curcumin after oral administration of sustained release formulations prepared in Example (1, 3, 4, 15, 16, 17, 18, 19 and 20) was studied in healthy human volunteers. Thirty six healthy male volunteers were enrolled for the study. The subjects were fasted overnight before administration of the formulation. Standard meals were provided at 4 hours and 8 hours after dosing and at appropriate times thereafter taking care that the food does not contain turmeric. The subjects were divided into nine groups having four subjects in each group. Subjects of Group 1 received a single dose (2 gm) of regular turmeric extract (Example 1). Subjects of Group 2 received a single dose (2 gm) of curcuminoids blended with essential oil of turmeric having 45% Ar-turmerone in 10:1 ratio (Example 3). Subjects of Group 3 received a single dose (2 gm) of curcuminoids blended with essential oil of turmeric having 45% Ar-turmerone in 12:1 ratio (Example 4). Subjects of Group 4 received a single dose (2 gm) of sustained release formulation of regular turmeric extract coated with shellac in 14:1 ratio (Example 19). Subjects of Group 5 and 6 received a single dose (2 gm) of sustained release formulation coated with shellac in 14:1 ratio prepared as per Example 15 (curcuminoid blended with essential oil of turmeric having 45% Ar-turmerone in 10:1 ratio) and sustained release formulation coated with shellac prepared in 14:1 ratio prepared as per Example 16 (curcuminoid blended with essential oil of turmeric having 45% Ar-turmerone in 12:1 ratio). Whereas Group 7 and 8 received a single dose (2 gm) of sustained release formulation coated with shellac in 10:1 ratio prepared as per Example 17 (curcuminoid blended with essential oil of turmeric having 45% Ar-turmerone in 10:1 ratio) and sustained release formulation coated with shellac in 10:1 ratio prepared as per Example 18 (curcuminoid blended with essential oil of turmeric having 45% Ar-turmerone in 12:1 ratio) respectively. Subjects of Group 9 received a single dose (2 gm) of sustained release formulation of regular turmeric extract coated with shellac in 10:1 ratio (Example 20) with 250 ml of water at ambient temperature after the overnight fast.

Blood was collected at different time intervals at baseline, 1, 2, 4, 6, 8, 12, 24, 27 and 30 hours post drug. The whole blood was extracted exhaustively with ethyl acetate to recover curcumin. The ethyl acetate extract was analyzed by HPLC on a RP-C18 column (250×4 5 mm) using tetrahydrofuran (THF) as solvent and UV detection at 420 nm. The eluant flow rate was 1 ml/min. The blood level concentration of curcumin, DMC (Demethoxy curcumin) and BDMC (Bis-Demethoxy curcumin) was determined by HPLC against working standards for samples collected at different time points and averaged over the four volunteers. The data is given in FIG. 28 Table 21(a) and FIG. 29 Table 21 (b). The blood concentration of curcuminoids versus time profile is illustrated in FIG. 7-12. Results show that curcumin was detected in subjects of all the groups. The curcumin was detected only up to 4 hr in the subjects treated with Regular turmeric extract (Example 1). The Cmax was 13.1 ng/gm in the group fed only Regular turmeric extract (Group I). The subjects treated with curcuminoids blended with essential oil of turmeric having 45% Ar-turmerone in 10:1 ratio (Example 3) had average blood curcumin level significantly higher (Cmax=89.6 ng/gm) than the subjects treated with Regular turmeric extract (Example 1). The subjects treated with curcuminoids blended with essential oil of turmeric having 45% Ar-turmerone in 12:1 ratio (Example 4) has shown slightly higher curcumin level (Cmax=110.2 ng/gm) than the subjects treated with formulation prepared in Example 3. These results indicate that combining essential oil of turmeric with regular turmeric extract increases the blood concentration of curcumin to significant level. Moreover, blending of essential oil of turmeric to the regular turmeric extract increased the detection of curcumin up to 8 hr.

Sustained release formulations developed with regular turmeric extract (Example 19 and Example 20) did not show any significant increase in blood concentration of curcumin, and, curcumin was detected only up to 4 hr.

The subjects treated with shellac coated sustained release formulation of curcuminoid blended with essential oil of turmeric having 45% Ar-turmerone in 10:1 ratio (Example 15 and Example 17) showed high curcumin level in the blood. Cmax was 142.1 and 132.4 ng/gm respectively for subjects treated with formulation prepared in Example 17 and Example 15 respectively. Curcumin was also detected up to 30 hr in the blood.

Similarly, the subjects treated with shellac coated sustained release formulation of curcuminoid blended with essential oil of turmeric having 45% Ar-turmerone in 12:1 ratio (Example 16 and Example 18) also showed high curcumin level in the blood. Cmax was 169.8 and 159.4 ng/gm respectively for subjects treated with formulation prepared in Example 18 and Example 16 respectively. Curcumin was also detected up to 30 hr in the blood.

These results suggest that once daily administration of sustained release curcuminoid formulation provides curcumin, demethoxy curcumin and bisdemethoxy curcumin for at least up to 30 hr, and, at significant levels required to produce pharmacological effects.

Demethoxy curcumin (DMC) was not detected in the subjects treated with formulations prepared in Example 1, 19 and 20. It was detected in the subjects treated with formulations prepared in Example 15, 16, 17 and 18. DMC was detected up to 27 hr in the subjects treated with shellac coated sustained release formulation of curcuminoid blended with essential oil of turmeric having 45% Ar-turmerone in 10:1 ratio (Example 15 and Example 17). DMC was detected up to 30 hr in the subjects treated with shellac coated sustained release formulation of curcuminoid blended with essential oil of turmeric having 45% Ar-turmerone in 12:1 ratio (Example 16 and Example 18). This further indicates the superiority of sustained release formulations.

Bisdemethoxy curcumin (BDMC) was not detected in the subjects treated with formulations prepared in Example 1, 19 and 20. It was detected in the subjects treated with formulations prepared in Example 15, 16, 17 and 18. BDMC was detected up to 24 hr in the subjects treated with shellac coated sustained release formulation of curcuminoid blended with essential oil of turmeric having 45% Ar-turmerone in 10:1 ratio (Example 15 and Example 17) and in subjects treated with shellac coated sustained release formulation of curcuminoid blended with essential oil of turmeric having 45% Ar-turmerone in 12:1 ratio (Example 16 and Example 18). This also indicates the superiority of sustained release formulations.

Blending essential oil of turmeric with regular turmeric extract increased the blood concentration of curcumin to significant levels. For example, at 4 hours following administration of the formulations, 9.4 ng/g curcumin was detected in the blood when regular turmeric extract was administered. 89.6 ng/g of curcumin was detected when administered with curcuminoids blended with essential oil of turmeric having 45% Ar-turmerone in 10:1 ratio (Example 3). 110.2 ng/g of curcumin was detected when administered with curcuminoids blended with essential oil of turmeric having 45% Ar-turmerone in 12:1 ratio (Example 4). In case of shellac coated sustained release formulations at 4 hr 142.1 ng/g curcumin was detected when shellac coated sustained release formulation of curcuminoid blended with essential oil of turmeric having 45% Ar-turmerone in 10:1 ratio (Example 17) was administered. 169.8 ng/g curcumin was detected when shellac sustained release formulation of curcuminoid blended with essential oil of turmeric having 45% Ar-turmerone in 12:1 ratio (Example 18). Only 14.2 ng/g curcumin was detected when shellac coated Sustained release formulation of regular turmeric extract (Example 19) was administered. Moreover, shellac coated Sustained release formulations prepared with curcuminoids blended with essential oil of turmeric having 45% Ar-turmerone in 10:1 or 12:1 ratio provided higher blood concentration of curcumin, demethoxy curcumin and bisdemethoxy curcumin. Shellac coated Sustained release formulations also provided significant concentration of curcumin, DMC and BDMC up to more than 24 hour. Thus only once daily dose of sustained release formulation was sufficient to obtain higher levels curcumin, DMC and BDMC in the blood.

Example 26

Twenty eight healthy male volunteers were enrolled for the study. The subjects were fasted overnight before administration of the formulation. Standard meals were provided at 4 hours and 8 hours after dosing and at appropriate times thereafter taking care that the food does not contain turmeric. The subjects (random no's R 101 to R 128) were divided into seven groups having four subjects in each group. Subjects of Group 1 (R 101 to 104) received a single dose (2 gm) of regular turmeric extract (RTE) (study drug I prepared as per Example 1) and Subjects of Group 2 (R 105 to 108) received a single dose (2 gm) of ethyl cellulose coated sustained release formulation of regular turmeric extract (EC coated RTE) (study drug II prepared as per Example 7). Subjects of Group 3 (R 109 to 112) received a single dose (2 gm) of ethyl cellulose coated sustained release formulation of curcuminoids blended with essential oil of turmeric having 45% Ar-turmerone in 12:1 ratio (EC coated SR formulation) (study drug III prepared as per Example 6). Subjects of Group 4 (R 113 to 116) received a single dose (2 gm) of shellac coated sustained release formulation of regular turmeric extract (S coated RTE) (study drug IV prepared as per Example 20). Subjects of Group 5 (R 117 to 120) received a single dose (2 gm) of shellac coated sustained release formulation of curcuminoid blended with essential oil of turmeric having 45% Ar-turmerone in 12:1 ratio (S coated SR formulation) (study drug V prepared as per Example 18). Subjects of Group 6 (R 121 to 124) received a single dose (2 gm) of curcuminoid blended with essential oil of turmeric having 45% Ar-turmerone in 10:1 ratio (C+EOT with 45% Ar-t in 10:1 ratio) (study drug VI prepared as per Example 3) and subjects of Group 7 (R 125 to 128) received a single dose (2 gm) of curcuminoid blended with essential oil of turmeric having 45% Ar-turmerone in 12:1 ratio (C+EOT with 45% Ar-t in 12:1 ratio) (study drug VII prepared as per Example 4) with 250 ml of water at ambient temperature after the overnight fast. Blood was collected at different time intervals at baseline, 0.5, 1, 2, 3, 4, 6, 8, 10, 12, 16, 20, 24, 28, 32 and 36 hours post drug. After wash out period of two weeks the subjects were crossed-over to the other drug as given below table 22(FIG. 30).

Blood was collected at different time intervals at baseline, 0.5, 1, 2, 3, 4, 6, 8, 10, 12, 16, 20, 24, 28, 32 and 36 hours post drug. The whole blood was extracted exhaustively with ethyl acetate to recover curcumin. The ethyl acetate extract was analyzed by HPLC on a RP-C18 column (250×4 5 mm) using tetrahydrofuran (THF) as solvent and UV detection at 420 nm. The eluant flow rate was 1 ml/min. The blood level concentration of curcumin, DMC (Demethoxy curcumin) and BDMC (Bis-Demethoxy curcumin) was determined by HPLC against working standards for samples collected at different time points and averaged over the four volunteers. The data is given in Table 23(a)(FIG. 31) and Table 23 (b) (FIG. 32). The blood concentration of curcuminoids versus time profile is illustrated in FIG. 16-21.

Results show that half life ($t_{1/2}$) of sustained release formulation was increased. In sustained release curcuminoid formulation prepared as per example 6, following the administration of the composition results a half life of 7.5, 6.9 and 5.97 hours for curcumin, demethoxy curcumin and bis-Demethoxy curcumin respectively. Whereas for curcuminoids blended with essential oil of turmeric with 45% Ar-turmerone in 10:1 and 12:1 ratios results a half life of curcumin 4.6 and 4.9 hours respectively. In sustained release curcuminoid formulation prepared as per example 18, following the administration of the composition results a half life of 8.2, 7.4 and 5.89 hours for curcumin, demethoxy curcumin and bis-Demethoxy curcumin respectively.

Higher $t_{1/2}$ indicates the longer stay of the curcuminoids in the formulation in the body. Area under the curve (AUC0-t) of curcumin, demethoxy curcumin and bisdemethoxy curcumin in sustained release groups were calculated from the respective graphs, which showed that the AUC was increased. In sustained release curcuminoid formulation prepared as per example 6, following the administration of the composition results an AUC of 2508.2, 1517.9 and 322.6 ng/gm for curcumin, demethoxy curcumin and bis-Demethoxy curcumin respectively. Whereas after administration of curcuminoids blended with essential oil of turmeric with 45% Ar-turmerone in 10:1 and 12:1 ratios results a AUC of curcumin 333.3 and 421.1 ng/gm respectively. In sustained release curcuminoid formulation prepared as per example 18, following the administration of the composition results a AUC of 2653.4, 1560.7 and 330.8 ng/gm for curcumin, demethoxy curcumin and bis-Demethoxy curcumin respectively.

Figure 24:
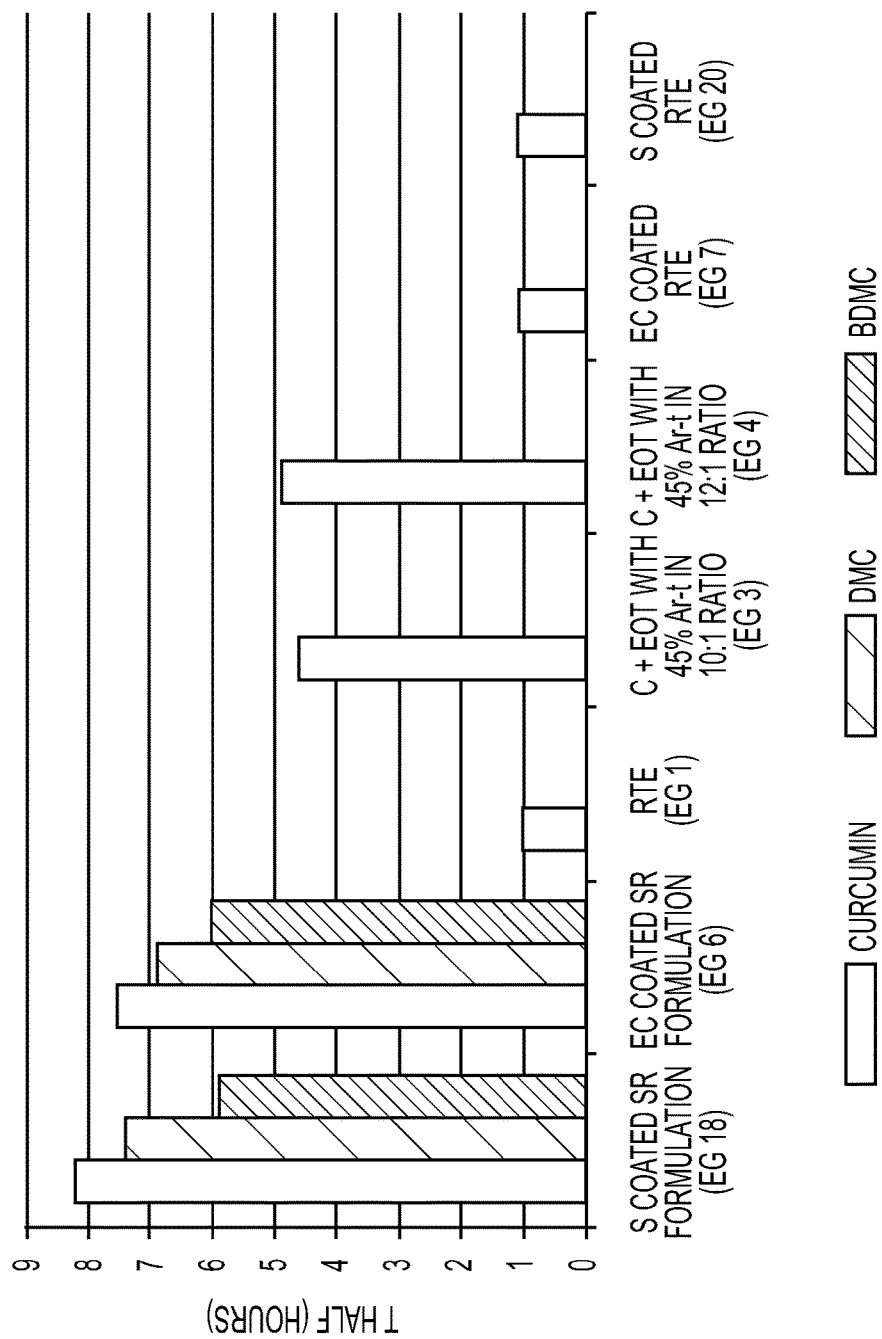
FIG. 24 provides a graph showing T half (Hours) of Sustained release groups, regular turmeric extract and curcuminoids blended with essential oil of turmeric in 10:1 and 12:1 ratios as per example 26.
Figure 25:
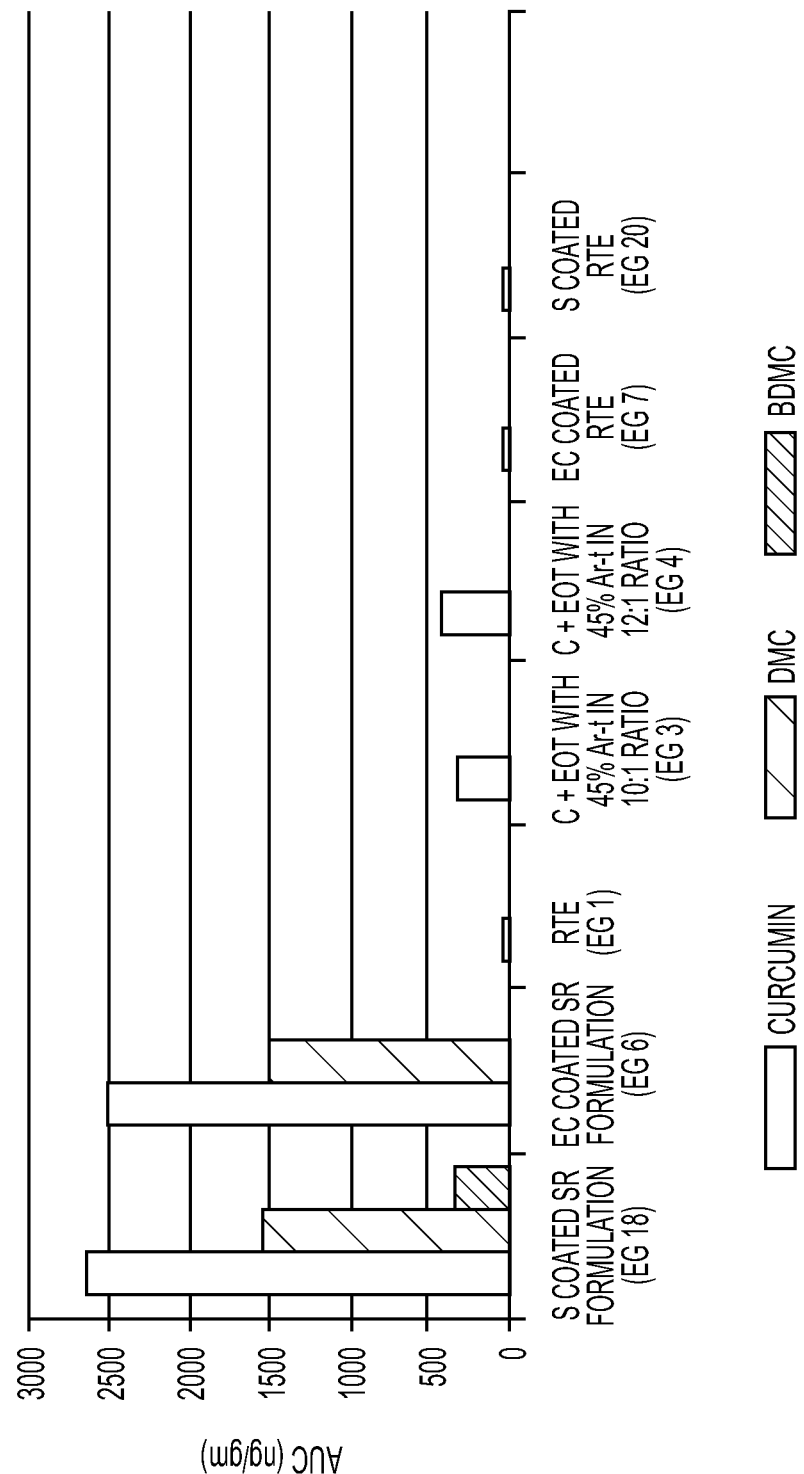
FIG. 25 provides a graph showing AUC (ng/gm) of Sustained release groups, regular turmeric extract and curcuminoids blended with essential oil of turmeric in 10:1 and 12:1 ratios as per example 26.

The half life and Area under the curve (AUC0-t) of sustained release formulation, regular turmeric extract and curcuminoids blended with essential oil of turmeric in 10:1 and 12:1 ratios are illustrated in FIGS. 24 and 25 respectively.

Example 27

The absorption of curcumin after oral administration of sustained release formulations prepared in Example 21 and 22 was studied in healthy human volunteers. Twenty five healthy male volunteers were enrolled for the study. The subjects were fasted overnight before administration of the formulation. Standard meals were provided at 4 hours and 8 hours after dosing and at appropriate times thereafter taking care that the food does not contain turmeric. The subjects were divided into five groups having five subjects in each group. Subjects of Group 1 received a single dose (2 gm) of regular turmeric extract (RTE) (Example 1). Subjects of Group 2 received a single dose (2 gm) of sustained release formulation (S coated SR formulation) prepared as per Example 21 and subjects of Group 3 received a single dose (2 gm) of sustained release formulation (EC coated SR formulation) prepared as per Example 22. Subjects of Group 4 received a single dose (2 gm) of curcuminoids blended with essential oil of turmeric in 10:1 ratio (C+EOT with 45% Ar-t in 10:1 ratio) prepared as per Example 3 and subjects of Group 5 received a single dose (2 gm) of curcuminoids blended with essential oil of turmeric in 12:1 ratio (C+EOT with 45% Ar-t in 12:1 ratio) prepared as per Example 4 with 250 ml of water at ambient temperature after the overnight fast.

Figure 13:
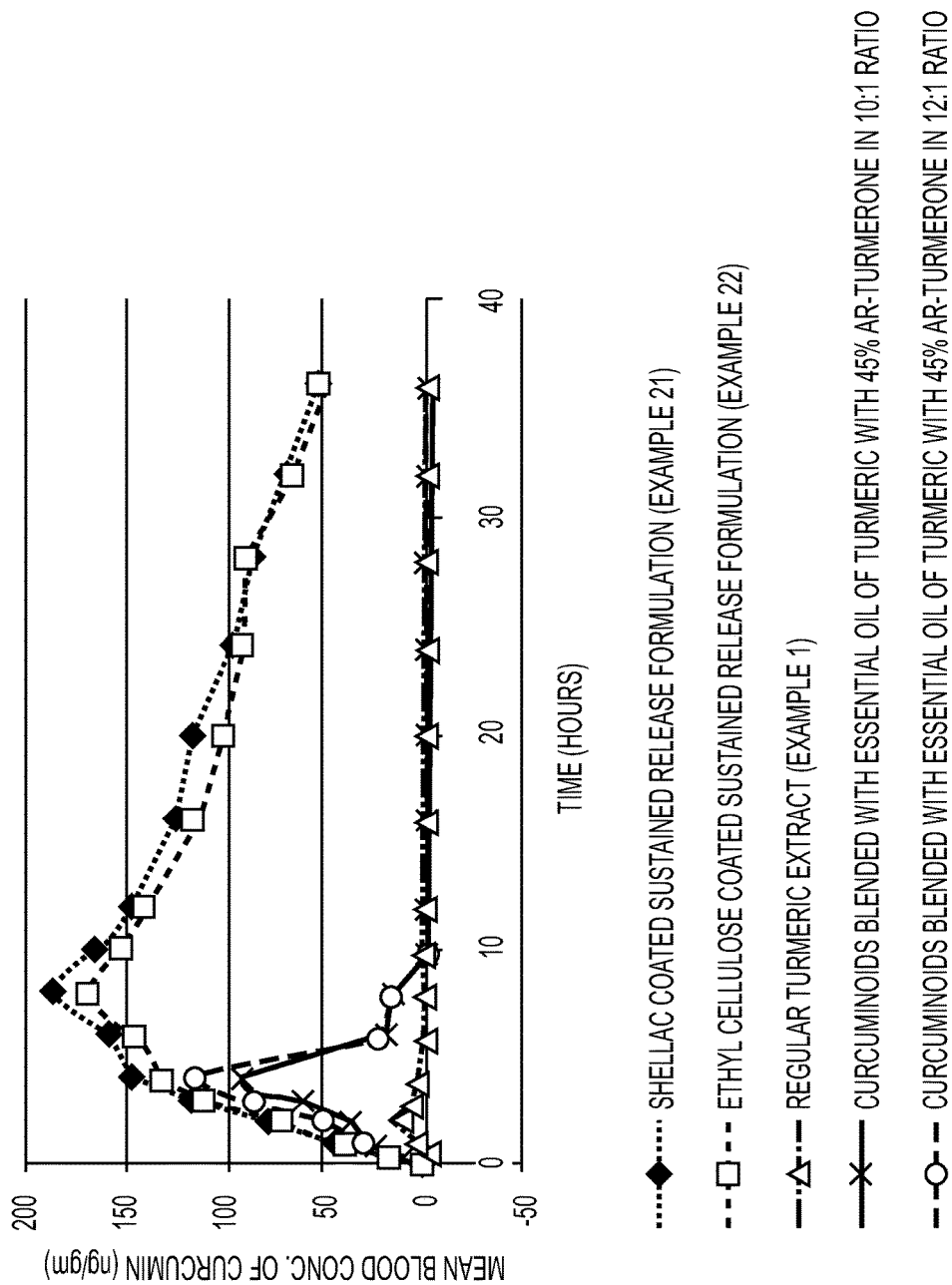
FIG. 13 provides a graph showing in human subjects mean blood concentration of curcumin (ng/gm) Vs Time after administering a bioavailable curcumin formulation and shellac coated sustained release curcuminoid formulation and ethyl cellulose coated sustained release curcuminoid formulation in different ratios.
Figure 14:
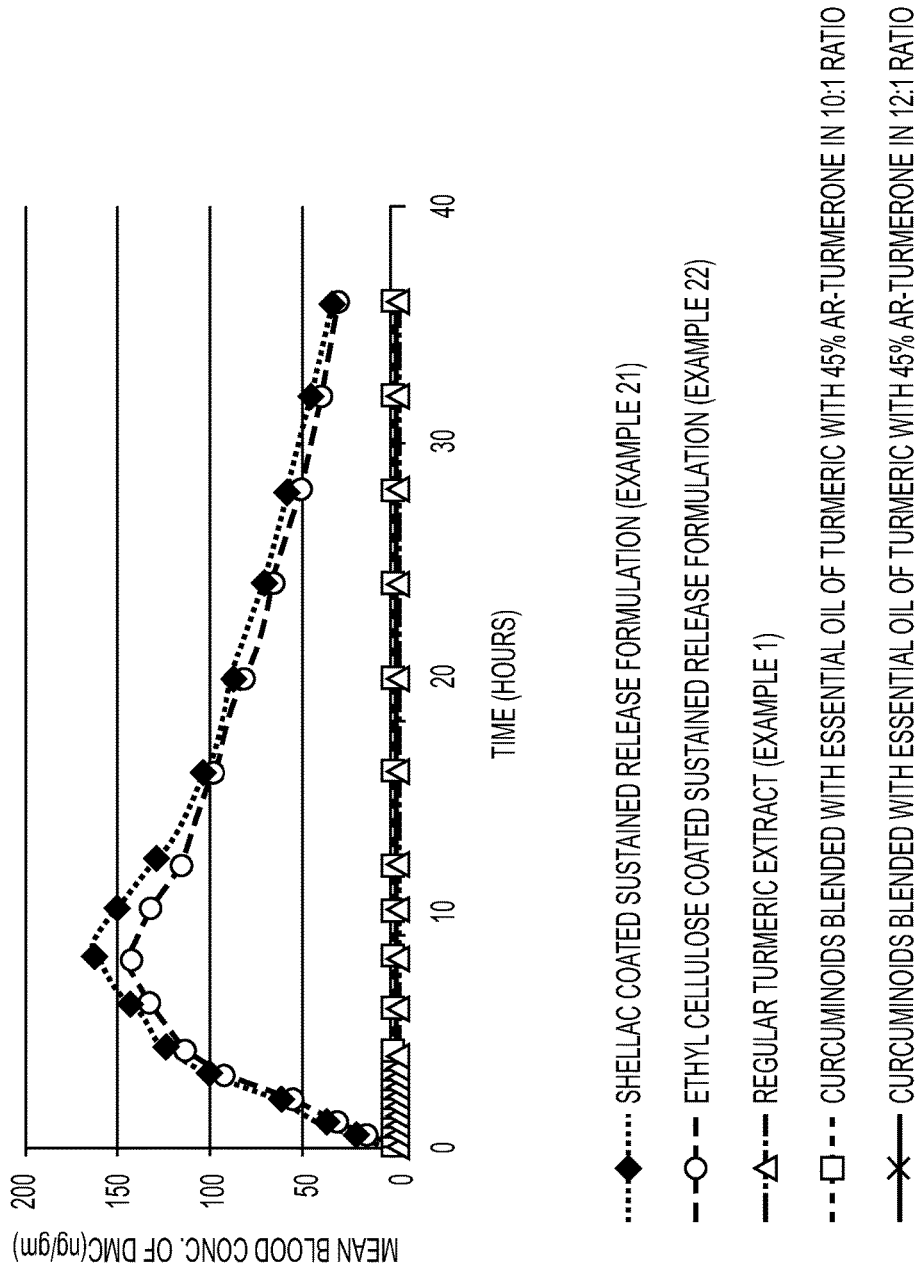
FIG. 14 provides a graph showing in human subjects the mean blood concentration of demethoxy curcumin (DMC) (ng/gm) Vs Time after administering a formulation contain bioavailable curcumin formulation and shellac coated sustained curcuminoid release formulation and ethyl cellulose coated sustained release curcuminoid formulation in different ratios.
Figure 15:
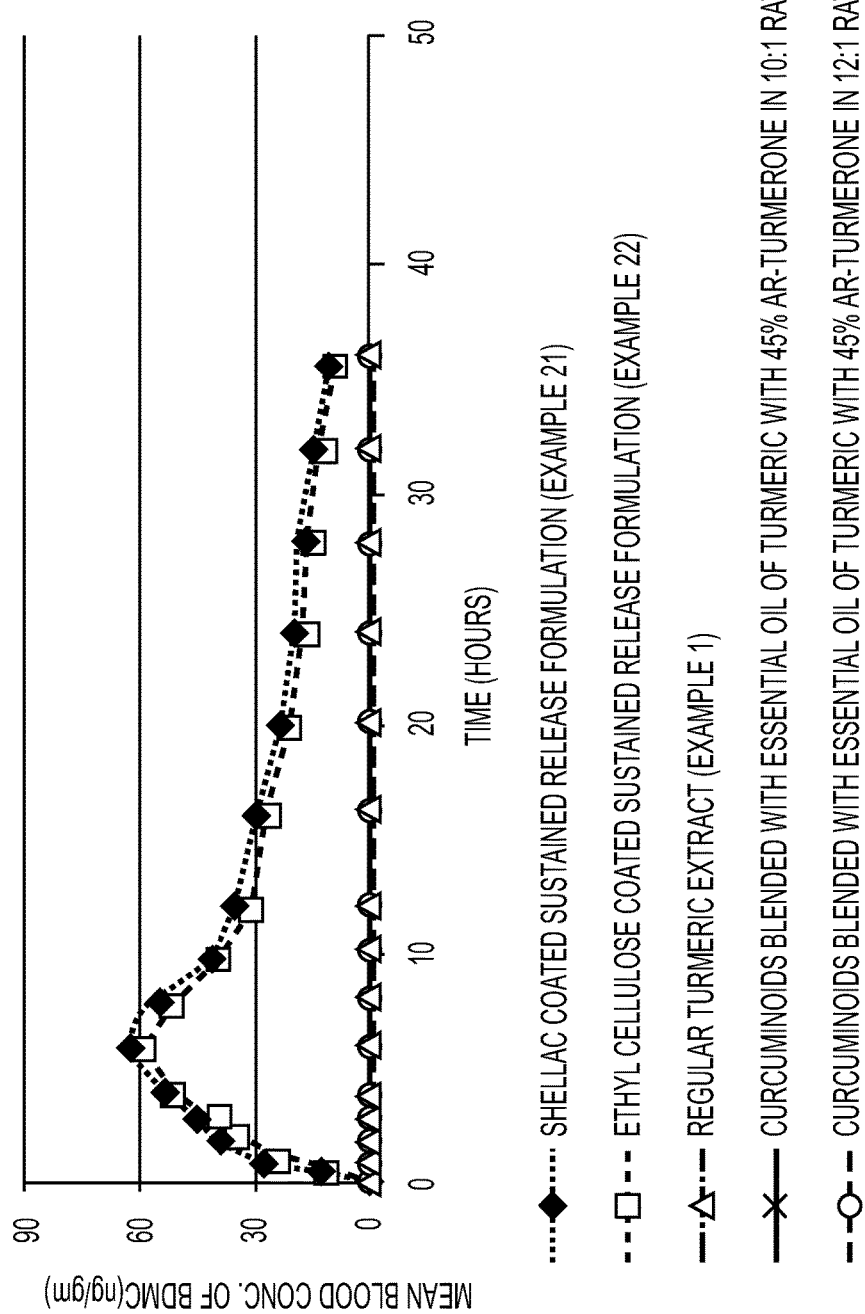
FIG. 15 provides a graph showing in human subjects, the mean blood concentration of bis demethoxy curcumin (BDMC) (ng/gm) Vs Time after administering a formulation containing a bioavailable curcumin formulation and shellac coated sustained release curcuminoid formulation and ethyl cellulose coated sustained release curcuminoid formulation in different ratios.
Figure 16:
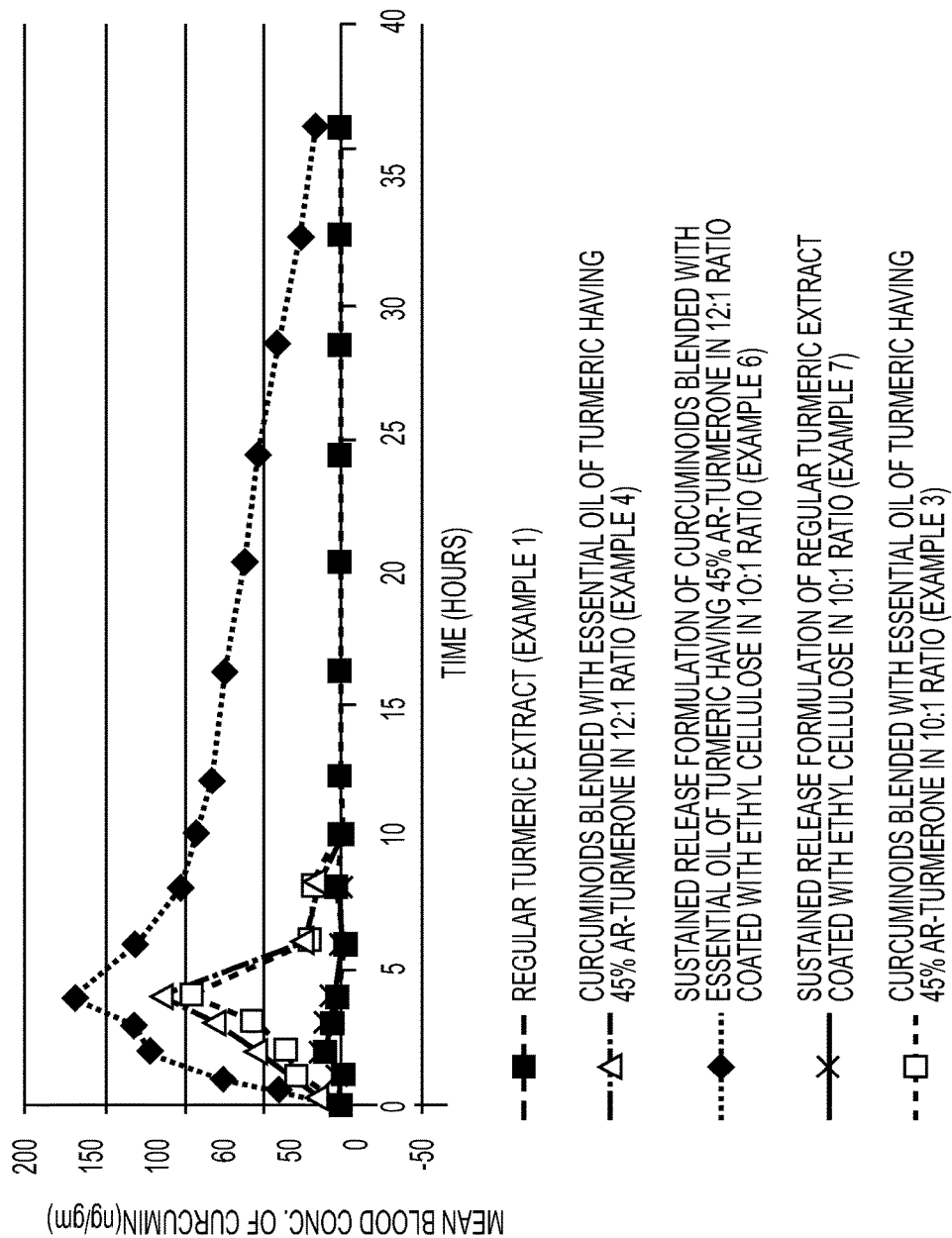
FIG. 16 provides a graph showing Mean blood concentration of curcumin (ng/gm) Vs Time after administering in human subjects a sustained release curcuminoid formulation coated with ethyl cellulose in 10:1 ratio (example 26 Table 23 a).
Figure 17:
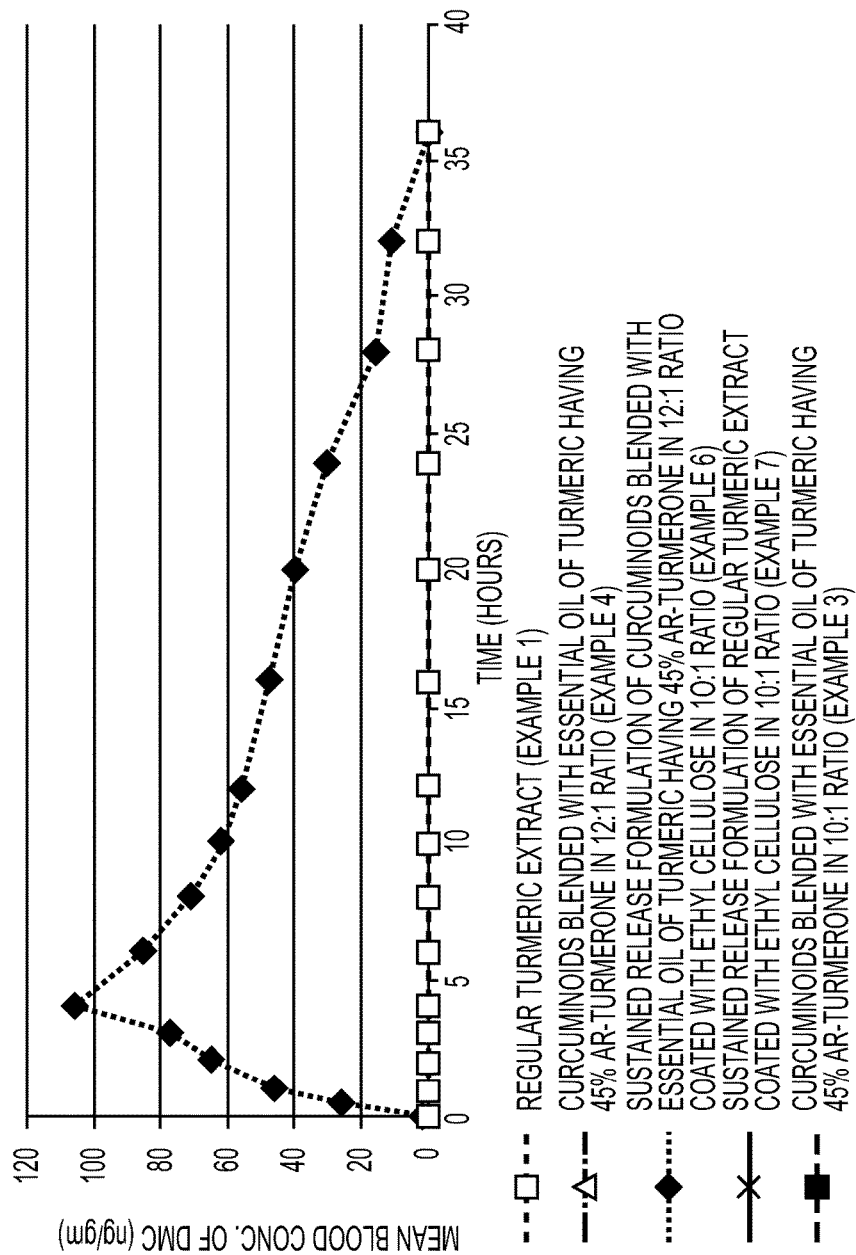
FIG. 17 provides a graph showing Mean blood concentration of DMC (ng/gm) Vs Time after administering in human subjects sustained release curcuminoid formulation coated with ethyl cellulose in 10:1 ratio (example 26 Table 23 a).
Figure 18:
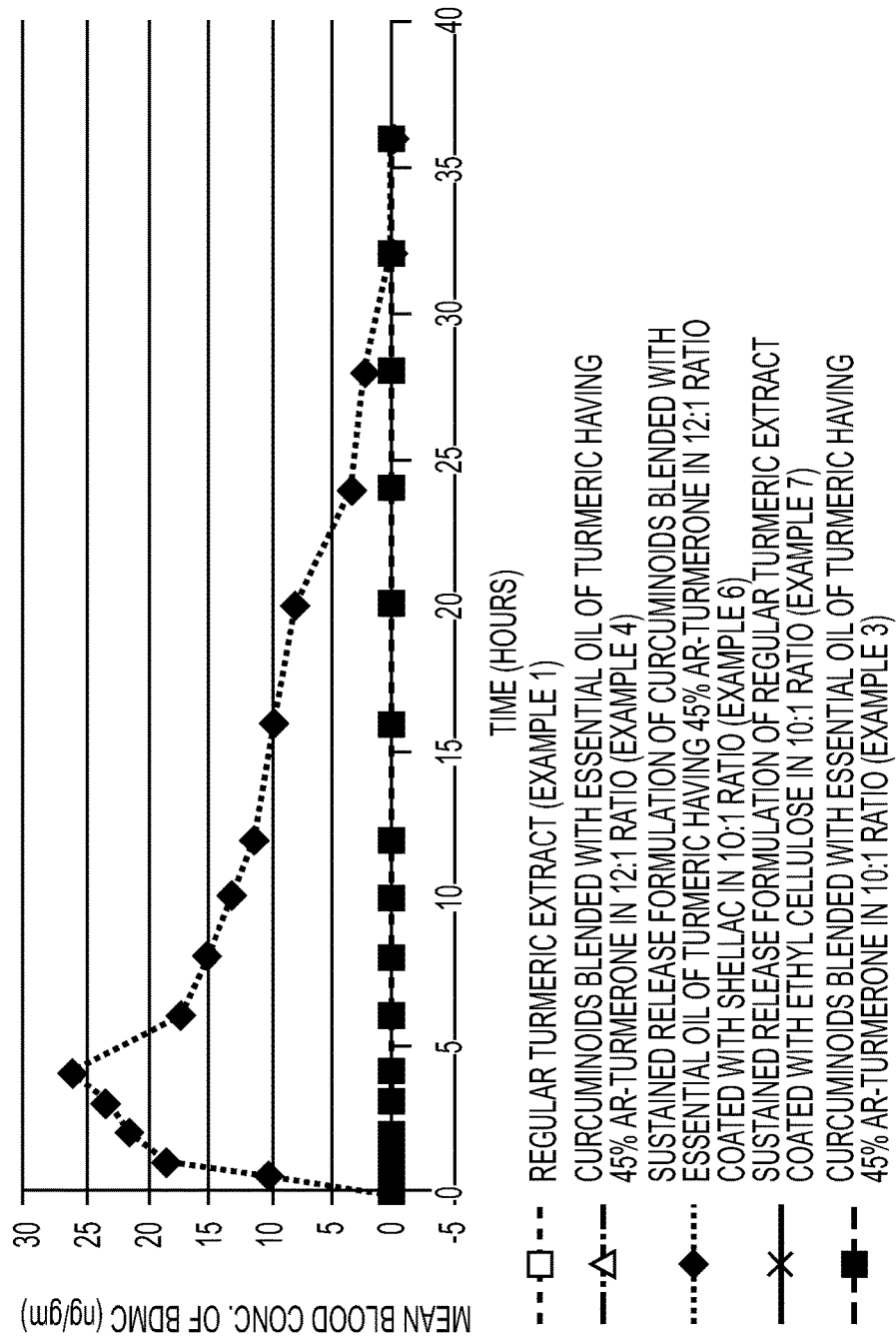
FIG. 18 provides a graph showing Mean blood concentration of BDMC (ng/gm) Vs Time after administering human subjects a sustained release curcuminoid formulation coated with ethyl cellulose in 10:1 ratio (example 26 Table 23 a).
Figure 19:
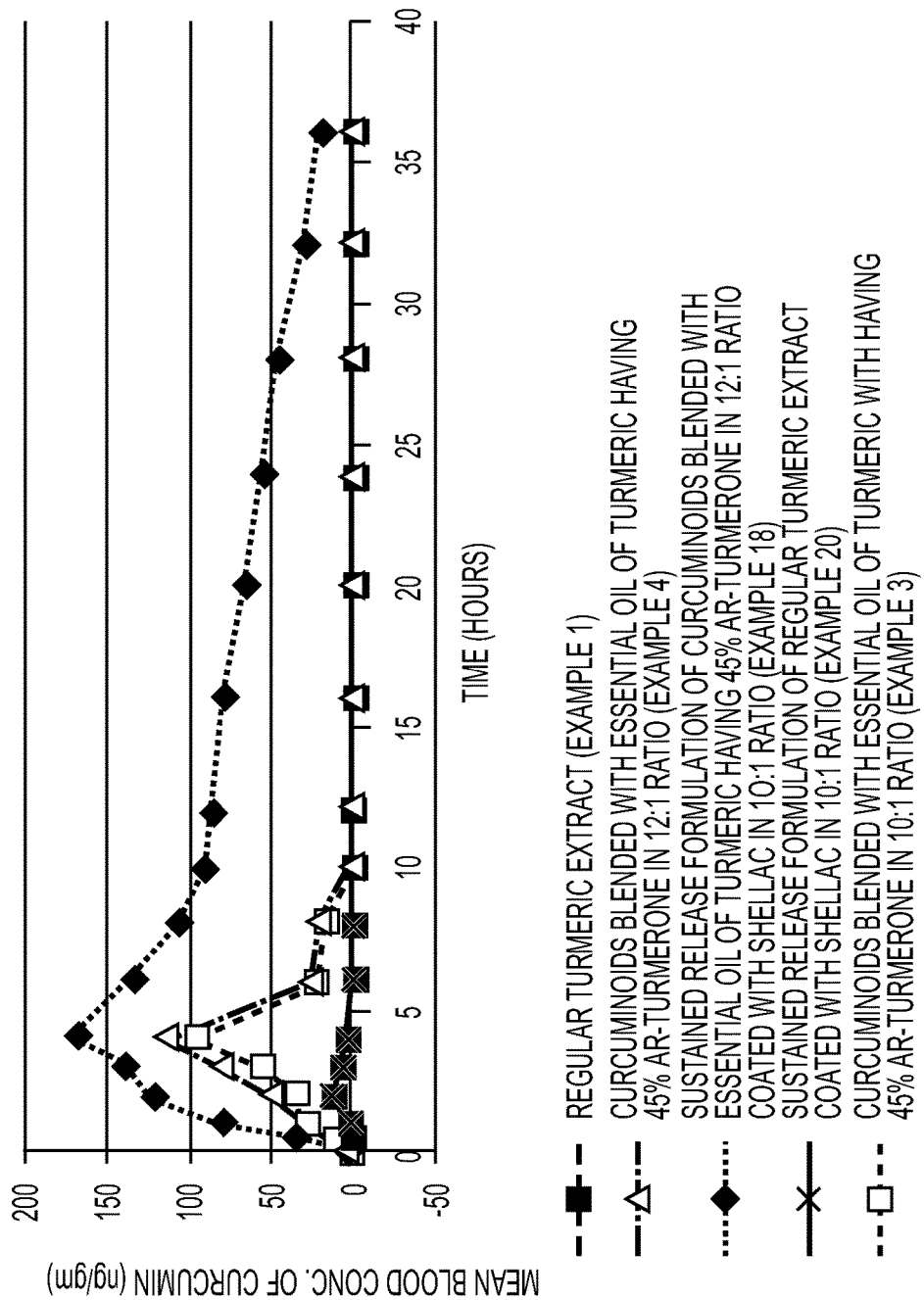
FIG. 19 provides a graph showing Mean blood concentration of curcumin (ng/gm) Vs Time after administering human subjects a sustained release curcuminoid formulation coated with shellac in 10:1 ratio (example 26 Table 23 b).
Figure 20:
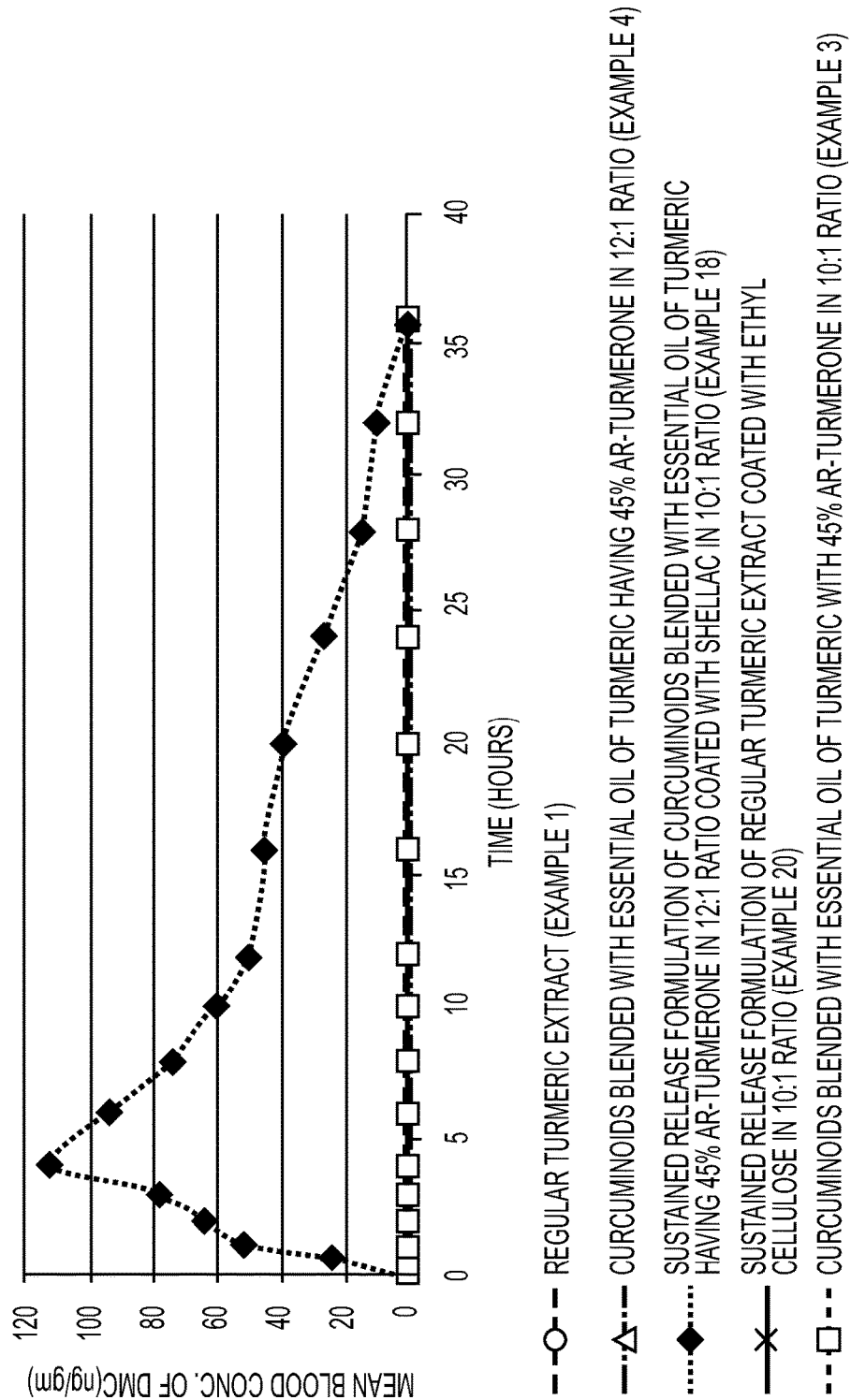
FIG. 20 provides a graph showing Mean blood concentration of DMC (ng/gm) Vs Time after administering human subjects a sustained release curcuminoid formulation coated with shellac in 10:1 ratio (example 26 Table 23 b).
Figure 21:
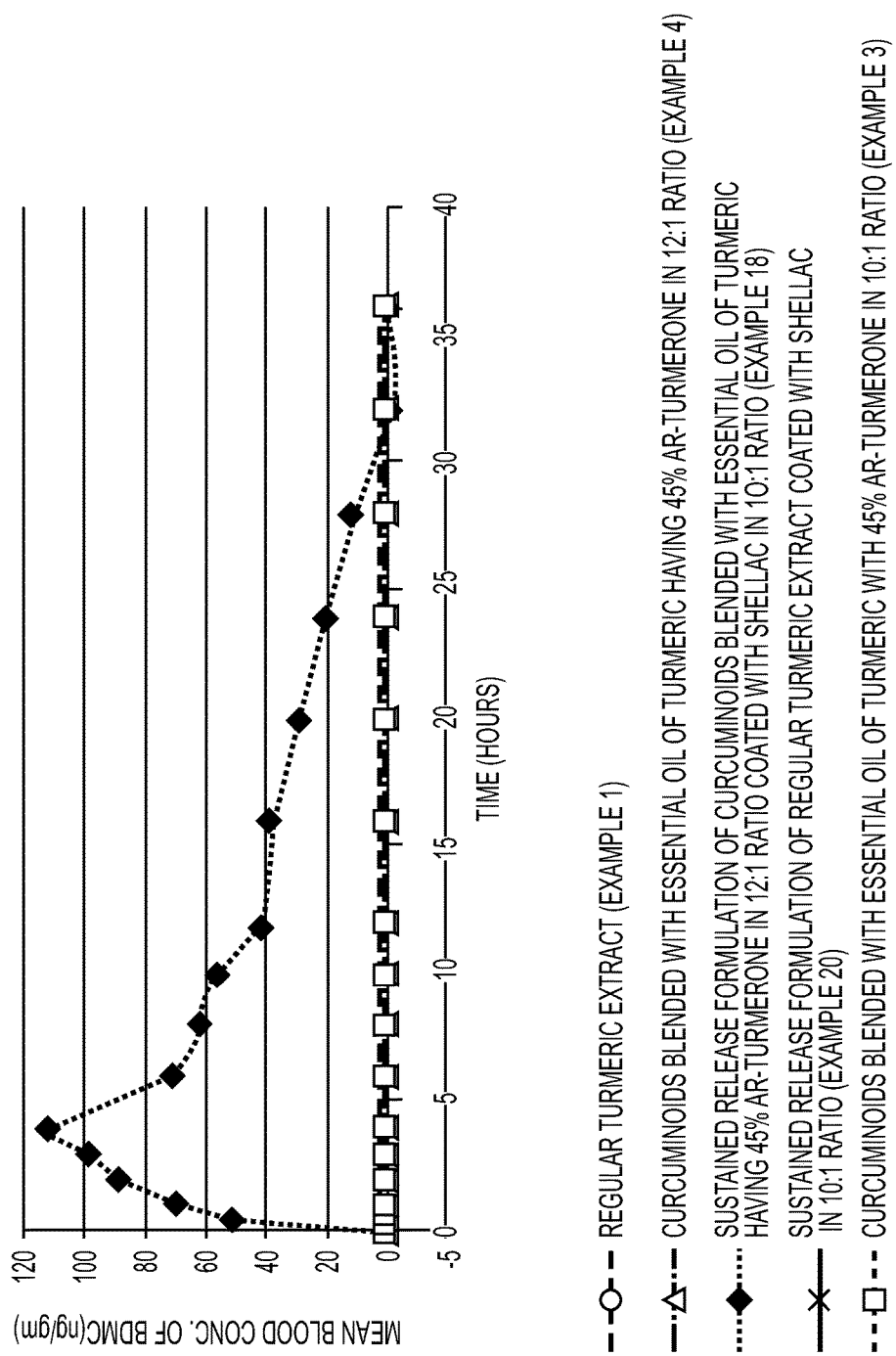
FIG. 21 provides a graph showing Mean blood concentration of BDMC (ng/gm) Vs Time after administering human subjects a sustained release formulation of bioavailable curcumin coated with shellac in 10:1 ratio (example 26 Table 23 b).
Figure 22:
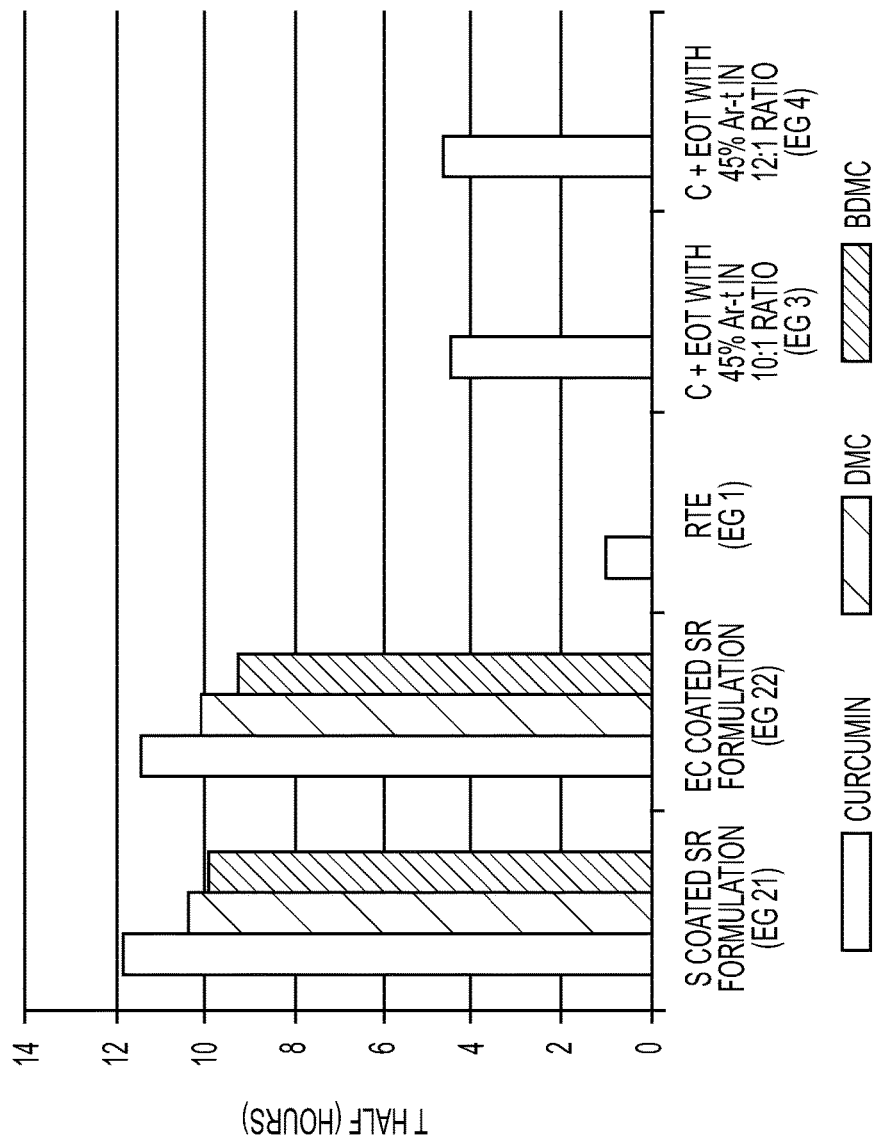
FIG. 22 provides a graph showing T half (Hours) of Sustained release groups, regular turmeric extract and curcuminoids blended with essential oil of turmeric in 10:1 and 12:1 ratios as per example 27.
Figure 23:
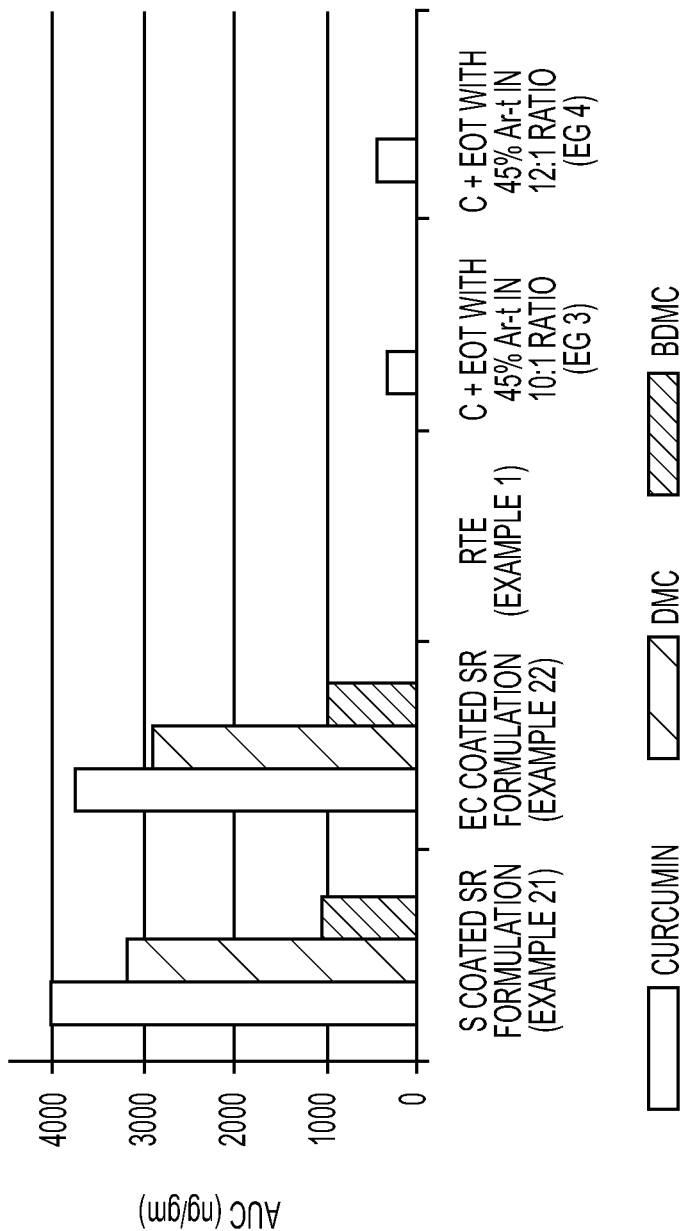
FIG. 23 provides a graph showing AUC (ng/gm) of Sustained release groups, regular turmeric extract and curcuminoids blended with essential oil of turmeric in 10:1 and 12:1 ratios as per example 27.

Blood was collected at different time intervals at baseline, 0.5, 1, 2, 3, 4, 6, 8, 10, 12, 16, 20, 24, 28, 32 and 36 hours post drug. The whole blood was extracted exhaustively with ethyl acetate to recover curcumin. The ethyl acetate extract was analyzed by HPLC on a RP-C18 column (250×4.5 mm) using tetrahydrofuran (THF) as solvent and UV detection at 420 nm. The eluant flow rate was 1 ml/min. The blood level concentration of curcumin, DMC (Demethoxy curcumin) and BDMC (Bis-Demethoxy curcumin) was determined by HPLC against working standards for samples collected at different time points and averaged over the five volunteers. The data is given in Table 24 (FIG. 33). The blood concentration of curcuminoids versus time profile is illustrated in FIG. 13-15 and half life and AUC graphs are shown in FIGS. 22 and 23 respectively. Results show that curcumin was detected only up to 4 hr in the subjects treated with Regular turmeric extract (Example 1). The Cmax was 11.2 ng/gm in the group fed only Regular turmeric extract (Group I).

In subjects treated with curcuminoids blended with essential oil of turmeric with 45% Ar-turmerone in 10:1 and 12:1 ratio showed detection of curcumin up to 8 hours and C max was 90.2 and 115.1 respectively.

The subjects treated with sustained release formulation of curcuminoid blended with essential oil of turmeric having 45% Ar-turmerone prepared as per example 21 showed high curcumin level in the blood. Cmax was 186.4 for subjects treated with formulation prepared in Example 21. Curcumin was also detected up to 36 hr in the blood.

The subjects treated with sustained release formulation of curcuminoid blended with essential oil of turmeric having 45% Ar-turmerone prepared as per example 22 showed a Cmax of 169.6 for subjects treated with formulation prepared in Example 22. Curcumin was also detected up to 36 hr in the blood.

These results suggest that the sustained release formulation need be given only once daily and it will last at least up to 36 hr at significant level required to produce pharmacological effect.

Demethoxy curcumin (DMC) was not detected in the subjects treated with Regular turmeric extract. It was detected in the subjects treated with sustained release formulation prepared as per Example 21 and 22. DMC was detected up to 36 hr in the subjects treated with sustained release formulation prepared as per Example 21 and 22. This further indicates the superiority of sustained release formulation.

Bisdemethoxy curcumin (BDMC) was not detected in the subjects treated with regular turmeric extract. It was detected in the subjects treated with formulations prepared in Example 21 and 22. BDMC was detected up to 36 hr in the subjects treated with sustained release formulation prepared in Example 21 and 22. This also indicates the superiority of sustained release formulations.

Results also indicate that half life ($t_{1/2}$) of sustained release formulations prepared as in example 21 and 22 was increased. Following a single dose administration of sustained release curcuminoid formulation prepared as per Example 21 and 22, the half life (t½) of curcumin was 11.8 and 11.4 hours respectively. Whereas administering single dose of bioavailable curcumin (curcuminoids blended with essential oil of turmeric with 45% Ar-turmerone in 10:1 and 12:1 ratios) formulation prepared as per example 3 and 4, the half life of curcumin was 4.5 and 4.7 respectively. Administering a single dose administration of sustained release curcuminoid formulation prepared as per Example 21 resulted in a half life (t½) of demethoxycurcumin and bisdemethoxycurcumin was 10.4 and 10.2 hours respectively. But after administering bioavailable curcumin formulation demethoxycurcumin and bisdemethoxycurcumin was not detected in blood. Administering the sustained release curcuminoid formulation prepared as per Example 22, the half life (t½) of demethoxycurcumin and bisdemethoxycurcumin was about 9.9 and about 9.2 hours respectively. Administering regular turmeric extract resulted in a half life (t½) of curcumin of about 1.07 hours. Demethoxycurcumin and bisdemethoxycurcumin was not detected in blood after administration of the regular turmeric extract.

Higher $t_{1/2}$ indicates the longer stay of the curcuminoids in the formulation in the body.

Area under the curve (AUC0-t) of curcumin, demethoxy curcumin and bisdemethoxy curcumin in sustained release groups were calculated from the respective graphs, which showed found that AUC was increased. After a single dosage of sustained release curcuminoid formulation prepared as per Example 21 and 22, the AUC (ng/gm) of curcumin in blood was about 4002.5 and about 3752.8 respectively. Whereas after a single dosage of bioavailable curcumin formulation prepared as per example 3 and 4, the AUC of curcumin in blood was about 321.9 and about 414.9 ng/gm respectively. After a single dosage of sustained release curcuminoid formulation prepared as per Example 21, the AUC of demethoxycurcumin and bisdemethoxycurcumin in blood was about 3226.1 and about 1056.8 ng/gm respectively. But after administering a single dose of bioavailable curcumin formulation demethoxycurcumin and bisdemethoxycurcumin was not detected in blood. In sustained release curcuminoid formulation prepared as per Example 22, the AUC of demethoxycurcumin and bisdemethoxycurcumin was about 2939.7 and about 957.1 ng/gm respectively. Administering regular turmeric extract resulted in an AUC (ng/gm) of curcumin of about 23.9. Demethoxycurcumin and bisdemethoxycurcumin was not detected in blood after administration of the regular turmeric extract.

Example 28

Tissue Distribution Study in Rabbits

Rabbits weighing 2-2.5 Kg were used for the study. Animals were divided into 10 groups and 4 animals were used for each group. The dosage administered was 60 mg curcuminoids/Kg body weight of the rabbit.

Group 1 animal were given vehicle, Tween 80.

Group 2 animals were given Regular turmeric extract prepared as per example 1 having 95% curcuminoids of which curcumin (78.16%), demethoxycurcumin (13.79%) and bisdemethoxycurcumin (2.87%) solubilized in Tween 80.

To Group 3 animals, ethyl cellulose coated sustained release formulation (Prepared as per example 5) of curcuminoids blended with essential oil of turmeric having 45% Ar-turmerone in 10:1 ratio (68% Curcumin, 12% Demethoxy curcumin, 2.5% Bisdemethoxy curcumin, 6% Essential oil of turmeric having 45% Ar-turmerone and 9% Ethyl cellulose) solubilized in Tween 80 and fed.

To Group 4 animals, ethyl cellulose coated Sustained release formulation (Prepared as per example 6) of curcuminoids blended with essential oil of turmeric having 45% Ar-turmerone in 12:1 ratio (Curcumin 68.5%, Demethoxy curcumin 12.5%, Bisdemethoxy curcumin 2.5%, Essential oil of turmeric having 45% Ar-turmerone 5% and Ethyl cellulose 9%) solubilized in Tween 80 and fed.

Group 5 animals were given Regular turmeric extract sustained release formulation (Prepared as per example 7) having Curcumin 72%, Demethoxy curcumin 12%, Bisdemethoxy curcumin 3% and Ethyl cellulose 9% solubilized in Tween 80.

To Group 6 animals, Shellac coated Sustained release formulation of curcuminoids (Prepared as per example 17) blended with essential oil of turmeric having 45% Ar-turmerone in 10:1 ratio (66.7% Curcumin, 13.6% Demethoxy curcumin, 2.7% Bisdemethoxy curcumin, 8.3% Essential oil of turmeric having 45% Ar-turmerone and 8.7% shellac.) solubilized in Tween 80 and fed.

To Group 7 animals, Shellac coated Sustained release formulation (Prepared as per example 18) of curcuminoids blended with essential oil of turmeric having 45% Ar-turmerone in 12:1 ratio (67.6% Curcumin, 13.9% Demethoxy curcumin, 2.8% Bisdemethoxy curcumin, 7% Essential oil of turmeric having 45% Ar-turmerone and 8.7% shellac) solubilized in Tween 80 and fed.

Group 8 animals were given shellac coated Regular turmeric extract sustained release formulation (Prepared as per example 20) of which 70.7% Curcumin, 17.3% Demethoxy curcumin, 3.3% Bisdemethoxy curcumin and 8.7% Shellac solubilized in Tween 80.

To Group 9 animals, curcuminoids blended with essential oil of turmeric having 45% Ar-turmerone in 10:1 ratio (Prepared as per example 3) with curcumin 69.8%, demethoxy curcumin 17.0%, bisdemethoxy curcumin 3.2% and essential oil of turmeric having 45% Ar-turmerone 8.8% solubilized in Tween 80 and fed.

To Group 10 animals, curcuminoids blended with essential oil of turmeric having 45% Ar-turmerone in 12:1 ratio (Prepared as per example 4) with 70.0% curcumin, 17.1% demethoxy curcumin, 3.3% bisdemethoxy curcumin and 7.3% essential oil of turmeric having 45% Ar-turmerone solubilized in Tween 80 and fed.

The study drugs were given by oral route. Twenty four hours post drug rabbits were sacrificed by cervical dislocation and dissected to obtain various tissues (Heart, Kidney, Brain, Liver, Pancreas, Lungs, and Skin). Each tissue was weighed and stored at −80° C. until analysis.

Tissues were homogenized and extracted with chloroform-methanol (2:1). The homogenate was filtered through a Whatman filter paper and the filtrate collected and mixed thoroughly with 0.2 vol of 0.9% NaCl solution and centrifuged. The upper layer was siphoned off. The lower layer was evaporated to dryness under a stream of nitrogen at 40-45° C. in a "Turbo Vap" Concentration Work Station (Caliper Life Sciences, USA).

Dried samples of tissues were analyzed on HPLC. The dried samples were dissolved in 2 ml of acetone using a vortex mixer and analyzed by HPLC in a Shimadzu LC 20AD Liquid Chromatograph system with SPD-M20A UV detector in isocratic mode. The column used was C18 ODS Phenomenox (250×4.6 mm, 5μ particle size) using 40% tetrahydrofuran (THF), 60% water containing 1% citric acid (pH adjusted to 3 with concentrated KOH solution) as solvent system and UV detection at 420 nm. The eluent flow rate was 1 ml/min.

Group 1 (Control Group)

| S1 | Tissues | Curcumin(ng/g) | DMC | BDMC |
|---|---|---|---|---|
| 1 | Lungs | ND | ND | ND |
| 2 | Heart | ND | ND | ND |
| 3 | Kidney | ND | ND | ND |
| 4 | Brain | ND | ND | ND |
| 5 | Liver | ND | ND | ND |
| 6 | Pancreas | ND | ND | ND |
| 7 | Skin | ND | ND | ND |

Group 2—Regular Turmeric Extract [Prepared as Per Example 1]

| Sl No:- | Tissues | Curcumin ng/g | DMC ng/g | BDMC ng/g |
|---|---|---|---|---|
| 1 | Lungs | 0.1 | ND | ND |
| 2 | Heart | 1.4 | ND | ND |
| 3 | Kidney | ND | ND | ND |
| 4 | Brain | 0.6 | ND | ND |
| 5 | Liver | 0.2 | ND | ND |
| 6 | Pancreas | ND | ND | ND |
| 7 | Skin | ND | ND | ND |

Group 3—Sustained Release Formulation of Curcuminoid Mixture Blended with EOT Having 45% Ar-Turmerone in 10:1 Ratio Coated with Ethyl Cellulose in 10:1 Ratio [Prepared as Per Example 5]

| Sl No:- | Tissues | Curcumin ng/g | DMC ng/g | BDMC ng/g |
|---|---|---|---|---|
| 1 | Lungs | 28.6 | 13.5 | 8.2 |
| 2 | Heart | 356.1 | 198.2 | 88.3 |
| 3 | Kidney | 22.4 | 9.6 | 10.4 |
| 4 | Brain | 28.4 | 11.3 | 6.6 |
| 5 | Liver | 120.5 | 60.1 | 25.6 |
| 6 | Pancreas | 310.3 | 154.7 | 75.6 |
| 7 | Skin | 16.5 | 9.4 | 4.8 |

Group 4—Sustained Release Formulation of Curcuminoid Mixture Blended with EOT Having 45% Ar-Turmerone in 12:1 Ratio Coated with Ethyl Cellulose in 10:1 Ratio [Prepared as Per Example 6]

| Sl No:- | Tissues | Curcumin ng/g | DMC ng/g | BDMC ng/g |
|---|---|---|---|---|
| 1 | Lungs | 29.3 | 12.9 | 8 |
| 2 | Heart | 318.12 | 201.2 | 92.3 |
| 3 | Kidney | 31.26 | 14.6 | 9.8 |
| 4 | Brain | 28.65 | 9.5 | 10.9 |
| 5 | Liver | 136.5 | 64.7 | 29.6 |
| 6 | Pancreas | 325.3 | 149.7 | 81.6 |
| 7 | Skin | 17.1 | 9.5 | 3.6 |

Group 5—Regular Turmeric Extract Sustained Release Formulation Coated with Ethyl Cellulose in 10:1 Ratio [Prepared as Per Example 7]

| Sl No:- | Tissues | Curcumin ng/g | DMC ng/g | BDMC ng/g |
|---|---|---|---|---|
| 1 | Lungs | 0.3 | ND | ND |
| 2 | Heart | 1.8 | ND | ND |
| 3 | Kidney | ND | ND | ND |
| 4 | Brain | ND | ND | ND |
| 5 | Liver | 0.8 | ND | ND |
| 6 | Pancreas | ND | ND | ND |
| 7 | Skin | ND | ND | ND |

Group 6—Sustained Release Formulation of Curcuminoid Mixture Blended with EOT Having 45% Ar-Turmerone in 10:1 Ratio Coated with Shellac in 10:1 Ratio [Prepared as Per Example 17]

| Sl No:- | Tissues | Curcumin ng/g | DMC ng/g | BDMC ng/g |
|---|---|---|---|---|
| 1 | Lungs | 35.1 | 15.3 | 10.3 |
| 2 | Heart | 318.21 | 213.6 | 142.1 |
| 3 | Kidney | 24.2 | 10.5 | 6.3 |
| 4 | Brain | 25.9 | 12.4 | 7.9 |
| 5 | Liver | 117.6 | 52.4 | 62.5 |
| 6 | Pancreas | 307.3 | 194.2 | 82.4 |
| 7 | Skin | 20.4 | 13.2 | 5.2 |

Group 7—Sustained Release Formulation of Curcuminoid Mixture Blended with EOT Having 45% Ar-Turmerone in 12:1 Ratio Coated with Shellac in 10:1 Ratio [Prepared as Per Example 18]

| Sl No:- | Tissues | Curcumin ng/g | DMC ng/g | BDMC ng/g |
|---|---|---|---|---|
| 1 | Lungs | 41.8 | 17.4 | 11.2 |
| 2 | Heart | 342.77 | 225.6 | 135.4 |
| 3 | Kidney | 29.95 | 11.8 | 7.2 |
| 4 | Brain | 30.87 | 12.4 | 8.6 |
| 5 | Liver | 128.15 | 63.5 | 48.7 |
| 6 | Pancreas | 365.2 | 188 | 100.1 |
| 7 | Skin | 17.33 | 10.8 | 4.3 |

Group 8—Regular Turmeric Extract Sustained Release Formulation Coated with Shellac in 10:1 Ratio [Prepared as Per Example 20]

| Sl No:- | Tissues | Curcumin ng/g | DMC ng/g | BDMC ng/g |
|---|---|---|---|---|
| 1 | Lungs | 0.2 | ND | ND |
| 2 | Heart | 1.1 | ND | ND |
| 3 | Kidney | ND | ND | ND |
| 4 | Brain | ND | ND | ND |
| 5 | Liver | 0.8 | ND | ND |
| 6 | Pancreas | ND | ND | ND |
| 7 | Skin | ND | ND | ND |

Group 9—Curcuminoid Mixture Blended with EOT Having 45% Ar-Turmerone in 10:1 Ratio [Prepared as Per Example 3]

| Sl No:- | Tissues | Curcumin ng/g | DMC ng/g | BDMC ng/g |
|---|---|---|---|---|
| 1 | Lungs | 5.0 | ND | ND |
| 2 | Heart | 47.1 | ND | ND |
| 3 | Kidney | 4.8 | ND | ND |
| 4 | Brain | 3.6 | ND | ND |
| 5 | Liver | 10.5 | ND | ND |
| 6 | Pancreas | 30.1 | ND | ND |
| 9 | Skin | 1.3 | ND | ND |

Group 10—Curcuminoid Mixture Blended with EOT Having 45% Ar-Turmerone in 12:1 Ratio [Prepared as Per Example 4]

| S1 No:- | Tissues | Curcumin ng/g | DMC ng/g | BDMC ng/g |
|---|---|---|---|---|
| 1 | Lungs | 5.3 | ND | ND |
| 2 | Heart | 50.8 | ND | ND |
| 3 | Kidney | 4.7 | ND | ND |
| 4 | Brain | 3.5 | ND | ND |
| 5 | Liver | 11.9 | ND | ND |
| 6 | Pancreas | 34.1 | ND | ND |
| 9 | Skin | 1.6 | ND | ND |

In the study, using a rabbit model, pancreas, heart and liver showed a better detection of curcumin, demethoxycurcumin and bisdemethoxycurcumin after twenty four hours post dosing of shellac and ethyl cellulose coated sustained release formulation of curcuminoid mixture blended with essential oil of turmeric having 45% Ar-turmerone in 10:1 or in 12:1 ratios (Group 3, 4, 6 and 7). Kidney, lungs, skin and brain showed moderate detection of curcumin, demethoxycurcumin and bisdemethoxycurcumin after dosing sustained release formulation of curcuminoid mixture blended with essential oil of turmeric having 45% Ar-turmerone in 10:1 or in 12:1 ratios (Group 3, 4, 6 and 7).

In groups 9 and 10 animals after consuming curcuminoid mixture blended with essential oil of turmeric having 45% Ar-turmerone in 10:1 or in 12:1 ratios formulations, all the tissues showed detection of curcumin only.

In Group 2, 5 and 8 animals after consuming regular turmeric extract and sustained release regular turmeric extract formulations, all the tissues showed detection of curcumin only. In the control group (Group 1) there is no absorption of curcuminoids in the tissues. All other tissues that of spleen, uterus, seminal Vesicle, testis and prostate also show significant detection of curcumin, demethoxycurcumin and bisdemethoxycurcumin after dosing shellac and ethyl cellulose coated sustained release formulation of curcuminoid mixture blended with essential oil of turmeric having 45% Ar-turmerone in 10:1 or in 12:1 ratios.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

I claim:

1. A sustained release curcuminoid composition comprising a bioavailable curcumin composition and a release rate controlling excipient, wherein the bioavailable composition of curcumin comprises a curcuminoid mixture and an added essential oil of turmeric, the curcuminoid mixture comprises curcumin, demethoxycurcumin and bisdemethoxycurcumin, and, the added essential oil of turmeric comprises about 40% to about 50% of ar-turmerone, wherein the release rate controlling excipient is selected from the group consisting of ethyl cellulose, shellac, copolymer of ethyl acrylate and methyl methacrylate, and combinations thereof.

2. The sustained release curcuminoid composition of claim 1, wherein the added essential oil of turmeric comprises about 45% ar-turmerone.

3. The sustained release curcuminoid composition of claim 1, wherein a weight ratio of the curcuminoid mixture to the added essential oil of turmeric ranges from about 1:3 to about 99:1.

4. The sustained release curcuminoid composition of claim 1, wherein the weight ratio of the curcuminoid mixture to the added essential oil of turmeric is about 10:1.

5. The sustained release curcuminoid composition of claim 1, wherein the weight ratio of the curcuminoid mixture to the added essential oil of turmeric is about 12:1.

6. The sustained release curcuminoid composition of claim 1, wherein a weight ratio of the bioavailable curcumin composition to the release rate controlling excipient ranges from about 3:1 to about 50:1.

7. The sustained release curcuminoid composition of claim 1, wherein a weight ratio of the bioavailable curcumin composition to the release rate controlling excipient ranges from about 10:1 to about 20:1.

8. The sustained release curcuminoid composition of claim 1, wherein a weight ratio of the bioavailable curcumin composition to the release rate controlling excipient is about 10:1.

9. The sustained release curcuminoid composition of claim 1, wherein a weight ratio of the bioavailable curcumin composition to the release rate controlling excipient is about 14:1.

10. The sustained release curcuminoid composition of claim 1, wherein a weight ratio of the bioavailable curcumin composition to the release rate controlling excipient is about 20:1.

11. The sustained release curcuminoid composition of claim 1, wherein a weight ratio of the bioavailable curcumin composition to the shellac ranges from about 3:1 to about 50:1.

12. The sustained release curcuminoid composition of claim 1, wherein the weight ratio of the bioavailable curcumin composition to the shellac ranges from about 10:1 to about 14:1.

13. The sustained release curcuminoid composition of claim 1, wherein a weight ratio of the bioavailable curcumin composition to the shellac is about 10:1.

14. The sustained release curcuminoid composition of claim 1, wherein a weight ratio of the bioavailable curcumin composition to the shellac is about 14:1.

15. The sustained release curcuminoid composition of claim 1, wherein the shellac forms a coating on the bioavailable curcumin composition.

16. The sustained release curcuminoid composition of claim 1, wherein a weight ratio of the bioavailable curcumin composition to the ethyl cellulose ranges from about 3:1 to about 50:1.

17. The sustained release curcuminoid composition of claim 1, wherein the weight ratio of the e bioavailable curcumin composition to the ethyl cellulose ranges from about 10:1 to about 20:1.

18. The sustained release curcuminoid composition of claim 1, wherein a weight ratio of the bioavailable curcumin composition to the ethyl cellulose is about 10:1.

19. The sustained release curcuminoid composition of claim 1, wherein a weight ratio of the bioavailable curcumin composition to the ethyl cellulose is about 20:1.

20. The sustained release curcuminoid composition of claim 1, wherein the ethyl cellulose forms a coating on the bioavailable curcumin composition.

21. The sustained release curcuminoid composition of claim 1, wherein a weight ratio of the bioavailable curcumin composition to the copolymer of ethyl acrylate and methyl methacrylate ranges from about 3:1 to about 50:1.

22. The sustained release curcuminoid composition of claim 1, wherein the weight ratio of the bioavailable curcumin composition to the copolymer of ethyl acrylate and methyl methacrylate ranges from about 10:1 to about 20:1.

23. The sustained release curcuminoid composition of claim 1 for oral administration.

24. The sustained release curcuminoid composition of claim 1, wherein curcumin, demethoxycurcumin and bisdemethoxycurcumin are detected in the blood for about 24 to about 36 hours.

25. The sustained release curcuminoid composition of claim 1, wherein a single dosage of the composition provides curcumin, demethoxycurcumin and bisdemethoxycurcumin in the body for 24 hours.

26. The sustained release curcuminoid composition of claim 1, wherein a single dosage of the composition provides curcumin, demethoxycurcumin and bisdemethoxycurcumin in the body for 36 hours.

27. The sustained release curcuminoid composition of claim 1, wherein administering a single dosage of the sustained release curcuminoid composition enhances bioavailability of curcumin, demethoxycurcumin and bisdemethoxycurcumin in the blood for 24 hours when compared to administration of the bioavailable curcumin composition alone.

28. The sustained release curcuminoid composition of claim 1, wherein administering a single dosage of the sustained release curcuminoid composition enhances bioavailability of curcumin, demethoxycurcumin and bisdemethoxycurcumin in the blood for 36 hours when compared to administration of the bioavailable curcumin composition alone.

29. The sustained release curcuminoid composition of claim 1, wherein administering a single dosage of the sustained release curcuminoid composition enhances bioavailability of curcumin, demethoxycurcumin and bisdemethoxycurcumin in a body tissue for more than 24 hours when compared to administration of the bioavailable curcumin composition alone.

30. The sustained release curcuminoid composition of claim 1, wherein the half-life ($t_{1/2}$) of the curcumin, demethoxycurcumin and bisdemethoxycurcumin in the blood is increased when compared to the half life ($t_{1/2}$) of curcumin, demethoxycurcumin and bisdemethoxycurcumin in the blood upon administration of the bioavailable curcumin composition alone.

31. The sustained release curcuminoid composition of claim 1, wherein the area under the curve (AUC) of the curcumin, demethoxycurcumin and bisdemethoxycurcumin in the blood is increased when compared to the AUC of curcumin, demethoxycurcumin and bisdemethoxycurcumin upon administration of the bioavailable curcumin composition alone.

32. A dosage form comprising the sustained release curcuminoid composition of claim 1, wherein the dosage form is selected from the group consisting of powder, pellets, granules, tablets and capsules.

* * * * *